US011407792B2

(12) United States Patent
Silberg et al.

(10) Patent No.: US 11,407,792 B2
(45) Date of Patent: Aug. 9, 2022

(54) REGULATING ELECTRON FLOW USING FRAGMENTED PROTEINS

(71) Applicant: WILLIAM MARSH RICE UNIVERSITY, Houston, TX (US)

(72) Inventors: Jonathan Silberg, Houston, TX (US); Joshua T. Atkinson, Houston, TX (US); Ian J. Campbell, Houston, TX (US); George N. Bennett, Houston, TX (US)

(73) Assignee: William Marsh Rice University, Houston, TX (US)

( * ) Notice: Subject to any disclaimer, the term of this patent is extended or adjusted under 35 U.S.C. 154(b) by 404 days.

(21) Appl. No.: 16/186,226

(22) Filed: Nov. 9, 2018

(65) Prior Publication Data

US 2019/0135878 A1 May 9, 2019

Related U.S. Application Data

(60) Provisional application No. 62/583,770, filed on Nov. 9, 2017.

(51) Int. Cl.
*C07K 14/21* (2006.01)
*G01N 33/566* (2006.01)
*C07K 14/415* (2006.01)
*G01N 33/542* (2006.01)

(52) U.S. Cl.
CPC ............ *C07K 14/21* (2013.01); *C07K 14/415* (2013.01); *G01N 33/542* (2013.01); *G01N 33/566* (2013.01); *C07K 2319/00* (2013.01); *C07K 2319/73* (2013.01); *G01N 2333/79* (2013.01)

(58) Field of Classification Search
None
See application file for complete search history.

(56) References Cited

U.S. PATENT DOCUMENTS 5,466,590 A * 11/1995 Sariaslani ............... C07K 14/79
435/189
2009/0044286 A1 2/2009 Gambhir et al.

OTHER PUBLICATIONS

Aliverti et al., "Biochemical and crystallographic characterization of ferredoxin-NADP(+) reductase from nonphotosynthetic tissues," *Biochemistry*, 40:14501-14508, 2001.
Angeleri et al., "Interplay of SpkG kinase and the Slr0151 protein in the phosphorylation of ferredoxin 5 in *Synechocystis* sp. strain PCC 6803," *FEBS Letters*, 592:411-421, 2018.
Atkinson et al., "Abstract: Controlling energy flow in bacteria using engineered ligand-responsive protein electron carriers," Synthetic Biology Engineering Evolution Design SEED, Vancouver, BC, 2017.
Atkinson et al., "Abstract: Controlling energy flow in bacteria using engineered ligand-responsive protein electron carriers," 25th Texas Protein Folders and Function Meeting, Cleveland, TX, 2017.
Atkinson et al., "Abstract: Designing chemical-responsive protein electron carriers to control cellular electron flow," 2nd Annual Asilomar Bioelectronics Conference, Pacific Grove, CA, 2017.
Atkinson et al., "Abstract: Rational design of split ferredoxins that function as electron transfer and gates in *Escherichia coli*," 4th Penn State Bioinorganic Workshop, State College, PA, 2016.
Atkinson et al., "Abstract: Two-fragment ferredoxins that function as electron transfer and gates," 72nd Annual ACS Southwest Regional Meeting, Abstract 190, Nov. 2016.
Atkinson et al., "Cellular Assays for Ferredoxins: A Strategy for Understanding Electron Flow through Protein Carriers That Link Metabolic Pathways," *Biochemistry*, 55:7047-7064, 2016.
Bak & Elliott, "Alternative FeS cluster ligands: tuning redox potentials and chemistry," *Current Opinion in Chemical Biology*, 19:50-58, 2014.
Banaszynski et al., "Characterization of the FKBP.rapamycin.FRB ternary complex," *J. Am. Chem. Soc.*, 127:4715-4721, 2005.
Barstow et al., "A synthetic system links FeFe-hydrogenases to essential *E. coli* sulfur metabolism," *Journal of Biological Engineering*, 5:7, 2011.
Dawson et al., "Electron transport in a dioxygenase-ferredoxin complex: Long range charge coupling between the Rieske and non-heme iron center," *PLoS ONE*, 11:e0162031, 2016.
DeRose et al., "Manipulating signaling at will: chemically-inducible dimerization (CID) techniques resolve problems in cell biology," *Pflugers Arch.*, 465:409-417, 2013.
Edgar, "MUSCLE: multiple sequence alignment with high accuracy and high throughput," *Nucleic Acids Research*, 32:1792-1797, 2004.
Eilenberg et al., "The dual effect of a ferredoxin-hydrogenase fusion protein in vivo: successful divergence of the photosynthetic electron flux towards hydrogen production and elevated oxygen tolerance," *Biotechnology for Biofuels*, 9:182, 2016.
Engler et al., "A One Pot, One Step, Precision Cloning Method with High Throughput Capability," *PLoS ONE*, 3:e3647, 2008.
Fish et al., "Structural basis for the thermostability of ferredoxin from the cyanobacterium Mastigocladus laminosus," *Journal of Molecular Biology*, 350:599-608, 2005.
Guntas et al., "Directed evolution of protein switches and their application to the creation of ligand-binding proteins," *Proc. Natl. Acad. Sci. U.S.A.*, 102:11224-11229, 2005.
Hirasawa et al., "Oxidation-reduction properties of maize ferredoxin: sulfite oxidoreductase," *Biochimica Et Biophysica Acta*, 1608:140-148, 2004.
Hirrlinger et al., "Split-CreERT2: Temporal Control of DNA Recombination Mediated by Split-Cre Protein Fragment Complementation," *PLoS ONE*, 4:e8354, 2009.
Jensen et al., "Engineering of a synthetic electron conduit in living cells," *Proc. Natl. Acad. Sci. U.S.A.*, 107:19213-19218, 2010.

(Continued)

*Primary Examiner* — Anand U Desai
(74) *Attorney, Agent, or Firm* — Parker Highlander PLLC

(57) ABSTRACT

Engineered protein electron carriers, microorganisms expressing the same, and methods detecting regulated electron flow are described.

14 Claims, 30 Drawing Sheets
(27 of 30 Drawing Sheet(s) Filed in Color)
Specification includes a Sequence Listing.

(56) References Cited

OTHER PUBLICATIONS

Kallio et al., "An engineered pathway for the biosynthesis of renewable propane" *Nature Communications*, 5:4731, 2014.
Kim et al., "Structural and mutational studies of an electron transfer complex of maize sulfite reductase and ferredoxin," *Journal of Biochemistry*, 160:101-109, 2016.
Kracke, et al., "Microbial electron transport and energy conservation—the foundation for optimizing bioelectrochemical systems," *Frontiers in Microbiology*, 6:575, 2015.
Kurisu et al., "Structure of the electron transfer complex between ferredoxin and ferredoxin-NADP(+) reductase," *Nature Structural Biology*, 8:117-121, 2001.
Kwon & Jewett, "High-throughput preparation methods of crude extract for robust cell-free protein synthesis," *Scientific Reports*, 5:srep08663, 2015.
Lin et al., "Cell-trappable fluorescent probes for endogenous hydrogen sulfide signaling and imaging H2O2-dependent H2S production," *Proc. Natl. Acad. Sci. U.S.A.*, 110:7131-7135, 2013.
Menke et al., "MATT: Local Flexibility Aids Protein Multiple Structure Alignment," *PLoS Computational Biology*, 4:e10, 2008.
Michnick, et al., "Solution structure of FKBP," *Science*, 252:836-839, 1991.
Moscatiello et al., "Identification of ferredoxin II as a major calcium binding protein in the nitrogen-fixing symbiotic bacterium Mesorhizobium loti," *BMC Microbiology*, 15:16, 2015.
Ohmuto-Matsuyama et al., "Demonstration of protein-fragment complementation assay using purified firefly luciferase fragments," *BMC Biotechnology*, 13:31, 2013.
Paige et al., "Estrogen receptor (ER) modulators each induce distinct conformational changes in ER alpha and ER beta," *Proc. Natl. Acad. Sci. U.S.A.*, 96:3999-4004, 1999.
Paulmurugan & Gambhir, "An intramolecular folding sensor for imaging estrogen receptor-ligand interactions," *Proc. Natl. Acad. Sci. U.S.A.*, 103:15883-15888, 2006.
Pelletier et al., "Oligomerization domain-directed reassembly of active dihydrofolate reductase from rationally designed fragments," *Proc. Natl. Acad. Sci. U.S.A.*, 95:12141-12146, 1998.
Reinke et al., "A synthetic coiled-coil interactome provides heterospecific modules for molecular engineering," *Journal the American Chemical Society*, 132:6025-6031, 2010.
Roegner et al., "Metabolic engineered of cyanobacteria for the production of hydrogen from water," *Biochem. Soc. Trans.*, 41:1254-1259, 2013.
Rumpel et al., "Enhancing hydrogen production of microalgae by redirecting electrons from photosystem I to hydrogenase," *Energy Environ. Sci.*, 7:3296-3301, 2014.
Salis et al., "Automated design of synthetic ribosome binding sites to control protein expression," *Nature Biotechnology*, 27:946-950, 2009.
Schlesier et al., "A Conformational Switch Triggers Nitrogenase Protection from Oxygen Damage by Shethna Protein II (FeSII)," *Journal of the American Chemical Society* 138:239-247, 2016.
Segall-Shapiro et al., "Mesophilic and hyperthermophilic adenylate kinases differ in their tolerance to random fragmentation," *Journal of Molecular Biology*, 406:135-148, 2011.
Shian et al., "The structural basis of estrogen receptor/coactivator recognition and the antagonism of this interaction by tamoxifen," *Cell*, 95:927-937, 1998.
Shomar et al., "Metabolic engineering of a carbapenem antibiotic synthesis pathway in *Escherichia coli*," *Nature Chemical Biology*, 14:794-800, 2018.
Sousa et al., "Early bioenergetic evolution," *Philosophical Transactions of the Royal Society of London. Series B, Biological Sciences*, 368:20130088, 2013.
Ta & Vickery, "Cloning, sequencing, and overexpression of a [2Fe-2S] ferredoxin gene from *Escherichia coli*," *The Journal of Biological Chemistry*, 267:11120-11125, 1992.
Tanenbaum et al., "Crystallographic comparison of the estrogen and progesterone receptor's ligand binding domains," *Proc. Natl. Acad. Sci. U.S.A.*, 95:5998-6003, 1998.
Thomas et al., "Programming Post-Translational Control over the Metabolic Labeling of Cellular Proteins with a Noncanonical Amino Acid," *ACS Synth. Biol.*, 6:1572-1583, 2017.
Thompson et al., "SYNZIP protein interaction toolbox: in vitro and in vivo specifications of heterospecific coiled-coil interaction domains," *ACS Synth. Biol.*, 1:118-129, 2012.
Webster et al., "An arsenic-specific biosensor with genetically engineered Shewanella oneidensis in a bioelectrochemical system," *Biosensors & Bioelectronics*, 62:320-324, 2014.
Yang et al., "Modular electron-transport chains from eukaryotic organelles function to support nitrogenase activity," *Proc. Natl. Acad. Sci. U.S.A.*, 114:E2460-E2465, 2017.

* cited by examiner

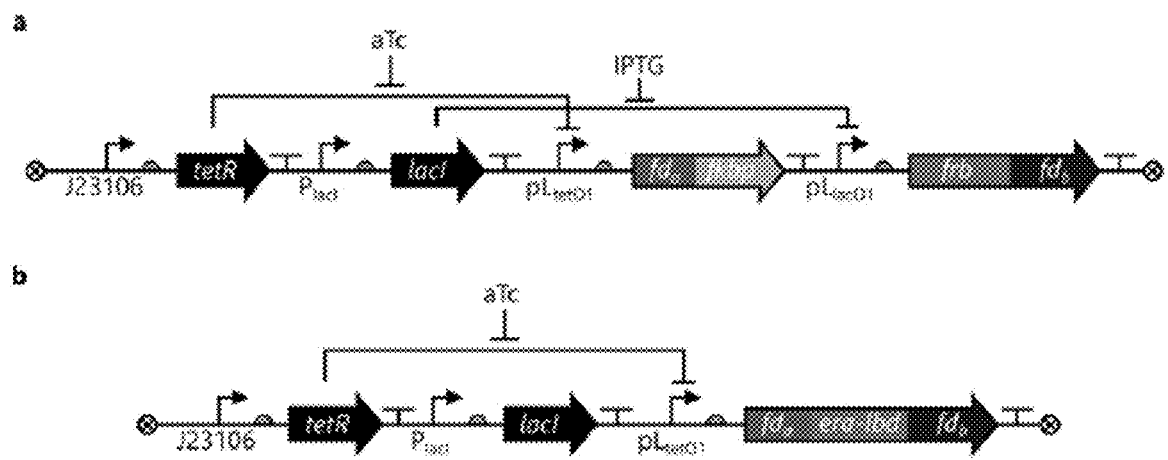
FIGS. 31A-B
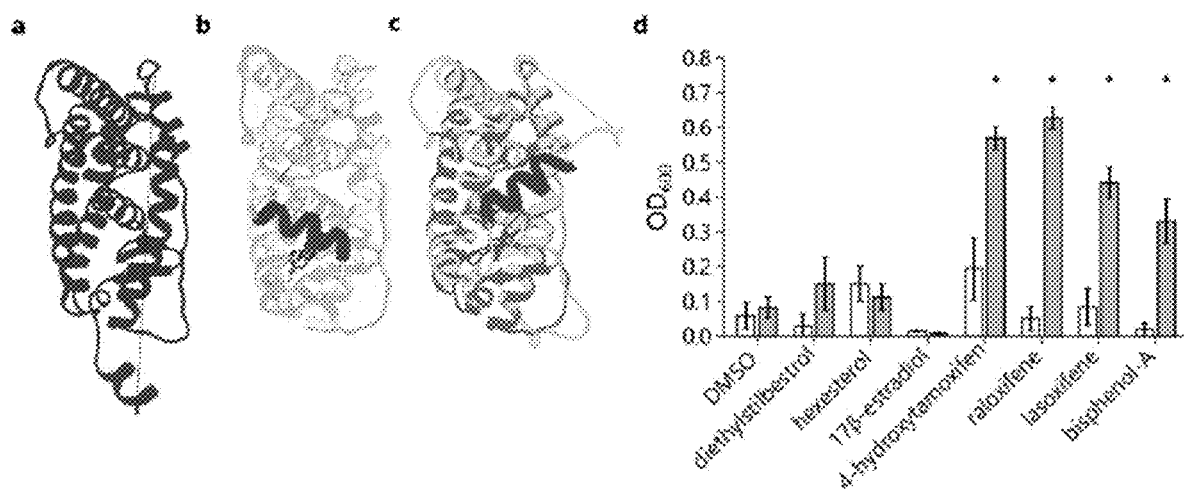
FIGS. 32A-D

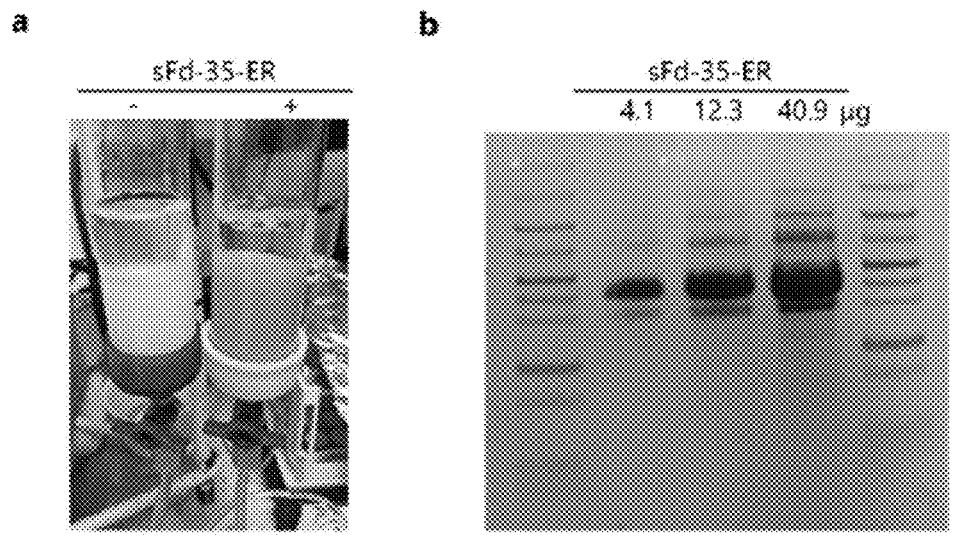
FIGS. 33A-B
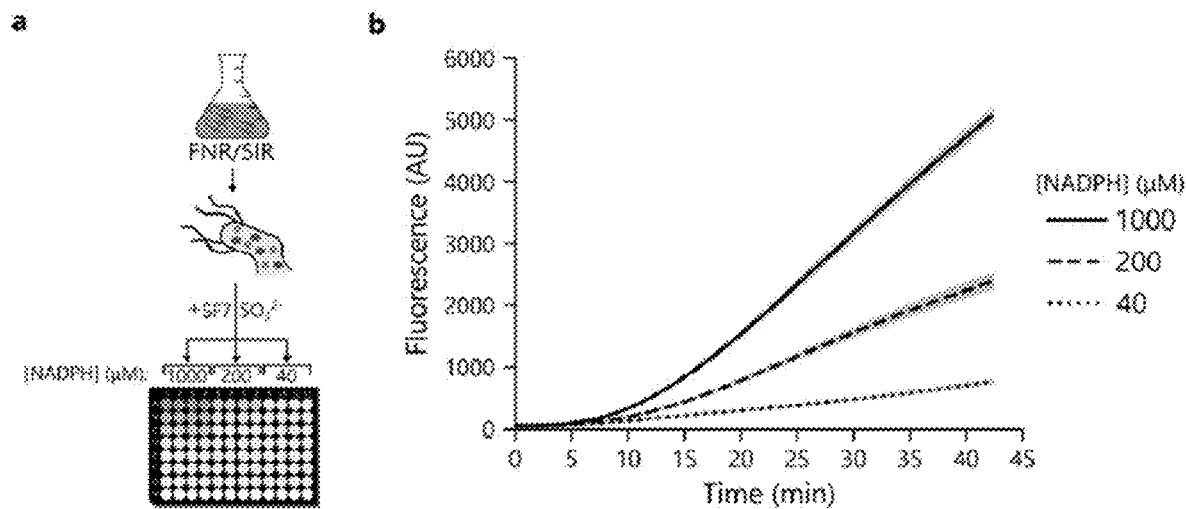
FIGS. 34A-B

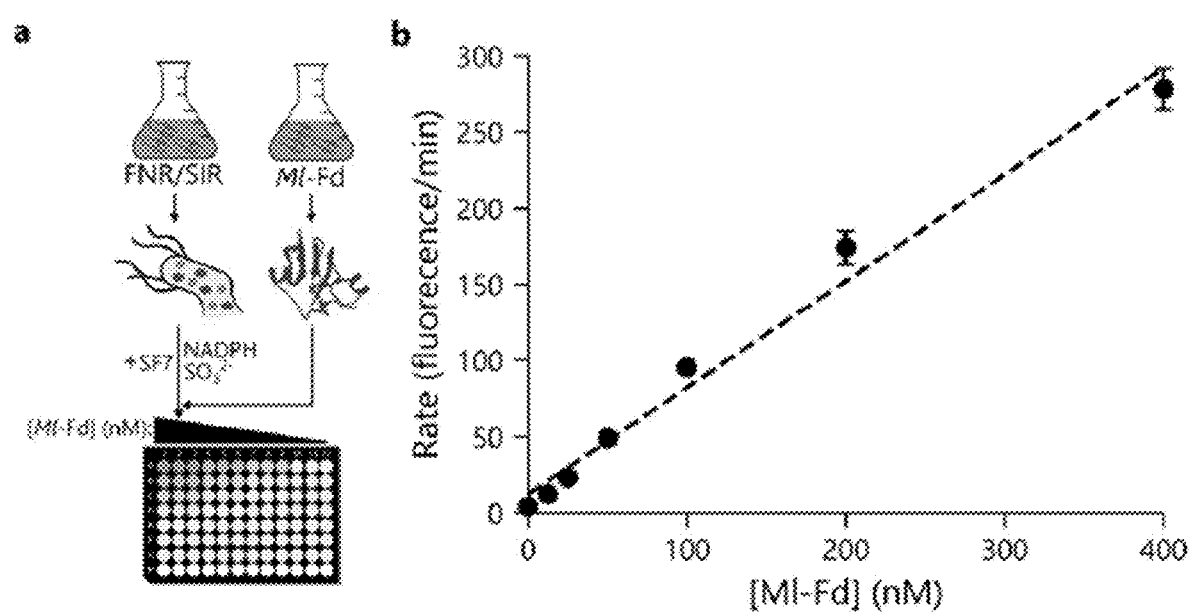
FIGS. 35A-B

REGULATING ELECTRON FLOW USING FRAGMENTED PROTEINS

REFERENCE TO RELATED APPLICATIONS

The present application claims the priority benefit of U.S. provisional application No. 62/583,770, filed Nov. 9, 2017, the entire contents of which is incorporated herein by reference.

STATEMENT REGARDING FEDERALLY SPONSORED RESEARCH

This invention was made with government support under Grant No. NNX15AL28G awarded by the National Aeronautics and Space Agency (NASA), Grant No. N00014-17-1-2639 awarded by the Office of Naval Research, and Grant No. DE-SC0014462 awarded by the Department of Energy. The government has certain rights in the invention.

BACKGROUND

1. Field

This disclosure relates generally to the fields of microbiology, cell biology, and biological sensing assays. More specifically, the disclosure relates to engineered microorganisms and their various uses, containing modified co-factor-containing protein electron carriers.

2. Description of Related Art

Electron transport (ET) driven by oxidative metabolism and photosynthesis is used for many purposes, including the production of membrane gradients for ATP synthesis, the synthesis of biological molecules, cellular communication, and the storage of energy by forming reduced chemicals. Life has evolved many means to mediate electron transfer ranging from small-molecule cofactors (e.g., nicotinamide adenine dinucleotides) to protein electron carriers (e.g., ferredoxins, flavodoxins, and cytochromes C). Achieving direct, dynamic control over biological ET through synthetic biology is critical for creating living sensors and bioelectronics (Jensen et al., 2010; Webster et al., 2014), controlling microbial electro-synthesis and -fermentation (Kracke et al., 2015), and building efficient metabolic pathways for chemical synthesis (Shomar et al., 2018; Kallio et al., 2014). At the hub of transferring low-potential electrons is the ferredoxin (Fd) family, ancient iron-sulfur (Fe—S) proteins that supported bioenergetics evolution (Sousa et al., 2013) and were tasked with the efficient apportionment of electron flow between a wide range of electron donor and acceptor proteins, including oxidoreductases that catalyze >75 reactions. These electron carriers are widespread, with some organisms containing over a dozen paralogs, and they have been found to support ET over eighty classes of oxidoreductases (Atkinson et al., 2016).

Electron carriers can be manipulated to control the production of reduced biomolecules. One of the most ancient electron carrier families is the iron-sulfur cluster containing ferredoxins (Fds), which use Fe—S clusters to shuttle electrons among diverse partner proteins. The Fe—S clusters in Fd serve as an electron redox hub accepting electrons from diverse protein donors and donating electrons to diverse metabolic pathways. Fds are unique in their ability to control electron transfer at low (very negative) midpoint potentials.

To divert energy flow to specific partner proteins, Fds have been rationally mutated using structural information and fused to electron acceptor proteins. Additionally, Fds have been used to construct synthetic electron transfer chains that complement the growth of an auxotroph by producing a reduced product. These pathways have been developed to evolve Fd-dependent enzymes with improved catalytic functions (Barstow et al., 2011) and to understand Fd-partner specificity (Yang et al., 2017). These efforts have demonstrated the potential for manipulating protein electron carriers in metabolic engineering and synthetic biology.

At present, however, there is a lack of simple strategies to rapidly and directly turn Fd electron flow "on" and "off" in response to environmental conditions, similar to that observed with the nitrogenase-protecting Fds, which use oxidation to change their conformation and regulate nitrogenase. Currently the only way to control electron flow through these proteins is to vary the promoter that is used to express them. Improved methods for controlling and measuring electron flow in cells, including those that take advantage of low midpoint potential of Fds, would be of considerable value.

SUMMARY

To allow for dynamic, protein-level control over energy flow in metabolic systems for synthetic biology and bioelectronics, ferredoxin logic gates are provided that use transcriptional and post-transcriptional inputs to control energy flow through a synthetic electron transfer pathway. For example, an allosteric ferredoxin switch created through domain insertion acquires an oxygen-tolerant 2Fe-2S cluster and can use different chemicals to control the production of a reduced metabolite in *Escherichia coli* and cell lysates.

The inventors, in one aspect, have modified protein electron carriers (PECs) whose function can be regulated through transcriptional and post-translational mechanisms to control electron transfer between natural and non-natural biochemical pathways in cells. In one aspect, the present disclosure describes fragmentation of protein electron carriers and their fusion to proteins that assist with fragment complementation. These molecules, despite being cleaved from their natural form, retain the ability to acquire and bind metallo-complexes (inorganic iron-sulfur clusters) required for their function in electron transfer. The metallo-complexes remain stably bound in the presence of oxygen. It is in fact quite surprising that the clusters remain bound in the presence of oxygen, making these types of protein switches useful for many more applications than the ferredoxins that are sensitive to oxygen. In contrast, native 4Fe4S clusters fall off the proteins in the presence of oxygen, such as when one purifies some of the other family members.

Electron flow is an important consideration when engineering metabolism for the microbial production of high value chemicals (fuels, alcohols, saturated hydrocarbons, chiral bioactive molecules, and pharmaceutical compounds), because the amount and timing of electron transfer between different donor and acceptor proteins determines the ratio of biomass accumulation versus chemical production. The present methods can be used to improve control over the production of high-value chemicals by fine tuning redox levels by virtue of the fine control the inventors now show with fragmented PECs. Cell free systems are also contemplated to be useful in employing the technology described herein.

Electron flow across cellular membranes occurs in nature when cells require electron sources and sinks outside the cell for their metabolism and is important for many biotechnological applications, including microbial fuel cells and connecting microbes to electrical sources and sinks for the production of high-value chemicals and biosensing. The methods described herein can be used to improve control over electron flow into and out of cells for biosensing applications, such as by employing molecules that permit conditional of functional electron transporting complexes.

Fragmented protein electron carriers will allow for the construction of "energy conserving" metabolic pathways in organisms being engineered for green chemical production, they will offer a platform for developing biosensors that generate an electrical signal as an output upon sensing environmental conditions, and they will enable control over electron flow into cells. For example, generated "electric signal" can be converted to a number of outputs, such as (1) cell growth, (2) color or visual output (3) fluorescence or another type of visual output, (4) electricity read-out using an electrode, (5) a reduced chemical (e.g., sulfide) that can be detected using an electrode, or (6) altered behavior of another microbe that generates similar outputs.

Thus, in accordance with the present disclosure, there is provided an engineered cell comprising: a) a first nucleic acid segment encoding a first protein electron carrier (PEC) fragment, and b) a second nucleic acid segment encoding a second PEC fragment, wherein said first and second nucleic acid segments are under the transcriptional control of one or more promoters, and wherein said first and second fragments, when expressed, are capable of binding a cofactor necessary for electron transport by said PEC. The cofactor may be a small molecule or a biological macromolecule, such as a protein, a DNA molecule, an RNA molecule, a lipid, or any other cellular component. The first and second nucleic acid segments may be under the control of distinct promoters, such as where one or more of the promoters are inducible. The first and/or second nucleic acid segments may be located on an extrachromosomal vector. Alternatively, the first and/or second nucleic acid segments may be located in the engineered cell's chromosomal DNA. As such, the first and/or second nucleic acid segment may be positioned on the cell's chromosomal DNA by insertion.

The first nucleic acid segment may encode said first fragment fused to a first heterologous peptide or polypeptide, and said second nucleic acid segment may encode said second fragment fused to a second heterologous peptide or polypeptide, wherein said first and second heterologous peptides or polypeptides associate with each other and facilitate functional association of said first fragment and said second fragments. The first and second nucleic acid segments may be fused in a non-contiguous fashion to a third nucleic acid segment encoding a ligand-binding polypeptide that, when bound to said ligand, facilitates functional association of said first fragment and said second fragment. The first nucleic acid segment may encode said first fragment fused to a first heterologous peptide or polypeptide, and said second nucleic acid segment may encode said second fragment fused to a second heterologous peptide or polypeptide, wherein said first and second peptides or polypeptides form a ternary complex in the presence of ternary complex forming agent, thereby facilitating functional association of said first fragment and said second fragment.

Also provided is a use of the cells described as a biosensor for said ligand, where the activity of active PEC is measured and correlates with a level of said ligand in said cell, or a use of the cells described above as a biosensor for said ternary complex forming agent member, where the activity of PEC is measured and correlates with a level of said ternary complex binding agent in said cell.

In another embodiment, there is provided an expression vector comprising a) a first nucleic acid segment encoding a first protein electron carrier (PEC) fragment, and b) a second nucleic acid segment encoding a second PEC fragment, wherein said first and second nucleic acid segments are under the transcriptional control of one or more promoters, wherein said first and second fragments, when expressed, are capable of binding a cofactor necessary for electron transport by said PEC. The first and second nucleic acid segments may be under the control of distinct promoters, such as where one or more promoters are inducible.

The first nucleic acid segment may encode said first fragment fused to a first heterologous peptide or polypeptide, and said second nucleic acid segment may encode said second fragment fused to a second heterologous peptide or polypeptide, wherein said first and second heterologous peptides or polypeptides associate with each other and facilitate functional association of said first fragment and said second fragments. The first and second nucleic acid segments may be fused in a non-contiguous fashion to a third nucleic acid segment encoding a ligand-binding polypeptide that, when bound to said ligand, facilitates functional association of said first fragment and said second fragment. The first nucleic acid segment may encode said first fragment fused to a first heterologous peptide or polypeptide, and said second nucleic acid segment may encode said second fragment fused to a second heterologous peptide or polypeptide, wherein said first and second peptides or polypeptides form a ternary complex in the presence of ternary complex forming agent, thereby facilitating functional association of said first fragment and said second fragment.

Also provided is an active protein electron carrier (PEC) produced by expression of the expression vectors described above. Also provided is an active protein electron carrier (PEC) produced by culturing of the cells as described above.

In yet a further embodiment, there is provided a method of assessing activity of a protein electron carrier (PEC) comprising a) providing a first PEC fragment and a second PEC fragment, wherein said first and second fragments, when associated, are capable of binding a cofactor necessary for electron transport by said PEC; b) subjecting said first and second PEC fragments to conditions permitting their association; and c) measuring electron transport by said PEC. The conditions permitting association may be i) physical association of said first and second PEC fragments by fragment-fused first and second heterologous peptides or polypeptides that drive self-assembly of a functional PEC; ii) binding of a ligand that induces a conformational change in a polypeptide to which said first and second PEC fragments are fused in a non-contiguous fashion; or iii) binding of a ternary complex binding agent to first and second heterologous peptides fused to said first and second PEC fragments that induces binding.

The output signal may employ fluorescence, colorimetric, radioactivity, density or settling (flocculation), light emission, size, or refractivity, or other optical chromatographic or spectral methods such as mass spectrometry or NMR, Raman spectroscopy or similar methods or electroanalytical method such as potentiometry, voltammetry, amperometry, or coulometry (see FIG. 24). The method may be a cell free method, an in vitro method, or an in cyto method. The ligand or ternary complex binding agent may be a metabolite, a drug, a toxin, or a physical factor such as temperature, osmotic strength, pressure, pH, light intensity, a surface contact, electric field, or magnetic field. The method may be performed in a prokaryotic cell or a eukaryotic cell.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the disclosure, such as instructions for use, buffers, background mutations that do not affect the disclosure, and the like.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

(FIG. 16A) A cell lysate based assay for monitoring native Fd electron transfer using sulfidefluor-7. (FIG. 16B) Cell lysate based assay for monitoring the timescale of switching of the protein from FIG. 10. Note that FNR and SIR are expressed at higher levels than cellular assay to yield an in vitro signal.

(FIG. 25A) A synthetic ET pathway that couples NADPH oxidation to sulfide production. (FIG. 25B) This pathway only complements the growth of E. coli EW11 on minimal medium containing sulfate as the sulfur source when a Fd transfers electrons from FNR to SIR. The effect of varying concentrations of aTc (0.4, 0.8, 1.6, 3.1, 6.3, 12.5, and 25 ng/mL) on the growth of cells expressing Ml-Fd from an aTc-inducible PLtetO1 promoter and FNR and SIR from constitutive promoters. The red line represents no aTc, while solid lines and gray bars represents the average and standard deviation, calculated from three biological replicates. (FIG. 25C) Growth complementation observed after 24 hours with *Mastigocladus laminosus* (circle; k1/2=1.8 ng/mL aTc), *Zea mays* root (square; k1/2=2.5 ng/mL aTc), *Chlamydomonas reinhardtii* (triangle; k1/2=14.2 ng/mL aTc), *Spinacia oleracea* (upside down triangle; k1/2>250 ng/mL), and *Prochlorococcus phage* (diamond; k1/2>250 ng/mL) Fds. (FIG. 25D) The number of different amino acids observed at each residue position within a Fd multiple sequence alignment mapped onto Ml-Fd primary structure (top). The backbone fission sites used to generate sFds (red line) are compared with the number of intramolecular residue-residue contacts (n=0 to 10 displayed as proportionally-sized black circles) within the structure of Ml-Fd (PDB=1RFK), as well as intermolecular binding residues, including the cysteines that coordinate the 2Fe-2S cluster (yellow) and the residues that contact SIR20 (green) and FNR21 (purple). (FIG. 25E) Each pair of sFd fragments, Fdf1 and Fdf2 (blue) was expressed as a fusion to SYNZIP-17 (SZ17; orange) and SYNZIP-18 (SZ18; red), respectively. (FIG. 25F) Complementation of *E. coli* EW11 growth by Fdf1 and Fdf2 when fused to SZ17 and SZ18, SZ18, or no peptides. * represents p-values <0.01 using a two-tailed, independent t-test. (FIG. 25G) Genetic circuit used to regulate Fd fragment expression. Fdf1 is expressed using an aTc-inducible promoter, Fdf2 is expressed using an IPTG-inducible promoter, and the partner proteins are constitutively expressed. (FIG. 25H) Effects of sFd fragment concentration, controlled by aTc and IPTG, on *E. coli* EW11 complementation. Each box shows cell density from cultures (100 µL) measured for 48 hours with the growth rate (h-1) indicated by the color.

(FIG. 26A) sFd-35 fragments Fdf1 and Fdf2 (blue) were expressed as fusions to FKBP (orange) and FRB (red), respectively. (FIG. 26B) Effect of rapamycin concentration on *E. coli* EW11 growth in the presence of aTc (150 ng/mL) and IPTG (500 µM) concentrations that yielded strong complementation with SZ17/SZ18 fusions. Complementation by Fdf1-FRB/FKBP-Fdf2 (diamond; k1/2=9.95 µM rapamycin) is compared with Ml-Fd (circle) and a C42A mutant of Ml-Fd (square) that lacks a cysteine required for coordinating iron. Growth of cells expressing Fdf1-FRB/FKBP-Fdf2 is enhanced significantly above the C42A mutant (p-value <0.01 using a two-tailed, independent t-test) when ≥25 µM rapamycin is added. (FIG. 26C) The effect of rapamycin on the relative fluorescence ($\lambda$ex=560 nm, $\lambda$em=650 nm) of cells expressing Fdf1-FKBP-RFP (square) and FRB-Fdf2-RFP (diamond). Upon addition of rapamycin in ethanol, there was no significant increase in fluorescence for either fragment compared to ethanol alone (p-value >0.01 using a two-tailed, independent t-test). (FIG. 26D) Fdf1-FRB and FKBP-Fdf2 can function as a three-input AND gate that uses aTc, IPTG, and rapamycin to control electron flow. (FIG. 26E) The ER-LBD was inserted after residue 35 in Ml-Fd to create sFd-35-ER. (FIG. 26F) Effect of 4-HT concentration on the complementation of *E. coli* EW11 by sFd-35-ER (circle; k1/2=2.11 µM 4-HT), Ml-Fd (diamond), and Ml-Fd-C42A (square). Growth of sFd-35-ER is enhanced significantly above the C42A mutant (p-value <0.01 using a two-tailed, independent t-test) in the presence of ≥6.25 µM 4-HT. (FIG. 26G) The effect of 4-HT on the relative fluorescence of cells expressing sFd-35-ER-RFP. Upon addition of 4-HT in ethanol, there was no significant increase in fluorescence compared to ethanol alone (p-value >0.01 using a two-tailed, independent t-test).

All fluorescent reporters were amended to the C-terminus of proteins to maintain the context of the ribosomal binding sites and translation initiation (Salis et al., 2009).

FIGS. 27A-E. Using purified recombinant sFd-35-ER to control metabolite production in cell lysates. (FIG. 27A) The absorbance and (FIG. 27B) circular dichroism spectra of purified sFd-35-ER and Ml-Fd (150 µM each) in and presence (solid line) or absence (dashed line) of 4-HT display features characteristic of 2Fe-2S proteins (Ta & Vickery, 1992). (FIG. 27C) The midpoint potentials of Ml-Fd and sFd-35-ER in and presence (solid line) or absence (dashed line) of 4-HT. Raw square wave voltammetry data are plotted in gray, baseline-subtracted data are plotted in black. (FIG. 27D) Desalted lysates generated from *E. coli* EW11 constitutively expressing FNR and SIR were mixed with purified sFd-35-ER (50 nM), NADPH (40 µM), $SO_3^{2-}$ (10 mM), and sulfidefluor-7 (2 µM). Following mixing, 4-HT in ethanol (line) or an equivalent amount of ethanol (dashed line) were added to reactions, and fluorescence ($\lambda$ex=495 nm, $\lambda$em=520 nm) was monitored at 37° C. (FIG. 27E) The sFd-35-ER switch displayed a significant increase in sulfide production rate upon 4-HT addition (p=0.027, using a two-tailed, independent t-test) relative to the ethanol carrier.

Figure 28:
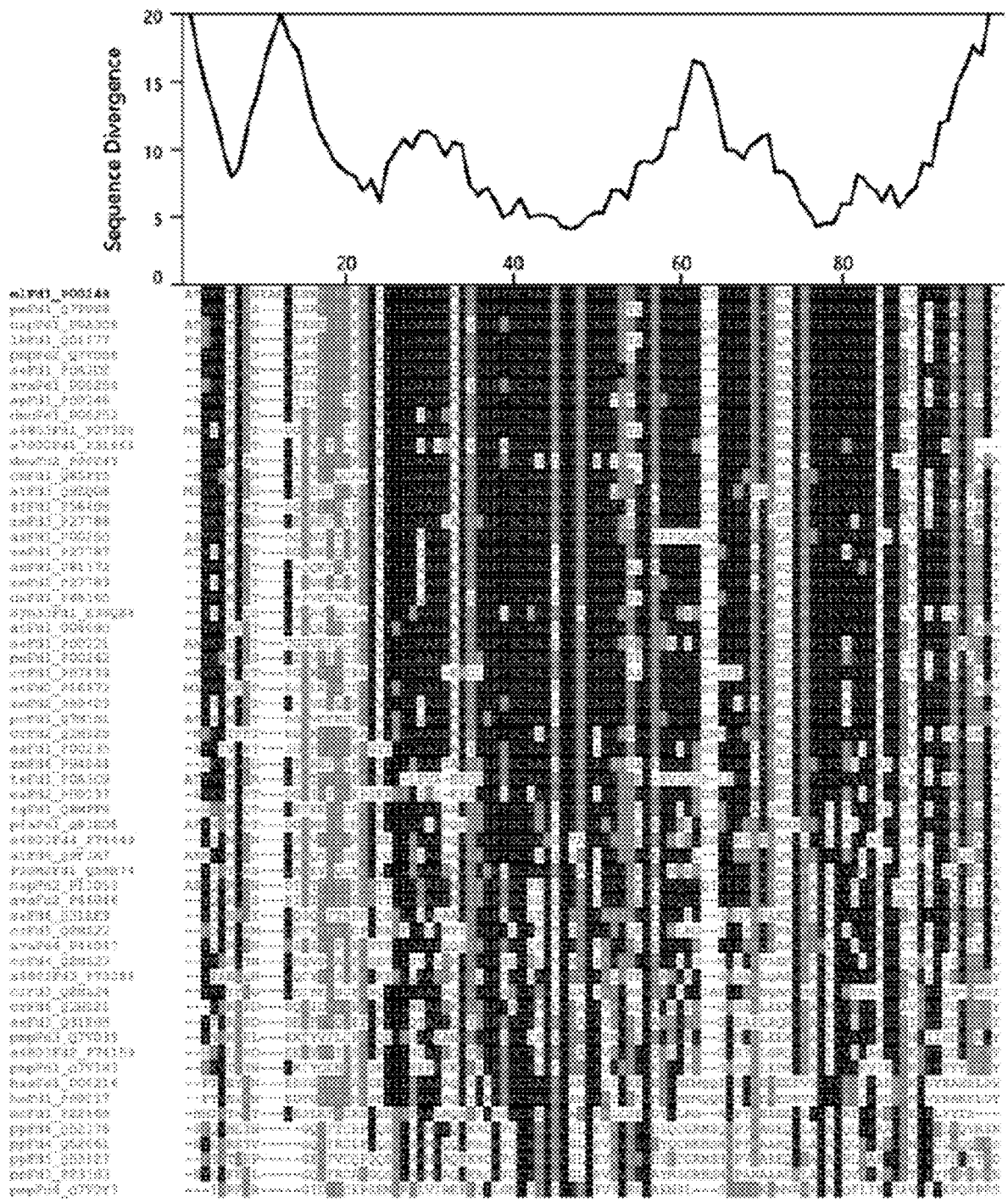

FIG. 28. (Top) The Fd family sequence divergence profile from FIG. 25B. (Bottom) A multiple sequence alignment (MSA) of 60 plant-type Fds (Table 3) that was pruned to show only residues aligning with Ml-Fd (bolded). Positions within the MSA containing insertions or less conserved regions in the protein family display higher sequence divergence values. Residue positions conserved across ≥50% of the sequences in the MSA are highlighted in black if identical and grey if similar amino acids. Fds are listed by their UniProt accession numbers. Each Fd, listed from top to bottom, has a SEQ ID NO as follows: mlFd1_P00248 is SEQ ID NO: 11; pmFd1_Q7TUS8 is SEQ ID NO: 44; nspFd1_P0A3C8 is SEQ ID NO: 3; lbFd1_Q51577 is SEQ ID NO: 18; pmpFd2_Q7V0B6 is SEQ ID NO: 45; seFd1_P0A3D2 is SEQ ID NO: 47; avaFd1_P00254 is SEQ ID NO: 48; apFd1_P00246 is SEQ ID NO: 19; dmuFd1_P00252 is SEQ ID NO: 46; s6803Fd1_P27320 is SEQ ID NO: 9; s7002Fd1_P31965 is SEQ ID NO: 43; dmuFd2_P00249 is SEQ ID NO: 42; cmFd1_Q85FT5 is SEQ ID NO: 15; atFd3_Q9ZQG8 is SEQ ID NO: 39; sfFd1_P56408 is SEQ ID NO: 2; zmFd3_P27788 is SEQ ID NO: 40; asFd1_P00250 is SEQ ID NO: 16; zmFd1_P27787 is SEQ ID NO: 17; amFd1_P81372 is SEQ ID NO: 50; zmFd5_P27789 is SEQ ID NO: 52; dsFd1_P68165 is SEQ ID NO: 49; Syn33Fd1_E3SQZ8 is SEQ ID NO: 37; atFd1_004090 is SEQ ID NO: 51; soFd1_P00221 is SEQ ID NO: 1; puFd1_P00242 is SEQ ID NO: 38; crFd1_P07839 is SEQ ID NO: 14; atFd2_P16972 is SEQ ID NO: 21; zmFd2_O80429 is SEQ ID NO: 53; pcFd1_Q7M1S1 is SEQ ID NO: 10; crFd2_Q2HZ25 is SEQ ID NO: 20; eaFd1_P00235 is SEQ ID NO: 7; zmFd6_P94044 is SEQ ID NO: 41; teFd1_P0A3C9 is SEQ ID NO: 12; eaFd2_P00237 is SEQ ID NO: 13; tgFd1_Q8MPF8 is SEQ ID NO: 33; pfaFd1_Q8IED5 is SEQ ID NO: 8; s6803Fd4_P74449 is SEQ ID NO: 31; atFd4_Q9FIA7 is SEQ ID NO: 32; PSSM2Fd1_Q58M74 is SEQ ID NO: 36; nspFd2_P11053 is SEQ ID NO: 6; avaFd2_P46046 is SEQ ID NO: 34; seFd6_Q31RE9 is SEQ ID NO: 55; crFd5_Q2HZ22 is SEQ ID NO: 29; avaFd4_P46047 is SEQ ID NO: 35; crFd4_Q2HZ23 is SEQ ID NO: 30; s6803Fd3_P73388 is SEQ ID NO: 56; crFd3_Q2HZ24 is SEQ ID NO: 28; crFd6_Q2HZ21 is SEQ ID NO: 57; seFd3_Q31K08 is SEQ ID NO: 59; pmpFd3_Q7V039 is SEQ ID NO: 54; s6803Fd2_P74159 is SEQ ID NO: 60; pmpFd1_Q7V1H3 is SEQ ID NO: 58; hasFd1_P00216 is SEQ ID NO: 5; hmFd1_P00217 is SEQ ID NO: 4; mcFd1_P22868 is SEQ ID NO: 27; ppFd6_Q52176 is SEQ ID NO: 25; ppFd4_Q52061 is SEQ ID NO: 26; ppFd5_Q53527 is SEQ ID NO: 23; ppFd3_P23103 is SEQ ID NO: 24; and pmpFd4_Q7V2Y3 is SEQ ID NO: 22.

Figure 29:
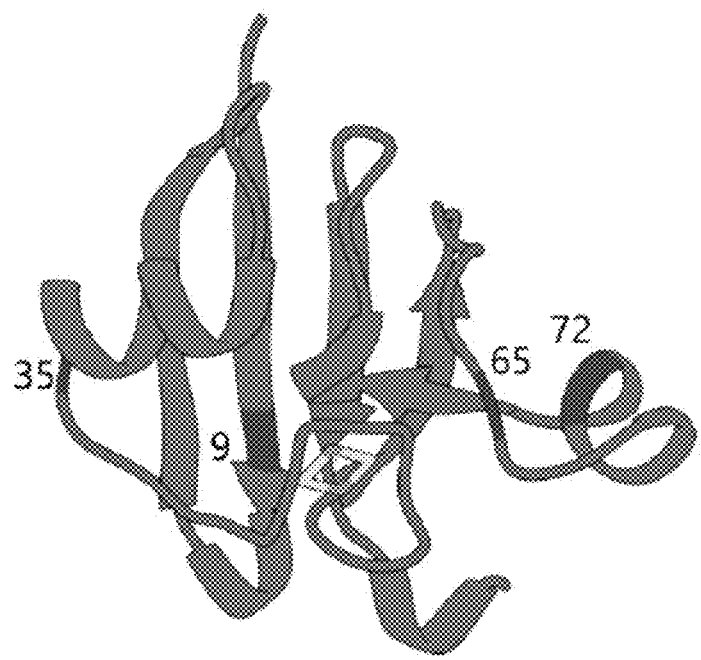

FIG. 29. Structural relationship between backbone cleavage sites and 2Fe2S cluster. The backbone cleavage sites (red) relative to the iron (orange) and sulfur (yellow) in the 2Fe2S within the WT Ml-Fd structure (PDB: 1RFK). The backbone fragmentation site following residue 35 is most distal from the 2Fe2S cluster (18.5 Å), while the backbone cleavage sites following residue 9 (18.2 Å), residue 71 (14.3 Å), and residue 65 (9.5 Å) are more proximal.

Figure 30:
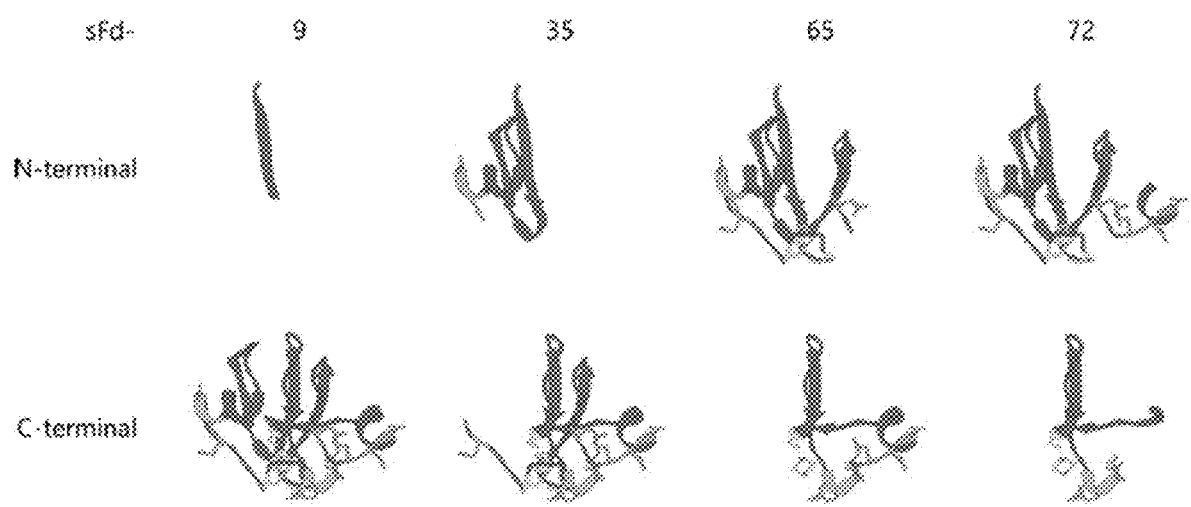

FIG. 30. Structural relationship between backbone cleavage sites and intermolecular binding residues. WT Ml-Fd structure (PDB: 1RFK) with highlighted residues important for intermolecular binding to the 2Fe2S cluster are shown in yellow, the FNR-binding residues are shown in purple, and the SIR-binding residues are shown in green. Backbone cleavage following different native residues in Ml-Fd (9, 35, 65, and 72) results in fragments containing residues for binding zero, one or three of the intermolecular interfaces.

FIGS. 31A-B. Genetic circuits used to express chemical-dependent sFds. (FIG. 31A) A two-input transcriptional circuit uses TetR (and aTc) to control expression of Fd fragment A (Fda) fused to FKBP and LacI (and IPTG) to control expression of FRB fused to Fd fragment B (Fdb). (FIG. 31B) To build a vector that expresses Fd-fragments fused to the ER LBD, the region contain fkbp-pLlacO1-frb was replaced with the gene encoding ER LBD. The resulting construct expresses a single polypeptide controlled using aTc/TetR.

FIGS. 32A-D. Purified recombinant sFd-35-ER. (FIG. 32A) The apo-ER-LBD crystal structure (PDB: 1A52) presents a large termini distance (~64 Å) because helix 12 (red) is distal from the ligand-binding pocket. (FIG. 32B) Agonist bound structures (17β-estradiol PDB: 1ERE in white and diethylstilbesterol PDB: 3ERD in grey) show helix 12 (red) moving to cap the ligand-binding pocket resulting in a shortened termini distance (dashed line) of ~33 Å, while (FIG. 32C) antagonist bound structures (4-hydroxytamoxifen PDB: 3ERT in grey and raloxifene PDB: 1ERR in dark grey) show helix 12 moving away from the ligand-binding pocket to cover the co-activator binding surface resulting in an even shorter termini distance of ~20 Å. (FIG. 32D) Effect of estrogen receptor modulators (50 µM) on complementation of E. coli EW11 by sFd-35-ER with 0 ng/mL aTc (white bars) or 200 ng/mL aTc (grey bars). The agonists (diethylstilbesterol, hexesterol, and 17β-estradiol) do not significantly enhance growth of EW11 cells compared to DMSO alone, while the antagonists (4-hydroxytamoxifen, raloxifene, and lasoxifene) as well as bisphenol-A significantly enhance growth compared to DMSO alone. * represents p-values <0.01 using a two-tailed, independent t-test.

FIG. 33A-B. Purified recombinant sFd-35-ER. (FIG. 33A) sFd-35-ER bound to anion exchange resin during aerobic purification (DE52) is brown in color, typical of 2Fe2S containing proteins. Similar results were observed with Ml-Fd. (FIG. 33B) SDS-page gel of varying amounts of purified sFd-35-ER. The calculated molecular weight is 41 kDa.

FIGS. 34A-B. Sulfide production by cell lysates containing FNR and SIR. (FIG. 34A) Lysates derived from EW11 expressing FNR and SIR were generated, and (FIG. 34B) sulfide production was monitored by adding SF7 and monitoring fluorescence in the presence of varying amounts on of NADPH. Lysates displayed increasing rates of SF7 fluorescence with increasing concentrations of NADPH.

FIGS. 35A-B. Using cell lysates to monitor Ml-Fd electron transfer from FNR to SIR. (FIG. 35A) Lysates of EW11 expressing FNR and SIR were generated and mixed with purified Ml-Fd, substrates NADPH and $SO_2^{3-}$ and sulfide production was monitored using SF7 fluorescence. (FIG. 35B) Lysates displayed a linearly increasing rate (y=0.7×+ 12.252, $r^2$=0.983) of SF7 fluorescence with increasing concentrations of Ml-Fd.

DETAILED DESCRIPTION

Figure 1:
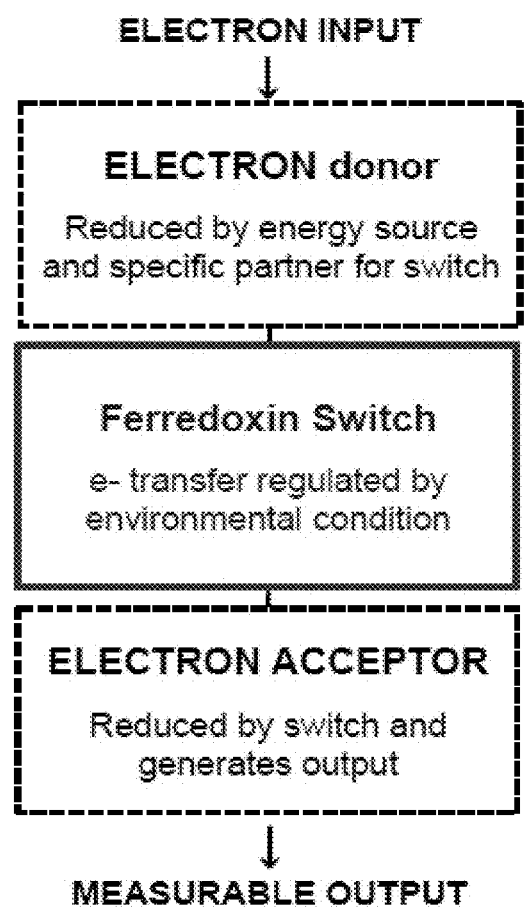
FIG. 1. Context for using protein e-switches.
Figure 2:
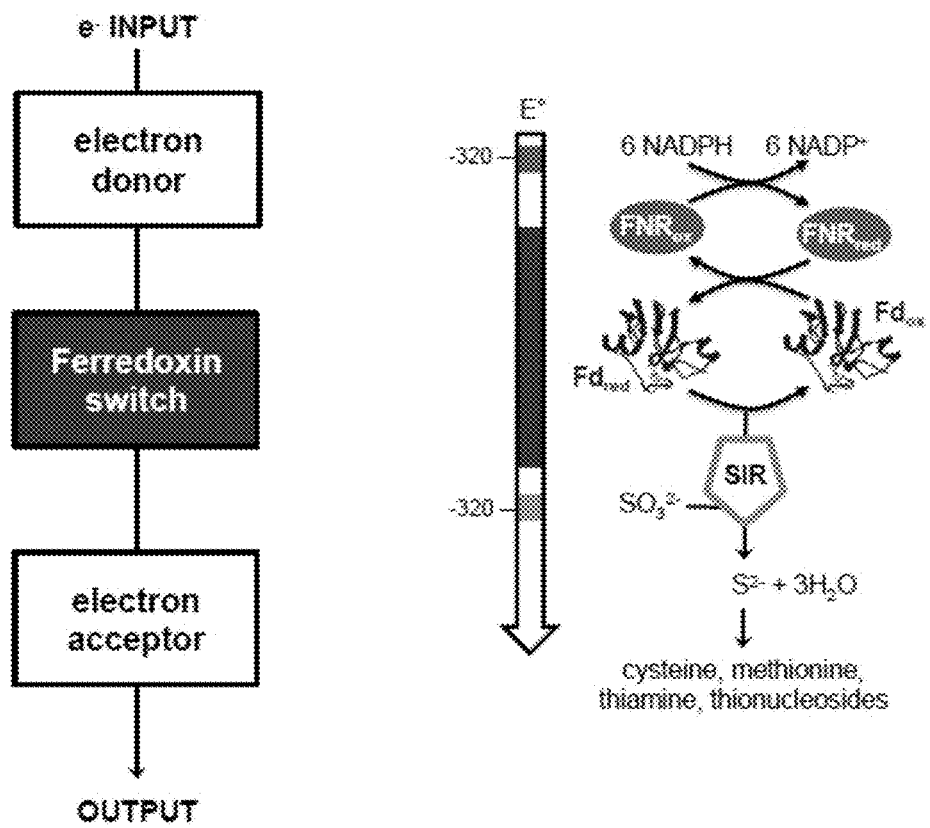
FIG. 2. Cellular read-out for switch function. One example uses E. coli EW11, which is a sulfide auxotroph. This strain cannot be grown on sulfite as a sulfur source unless ferredoxin transfers electrons.
Figure 3:
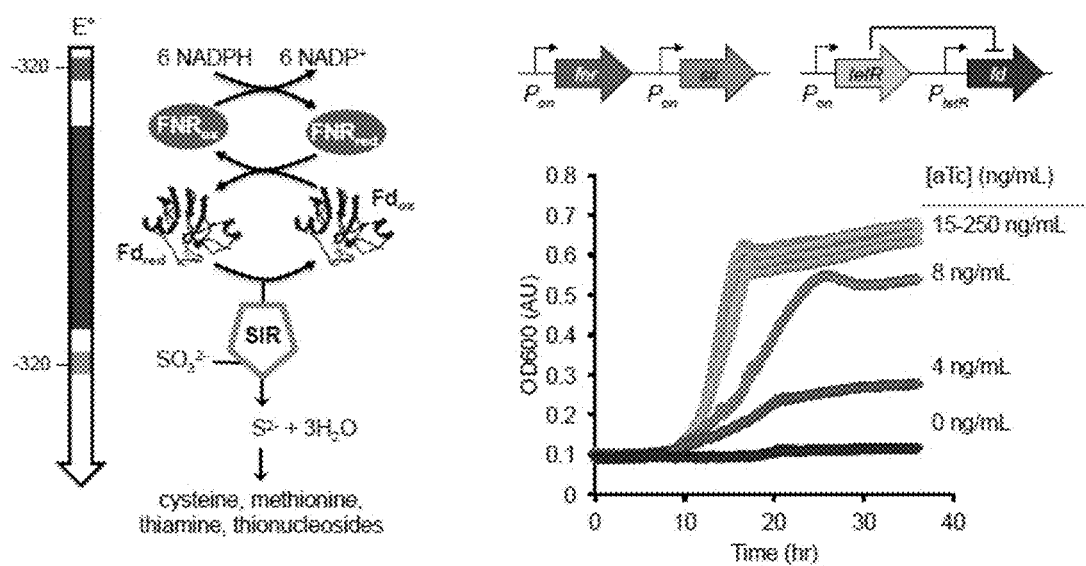
FIG. 3. Cellular read-out for switch function. Data using the system shown in FIG. 2 under aerobic conditions.

FIG. 1 shows the general approach taken by the inventors to design and test systems including biological electron "switches." While exemplified using ferredoxins, a wide variety of protein electron carrier (PEC) molecules can be employed once the operating parameters are established. FIGS. 2-3 show particular examples of how electron flow can be regulated in biological systems with such switches.

The inventors here have used several approaches, described below, to address the challenge of developing rapid biological sensing molecules. One approach involves using transcriptional control over two promoters expressing two fragments of a PEC that self-assemble due to the presence of "helper" domains that have been fused to the fragments, thereby forming an active PEC. Another type of post-translational control employs binding of fragmented fusion peptides to each other and/or to ligands or to a third member of a ternary binding complex, which binding can be regulated and controlled, i.e., can act as a biological "switch" that turns electron flow on an off.

Chemical-dependent protein electron carriers represent a new class of synthetic switches that will enable precision control over electron flow. Such redox protein switches can be used in place of native oxidoreductases to regulate the flow of electron derived from oxidative metabolism and photosynthesis in response to specific metabolic or environmental cues, and they can be used to dynamically regulate electron flow between central metabolism and non-native metabolic pathways (Shomar et al., 2018; Kallio et al., 2014; Barstow et al., 2011; Rumpel et al., 2014; Eilenberg et al., 2016). Furthermore, redox protein switches should be useful for coupling the exquisite sensing capabilities of proteins to electrical communication between cells and conductive materials outside of cells (Jensen et al., 2010). To date, electron conduits have been described whose extracellular ET can be tuned using transcriptional regulation (Webster et al., 2014). By coupling exoelectrogen current production to redox protein switches, post-translational control over cellular current production may be possible that does not require slow transcriptional and translational processes. In the future, the ligand specificity of these switches can be diversified by fusing Fd fragments to different ligand-binding domains and by mutating the ligand-binding site of the prototype switches. Additionally, the design approach can be applied to other families of protein electron carriers (e.g., Fds with 4Fe-4S clusters, flavodoxins, and cytochromes) (Atkinson et al., 2016) to expand the classes of cellular reactions that can be regulated by controlling electron flow through protein carriers.

I. PROTEIN ELECTRON CARRIERS

The inventors have developed first in class reagents that can be employed in a wide variety of methods and systems described throughout this document. The molecules are protein electron carriers such as ferredoxins, flavodoxins, cytochromes and others that have been engineered to work as "switches" that can control electron flow based on external manipulation or environmental signals. The following is a general discussion of one of these types of molecules, ferredoxins (Fds).

A. Ferredoxins

Ferredoxins are iron-sulfur proteins that mediate electron transfer in a range of metabolic reactions; indeed, iron-sulfur clusters are relatively ubiquitous in nature. The term "ferredoxin" was coined by D. C. Wharton of the DuPont Co. and applied to the "iron protein" first purified in 1962 by Mortenson, Valentine, and Carnahan from the anaerobic bacterium *Clostridium pasteurianum*. Ferredoxins are found in prokaryotes, eukaryotes, and archaea, emphasizing the relative ease that with which these molecules should be employed in a wide variety of applications.

Another redox protein, isolated from spinach chloroplasts, was termed "chloroplast ferredoxin". The chloroplast ferredoxin is involved in both cyclic and non-cyclic photophosphorylation reactions of photosynthesis. In non-cyclic photophosphorylation, ferredoxin is the last electron acceptor thus reducing the enzyme $NADP^+$ reductase. It accepts electrons produced from sunlight-excited chlorophyll and transfers them to the enzyme ferredoxin:$NADP^+$ oxidoreductase.

Other bioinorganic electron transport systems include rubredoxins, cytochromes, blue copper proteins, and the Rieske proteins.

Ferredoxins are small proteins containing iron and sulfur atoms organized as iron-sulfur clusters. These biological "capacitors" can accept or discharge electrons, with the effect of a change in the oxidation state of the iron atoms between +2 and +3. In this way, ferredoxin acts as an electron transfer agent in biological redox reactions.

Ferredoxins can be classified according to the nature of their iron-sulfur clusters and by sequence similarity.

$Fe_2S_2$ ferredoxins have a general core structure consisting of beta(2)-alpha-beta(2), which includes putidaredoxin, terpredoxin, and adrenodoxin. They are proteins of around one hundred amino acids with four conserved cysteine residues to which the 2Fe-2S cluster is ligated. This conserved region is also found as a domain in various metabolic enzymes and in multidomain proteins, such as aldehyde oxidoreductase (N-terminal), xanthine oxidase (N-terminal), phthalate dioxygenase reductase (C-terminal), succinate dehydrogenase iron-sulphur protein (N-terminal), and methane monooxygenase reductase (N-terminal).

One group of ferredoxins, originally found in chloroplast membranes, has been termed "chloroplast-type" or "plant-type". Its active center is a $[Fe_2S_2]$ cluster, where the iron atoms are tetrahedrally coordinated both by inorganic sulfur atoms and by sulfurs of four conserved cysteine (Cys) residues. In chloroplasts, $Fe_2S_2$ ferredoxins function as electron carriers in the photosynthetic electron transport chain and as electron donors to various cellular proteins, such as glutamate synthase, nitrite reductase and sulfite reductase. In hydroxylating bacterial dioxygenase systems, they serve as intermediate electron-transfer carriers between reductase flavoproteins and oxygenase.

Adrenodoxin (adrenal ferredoxin) is expressed in mammals including humans. The human variant of adrenodoxin is referred to as ferredoxin 1. Adrenodoxin, putidaredoxin, and terpredoxin are soluble $Fe_2S_2$ proteins that act as single electron carriers. In mitochondrial monooxygenase systems, adrenodoxin transfers an electron from NADPH:adrenodoxin reductase to membrane-bound cytochrome P450. In bacteria, putidaredoxin and terpredoxin serve as electron carriers between corresponding NADH-dependent ferredoxin reductases and soluble P450s. The exact functions of other members of this family are not known, although *Escherichia coli* Fdx is shown to be involved in biogenesis of Fe—S clusters. Despite low sequence similarity between adrenodoxin-type and plant-type ferredoxins, the two classes have a similar folding topology.

Ferredoxin-1 in humans participates in the synthesis of thyroid hormones. It also transfers electrons from adrenodoxin reductase to the cholesterol side chain cleavage cytochrome P450. FDX-1 has the capability to bind to metals and proteins. It can be found within the cellular mitochondrial matrix.

The $Fe_4S_4$ ferredoxins may be further subdivided into low-potential (bacterial-type) and high-potential (HiPIP) ferredoxins. The formal oxidation numbers of the iron ions can be $2Fe^{3+},2Fe^{2+}$ or $1Fe^{3+},3Fe^{2+}$ in low-potential ferredoxins. The oxidation numbers of the iron ions in high-potential ferredoxins can be $3Fe^{3+},1Fe^{2+}$ or $2Fe^{3+},2Fe^{2+}$.

A group of $Fe_4S_4$ ferredoxins, originally found in bacteria, has been termed "bacterial-type". Bacterial-type ferredoxins may in turn be subdivided into further groups, based on their sequence properties. Most contain at least one conserved domain, including four cysteine residues that bind to a $Fe_4S_4$ cluster. In *Pyrococcus furiosus* $Fe_4S_4$ ferredoxin, one of the conserved Cys residues is substituted with aspartic acid.

The 7Fe ferredoxins contain both 4Fe-4S and 3Fe-4S centers. The 4Fe-4S domain is similar to those found in other bacterial-type ferredoxins. The 3D structure of the 7Fe ferredoxin from *Azotobacter vinelandii* has been determined to 1.9 Å resolution. The fold belongs to the alpha+beta class, with 3 helices and 4 strands forming a barrel-like structure, and an extruded loop containing 3 of the 4 cysteinyl residues of the iron-sulphur cluster.

During the evolution of bacterial-type ferredoxins, intrasequence gene duplication, transposition and fusion events occurred, resulting in the appearance of proteins with multiple iron-sulfur centers. In some bacterial ferredoxins, one of the duplicated domains has lost one or more of the four conserved Cys residues. These domains have either lost their iron-sulfur binding property or bind to a $Fe_3S_4$ cluster instead of a $Fe_4S_4$ cluster and dicluster-type.

3-D structures are known for a number of monocluster and dicluster bacterial-type ferredoxins. The fold belongs to the α+β class, with 2-7 α-helices and four β-strands forming a barrel-like structure, and an extruded loop containing three "proximal" Cys ligands of the iron-sulfur cluster.

High-potential iron-sulfur proteins (HiPIPs) form a unique family of $Fe_4S_4$ ferredoxins that function in anaerobic electron transport chains. Some HiPIPs have a redox potential higher than any other known iron-sulfur protein (e.g., HiPIP from *Rhodopila globiformis* has a redox potential of ca. 450 mV). Several HiPIPs have so far been characterized structurally, their folds belonging to the α+β class. As in other bacterial ferredoxins, the $[Fe_4S_4]$ unit forms a cubane-type cluster and is ligated to the protein via four Cys residues.

Linking to any of the accession numbers at InterPro (IPR) will provide additional links to several species of each type of ferredoxin, including those that are thermostable. Exemplary ferredoxins include *Mastigocladus laminosus* ferredoxin P00248 (EC 3.10.20.30), P27320, L8AP52, P00243, A0A068MS32, K9VVC8, A6MW30, UPI0002AC6EB7, P00247, K9QBV6. Others can be found by BLAST, by EC search, etc. Another 140 more are listed at Uniprot as having 50% homology to P00248.

B. Split PECs

The inventors have undertaken an analysis of a $2Fe_2S$ ferredoxin to determine whether this molecule can be split into two components that, once brought back together, can perform electron transfer in the same fashion and the normal intact molecule. A key question that had to be first answered was whether it was possible to retain metal cofactor binding in one of the split fragments while nonetheless abrogating electron transfer function. The inventors were able to determine that it was in fact possible to do just that, and they have identified several points within the tested ferredoxin at which break can be introduced that (a) prevents electron transfers but (b) does not prevent metal cofactor binding. This permits reconstitution of the two fragments into a functional unit by employing the approaches discussed below.

To identify backbone fission locations that are non-disruptive to Fd electron transfer, an alignment of diverse plant-type Fds was generated and the number of different amino acids observed at each position was quantified. Four sites were chosen for fission that were in regions that displayed sequence variation within the protein family, including following the peptide bond after residues 9, 35, 65, and 72. In the structure of this Fd, these backbone cleavage sites range in distance between 9.5 to 18.5 Å from the $2Fe_2S$ cluster. With two of the split Fd (sFd) proteins, sFd-9 and sFd-35, all of the cysteines that coordinate iron reside on a single polypeptide. The other two sFds, sFd-65 and sFd-72, have iron-binding cysteines spread across the two polypeptide fragments.

II. TRANSCRIPTIONAL CONTROL

In one embodiment, the inventors envision the use of two-promoter regulation to drive expression of two complementing halves of a PEC. The coding regions for the two PEC fragments can be coupled to virtually any useful promoter pair. For example, if it is desired to switch on electron flow under specific environmental conditions, one can regulate PEC expression, and hence activity, by coupling fragment expression to promoters that are active when a particular environmental stimulus is present. For example, if the stimulus triggers activity of a metabolic pathway, e.g., promoters that are active in the pathway can be used (for example, a particular carbon source). In this way, PEC expression in response to the stimulus would allow electron flow when the promoters are activated, and then halt e-flow when at least one of those two promoters are not active, i.e., effectively functioning as a "kill switch" in a given cell within a population. While a full length PEC can be coupled to one condition (i.e., one promoter), this affords more limited genetic control than a PEC that can be coupled to two conditions (and thus more spatial and temporal control), which provides a more robust read-out of the conditions under which the cell is placed.

Figure 5:
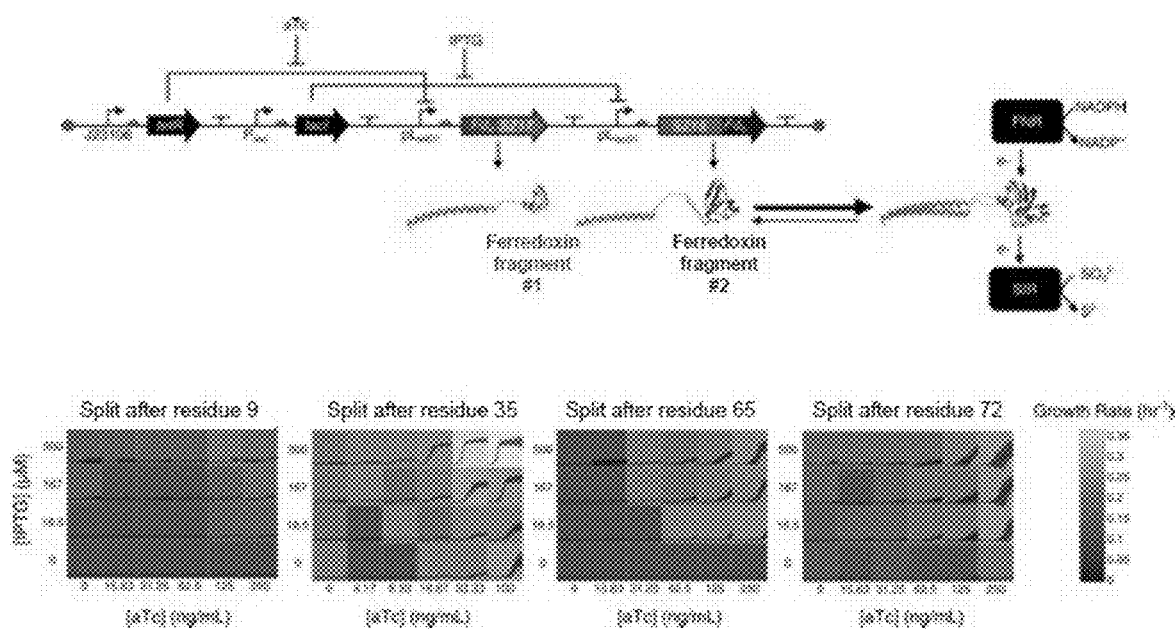
FIG. 5. Switch type #1. Fragments of PEC are fused to SYNZIP17 and SYNZIP18, which are self-associating peptides.
Figure 6:
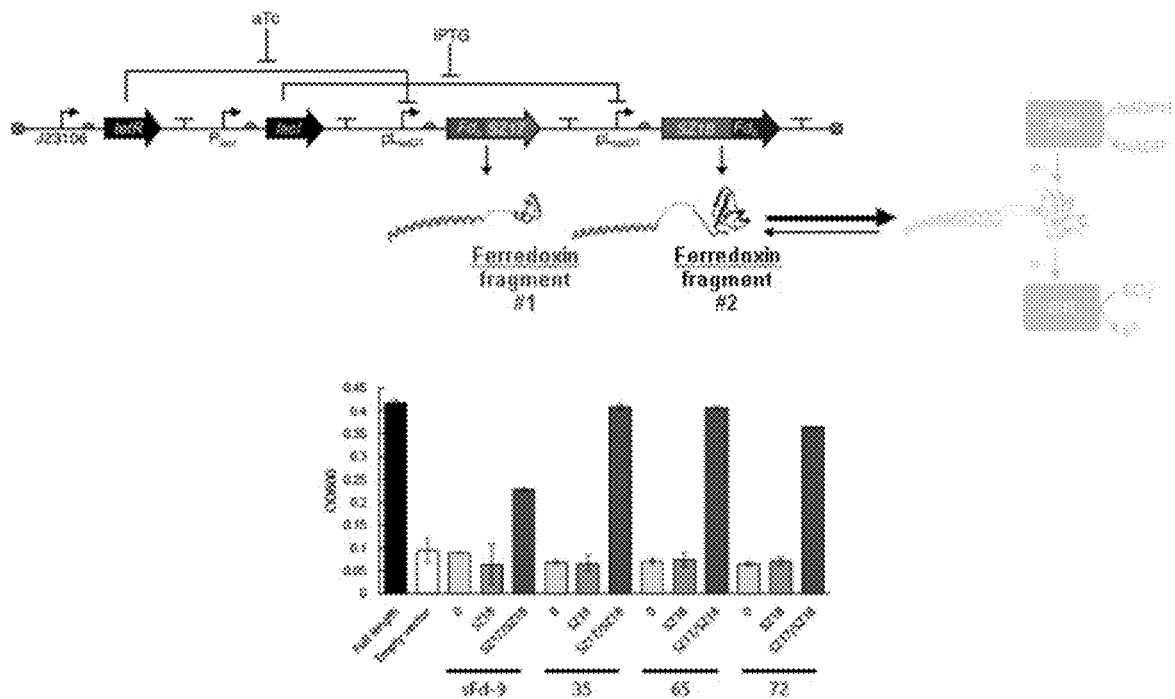
FIG. 6. Switch type #1. Removal of SYNZIP17 peptide leads to loss function showing that fragments of PEC require assistance to create a functional complex.

It should be noted that once cleaved, the PEC will need assistance in reassembling. This can be achieved using self-assembly peptides, of which there are numerous examples, including the SYNZIP peptides from Thompson (2012), which is incorporated by reference herein in its entirety. The inventors have employed the SYNZIP17 and SYNZIP18 peptides, and have demonstrated their functionality in this sort of system (see FIGS. 5-6). Other examples include SYNZIP 1 and 2, which pair together, as do SYN-ZIPS and 6, associating peptides IAAL-E3 and IAAL-K3, proteins CheA and CheY, E/K coils.

III. POST-TRANSLATIONAL CONTROL

The inventors have designed and introduced multiple new PECs whose activities can be switched on and off in response to various post-translational inputs. Using a post-translation method like the ones described below can allow for control of metabolism as well as for controlling electron flow into and out of cells for biosensing applications. This constitutes a marked improvement over current methods that require coupling of an intact PEC to transcriptional regulation under the control of an induced promoter.

Figure 23:
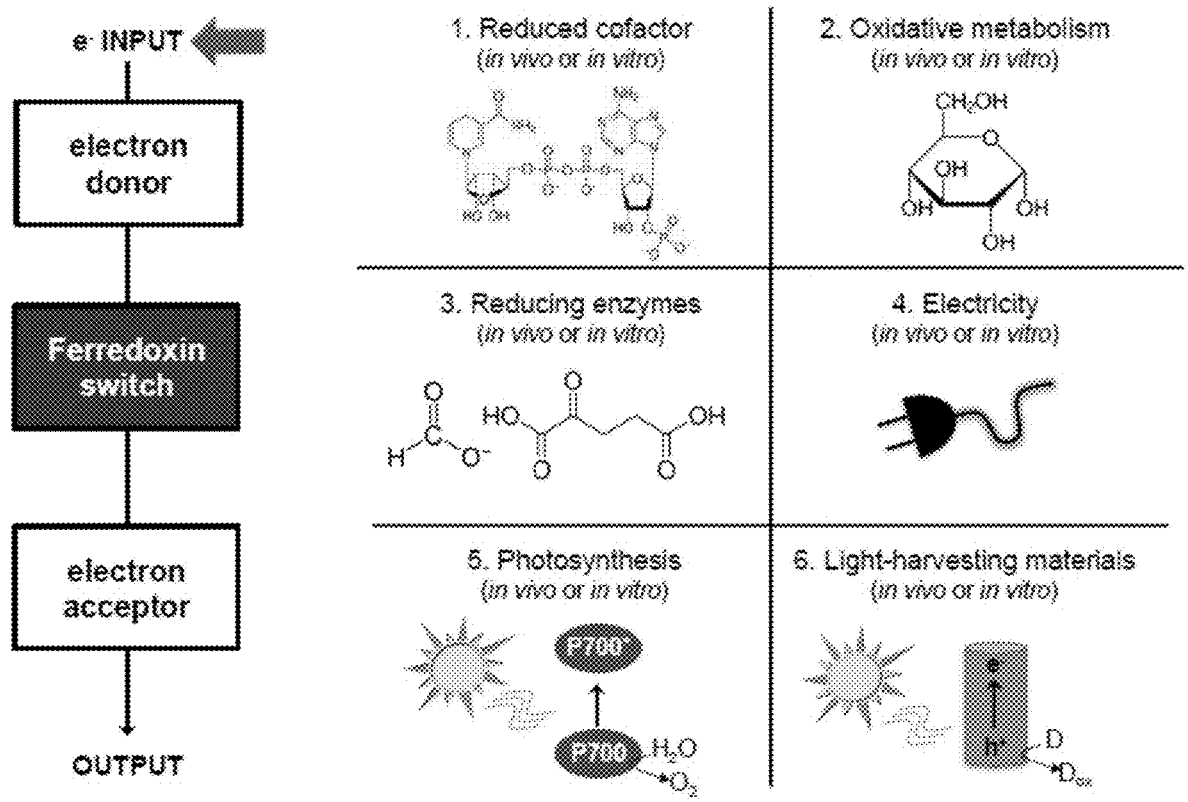
FIG. 23. Electron sources that can be used as inputs.
Figure 24:
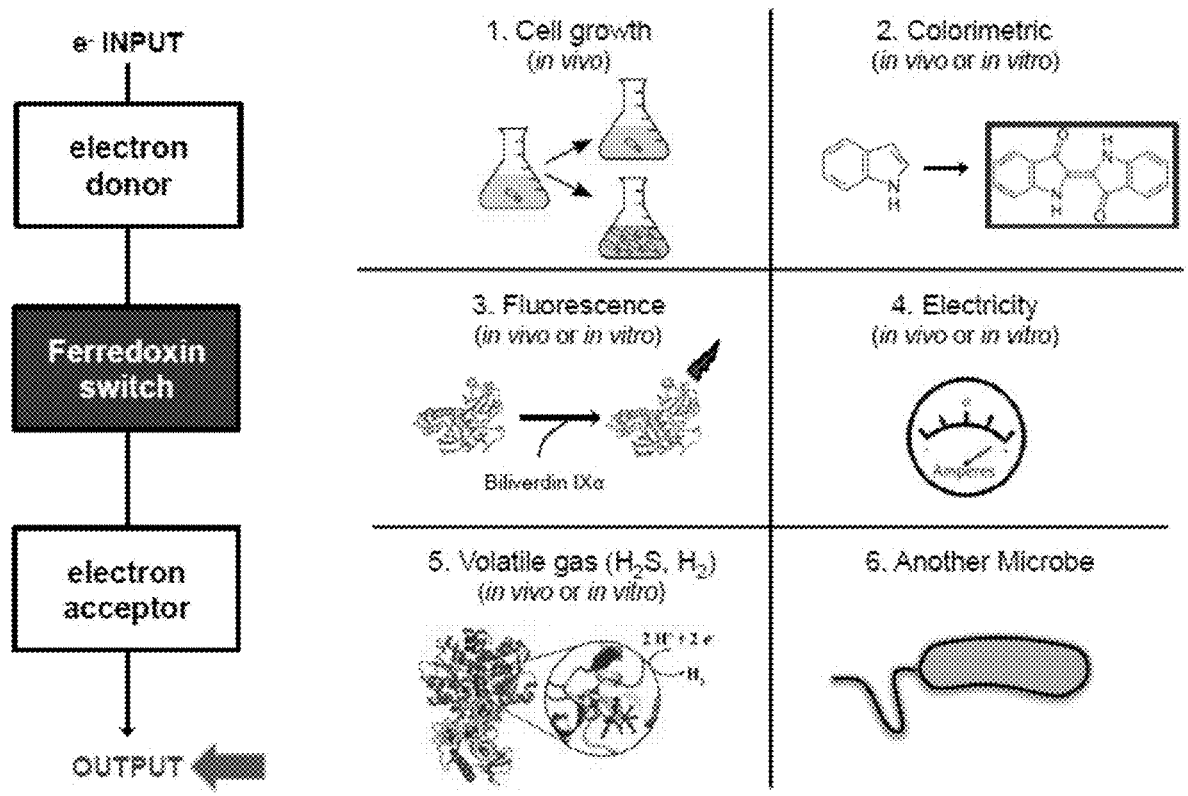
FIG. 24. Dynamic detection of pathway current.

For example, metabolite-responsive PECs would allow for control of electron flow by intermediate chemicals within pathways being used to synthesize high value chemicals (or controlled using the addition of exogenous chemicals). For example, if one were to design a system where electron flow was "off" until a particular metabolite accumulated, a fragmented PEC whose fragments required binding of that metabolite to associate and function as a redox protein could be employed. This would prevent unnecessary electron loss, such as losses to off-pathway reactions, until the desired chemical reaction for that electron flow is poised to accept those electrons. This conserves electrons within engineered microbes for the production of chemicals. And indeed, during late fermentation within a bioreactor, transcription is off as well, so classical methods cannot perform switching. Additionally, the inventors' approach is likely to work in a cell that is metabolically "off," provided that an electron source is added (see FIG. 23).

Alternatively, one may wish to delay electron flow to an inefficient enzyme/oxidoreductase until there is a sufficient amount of a desired substrate to outcompete other low level molecules that could bind and be utilized as non-specific substrates.

As described in greater detail below, the inventors have in one embodiment employed a two promoter system to drive expression of two distinct protein sub-fragments, where the fragments are brought together by a chemical that drives reconstitution of the an active PEC. In addition, a one promoter system that drives expression of a single protein that contains PEC domains separated spatially, where a conformational change drives reassembly of the split PEC domains has been generated. For example, the inventors have fused Fd split domains to estrogen receptor alone as well as Fd fused to estrogen receptor and red fluorescent protein (FIGS. 10A-12).

Figure 4:
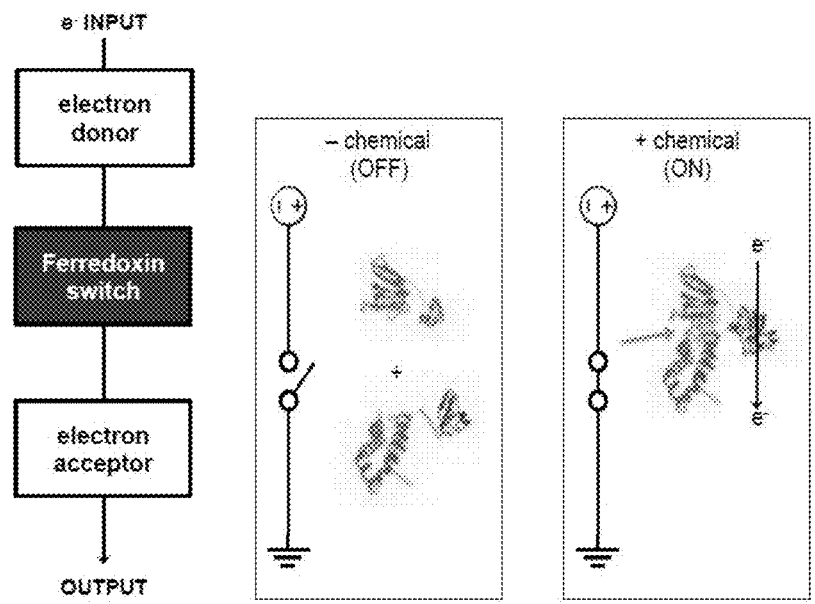
FIG. 4. Switch type #1. Fragments of PEC are fused to a pair of ligand-binding proteins, such as FKBP and FRB, using rapamycin as the chemical trigger for assembly.

Another approach is to create a two-fragment Fd, at least one of the fragments bind their complex cofactor after translation, but further requiring post-translational assistance to form the full polypeptide and reconstitute the functional electron redox hub. This approach allows a flexible platform to assess metabolites produced in engineered microbes (or added exogenously) using electron flow as a read-out (see FIG. 4). Feedback regulation involving these fragmented Fd could be generally useful for green chemical production. This is an example of what the inventors term "chemically-induced" complex formation.

Figure 7:
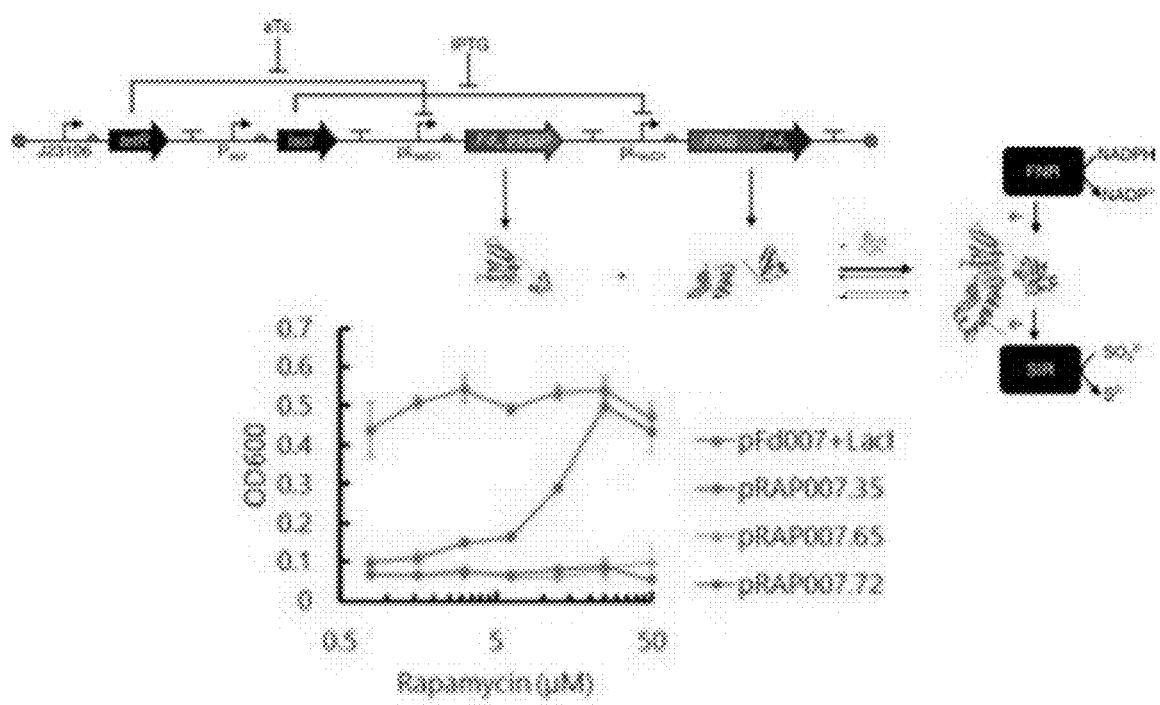
FIG. 7. Switch type #1. When fragments from PEC ferredoxin-35 are fused with FKBP and FRB, activity is only observed in the presence of rapamycin, which is read out as growth under aerobic conditions.
Figure 8:
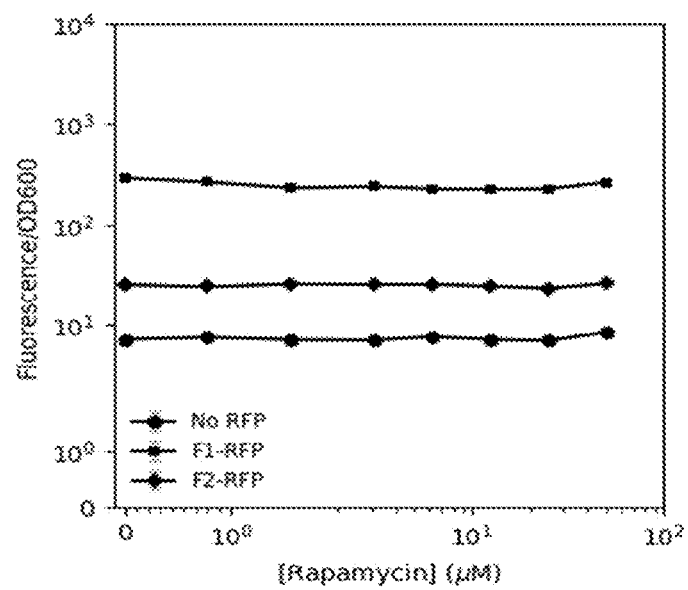
FIG. 8. Switch type #1. Addition of rapamycin does not change levels of fragments, indicating that switching is post-translational. Each fragment was fused to RFP, and the signal in the presence of rapamycin was fused to read out protein levels in cells, which did not change.
Figure 9:
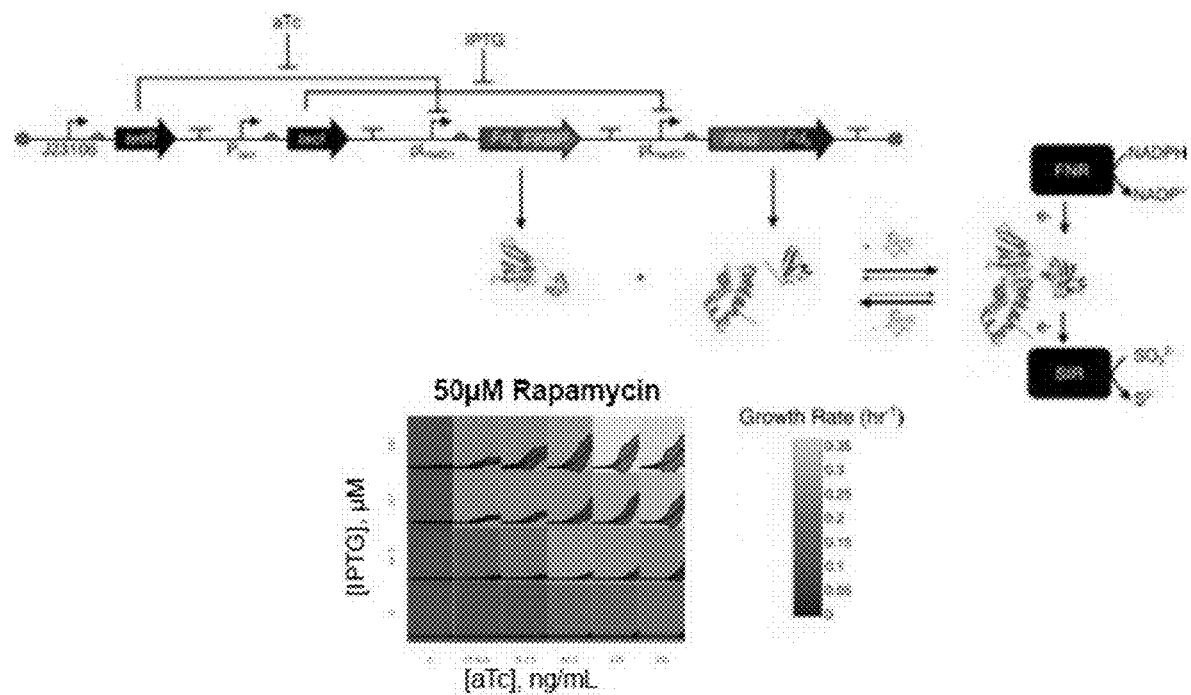
FIG. 9. Switch type #1. The circuit can be used as a three-input gate to control electron transfer, two slow transcription units and one fast input.
Figure 10A:
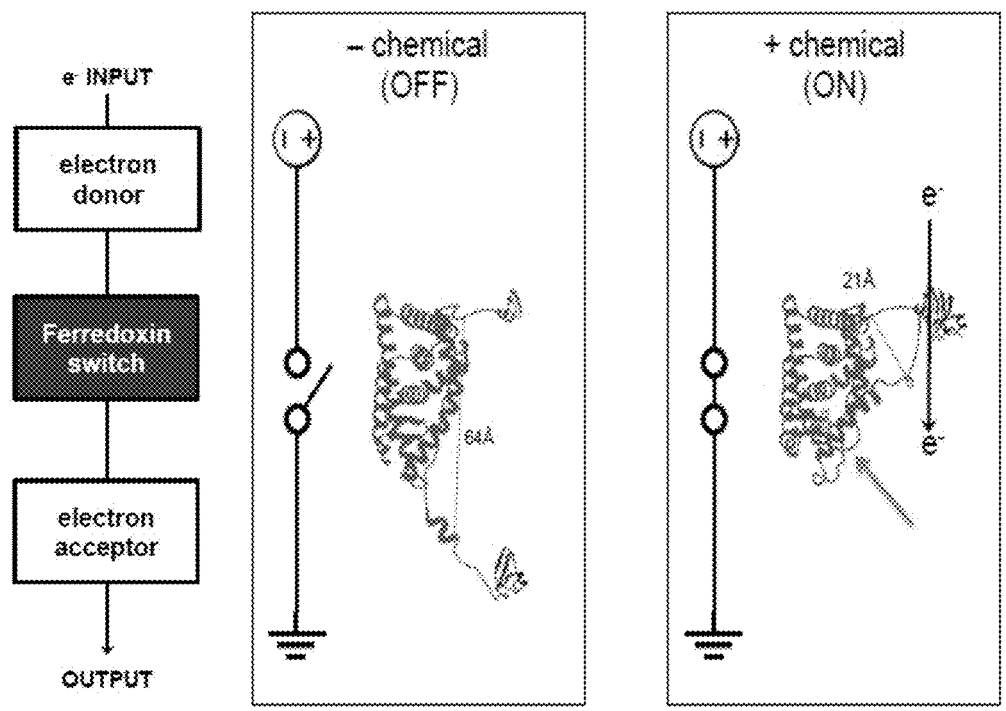
FIGS. 10A-B. Switch type #2. Fused fragments of PEC to a single ligand-binding protein, such as estrogen receptor, where the trigger is tamoxifen (FIG. 10A), optionally linked to RFP (as in FIG. 8). Data under aerobic conditions.
Figure 10B:
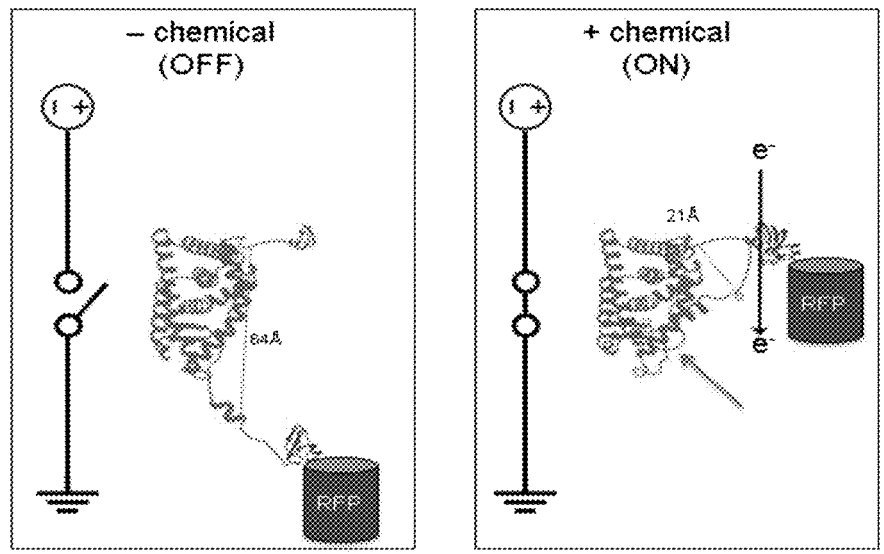
Figure 11:
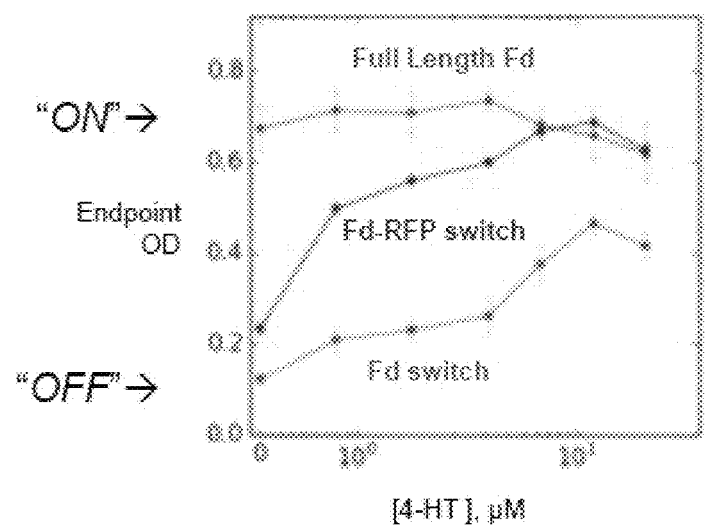
FIG. 11. Switch type #2. Addition of hydroxytamoxifen leads to switching, for which the read-out is growth. Data from system shown in FIG. 10A as well as a similar system created by fusing protein from to RFP (FIG. 10B).
Figure 12:
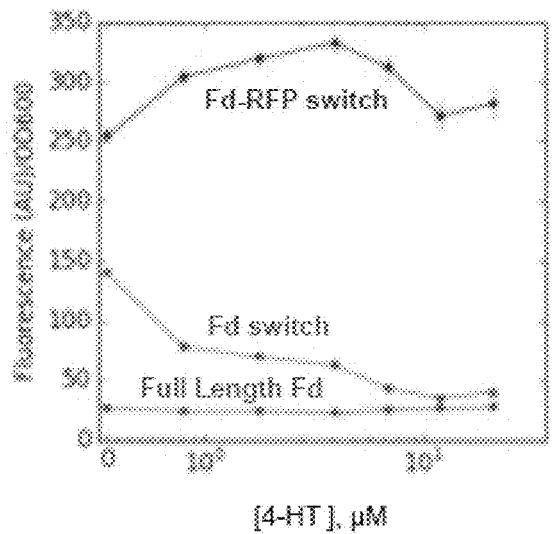
FIG. 12. Switch type #2. Monitoring the signal from the RFP binding shows that switch must be due to the protein altering electron transfer since total protein levels do not change in accordance with growth. Data from system shown in FIG. 10.
Figure 13:
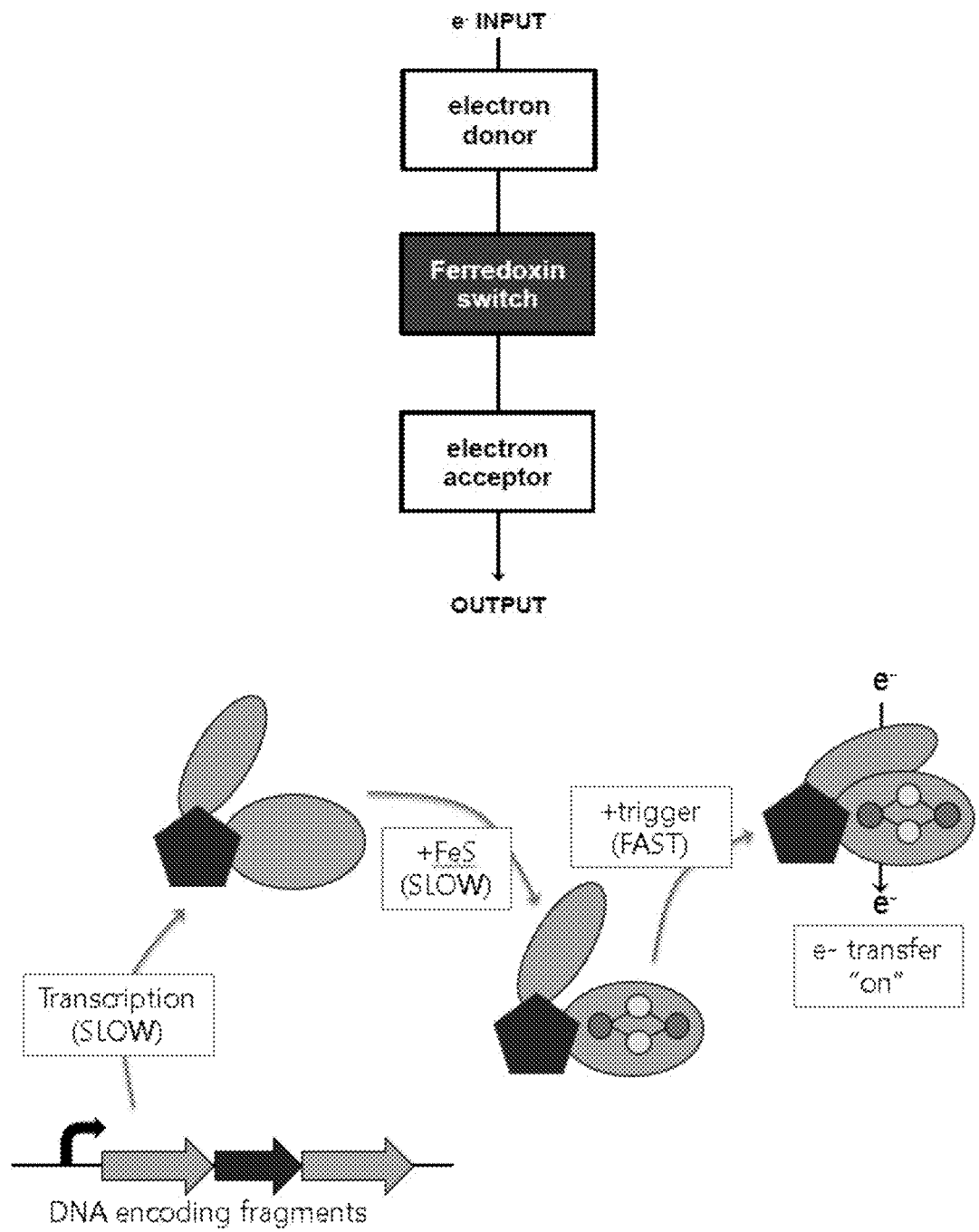
FIG. 13. Characteristics of a fast switch. Ferredoxin fragments must acquire a 2Fe2S cluster in the "off" state so that they are poised to switch to the "on" state quickly through a process that is limited by (i) the input signal and (ii) the conformational change induced by that signal.
Figure 14:
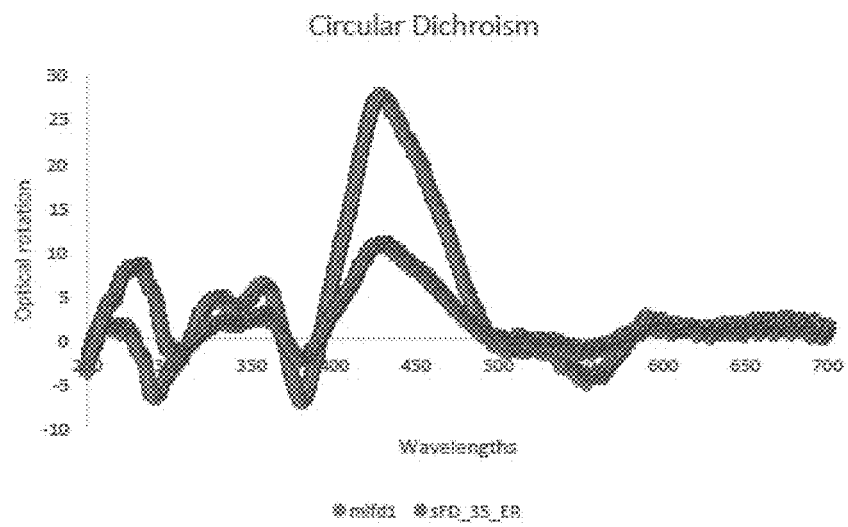
FIG. 14. Characteristics of a fast switch. When the ferredoxin is purified in the absence of chemical, there is evidence for a bound 2Fe2S cluster under aerobic conditions. The protein displays a visible circular dichroism spectrum having the same minima and maxima that are characteristic of bound 2Fe2S cluster, such as in native ferredoxin.
Figure 15:
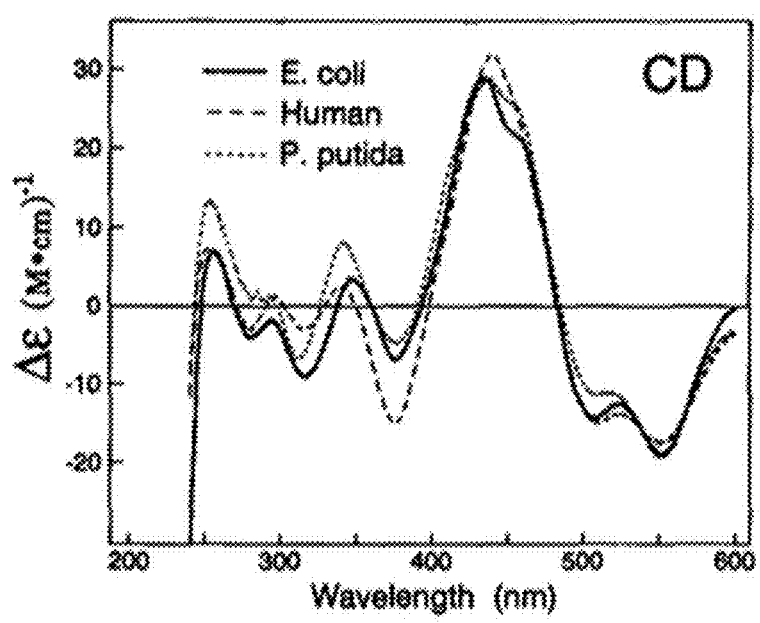
FIG. 15. Characteristics of a fast switch. Published spectra on multiple ferredoxins are similar to the split Fd fused to estrogen receptor.
Figure 16A:
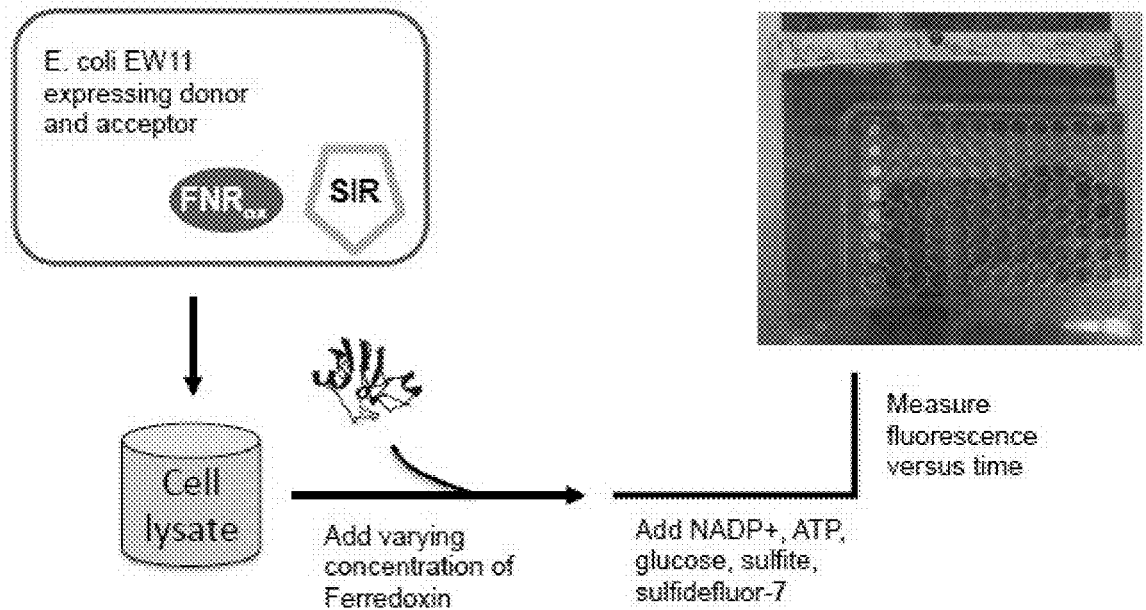
FIGS. 16A-B. Characteristics of a fast switch.
Figure 16B:
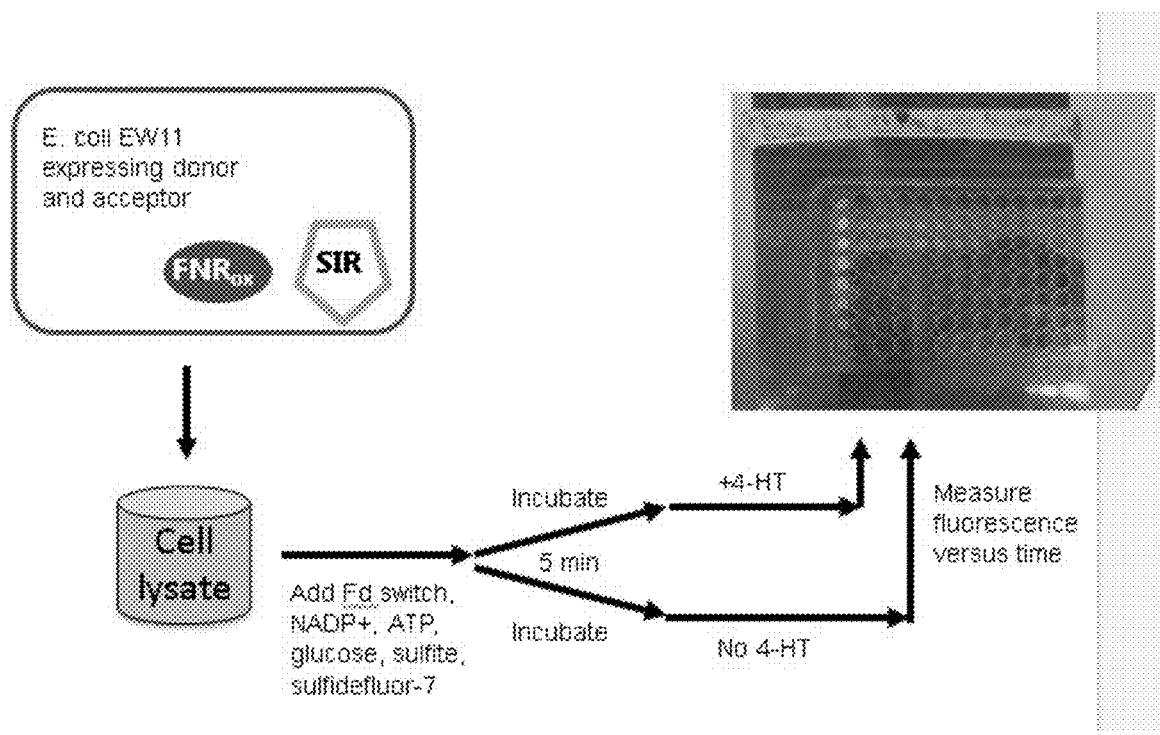
Figure 17:
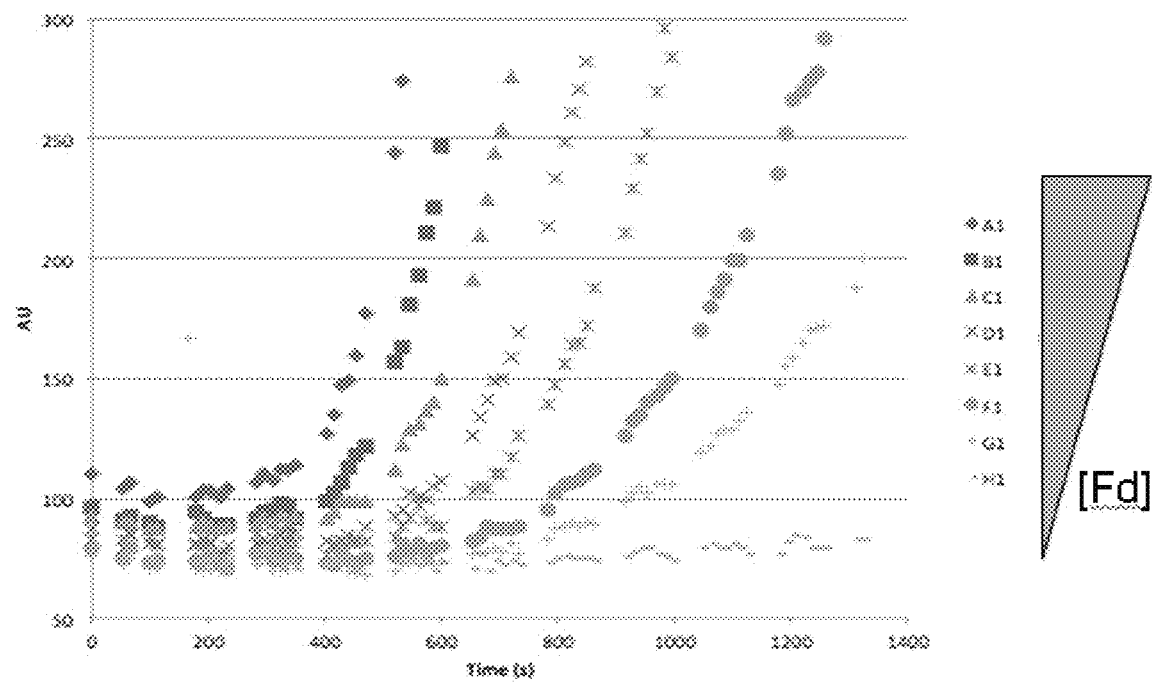
FIG. 17. Characteristics of a fast switch. Fluorescence of sulfidefluor-7 as a function of purified ferredoxin added to a cell lysate containing a donor and acceptor protein.
Figure 18:
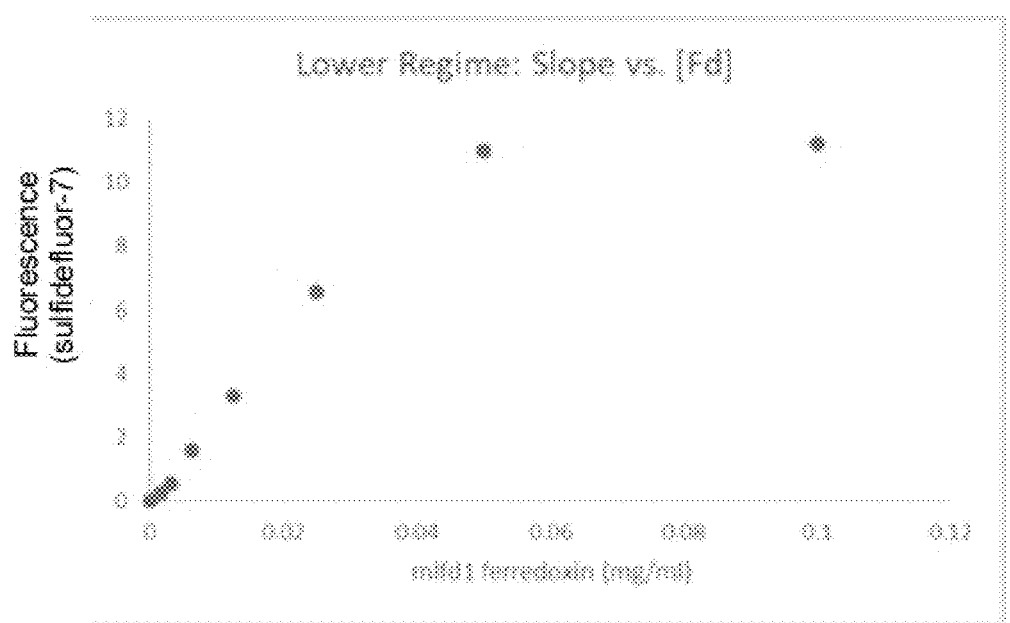
FIG. 18. Characteristics of a fast switch. Evidence that the signal from cell lysate is ferredoxin-dependent.
Figure 19:
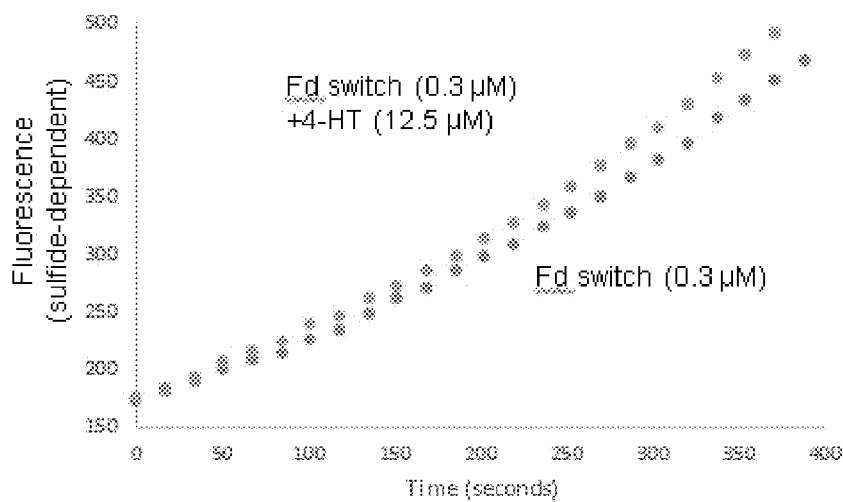
FIG. 19. Characteristics of a fast switch. A cellular assay has been developed for monitoring the timescale of switching (4-HT added at t=0). Under initial conditions, the sample containing 4-HT yields a higher rate of sulfide production, which is detectable within 1.5 minutes of chemical addition. (4-HT addition alone has does not affect rate).

In a particular example, the inventors have used a rapamycin stabilized protein-protein interaction to demonstrate post-translational control over PEC activity. Here, the two domains of the PEC are located in separate fusion constructs (fused to FKBP and FRB), and the interaction of the fusion partners is driven by binding of rapamycin Banaszynski (2005), which further drives reconstitution of the PEC complex and electron flow (FIGS. 7-9).

Other potential examples of chemical-binding protein pairs that could be employed are:

| Target proteins | | Dimerizing agent |
|---|---|---|
| FKBP | FKBP | FK1012 |
| FKBP | CalcineurinA (CNA) | FK506 |
| FKBP | CyP-Fas | FKCsA |
| FKBP | FRB domain of mTOR | Rapamycin |
| GyrB | GyrB | Coumermycin |
| GAT | GID1 | Gibberellin |
| Snap-tag | HaloTag | HaXS |

Figure 20:
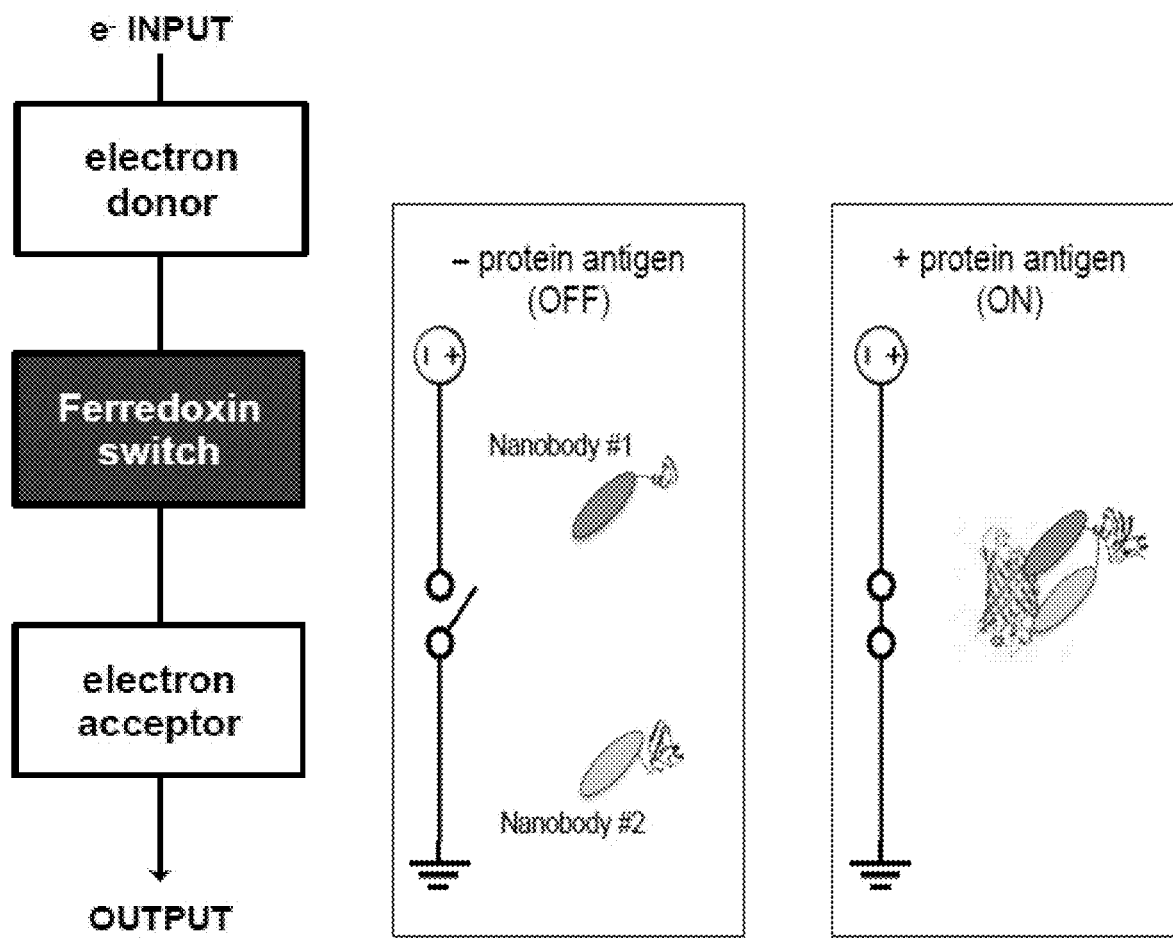
FIG. 20. Alternative switch triggers (protein input). Fuse fragments to nanobodies that bind the same antigen.
Figure 21:
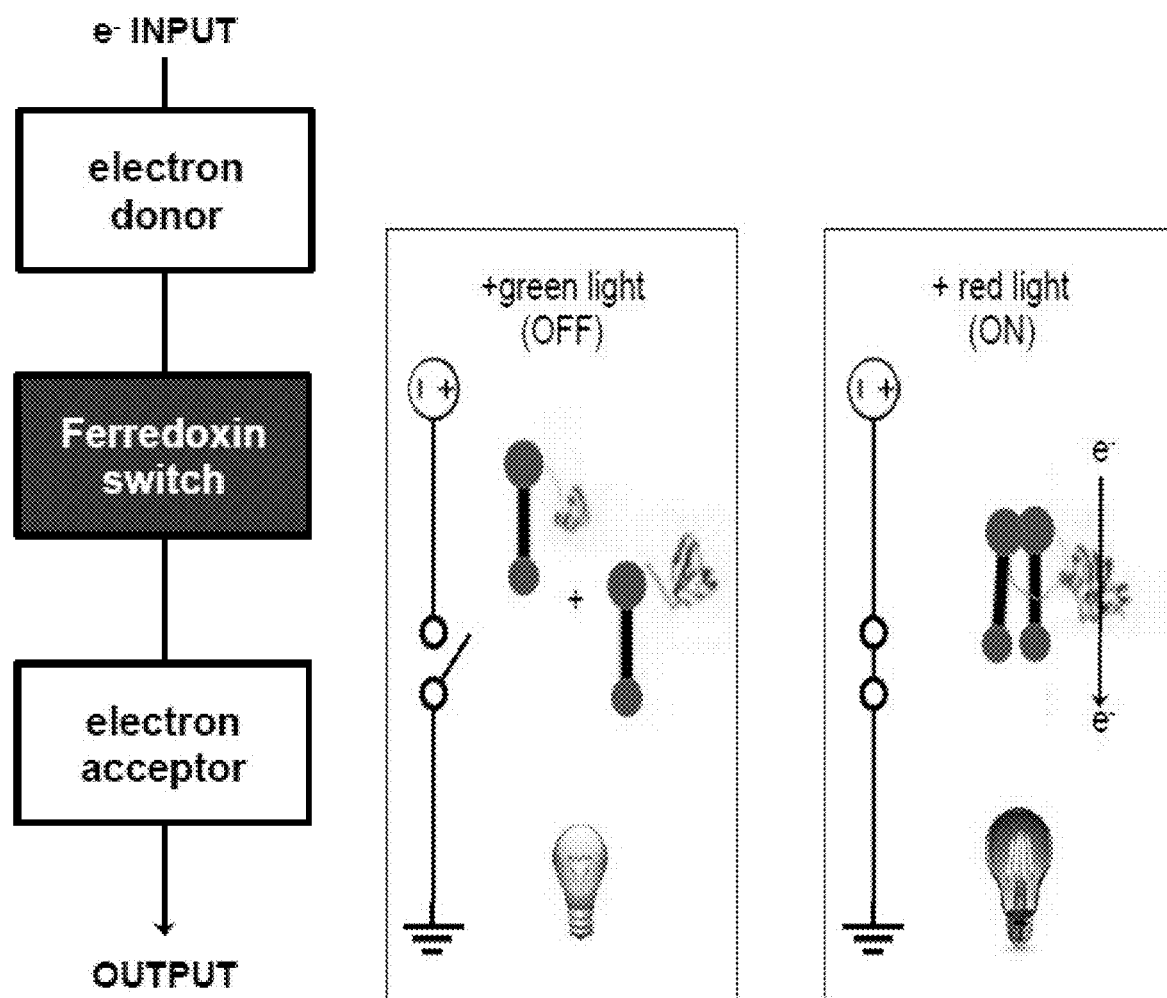
FIG. 21. Alternative switch triggers (light input). Fuse fragments to 2-component signaling systems.
Figure 22:
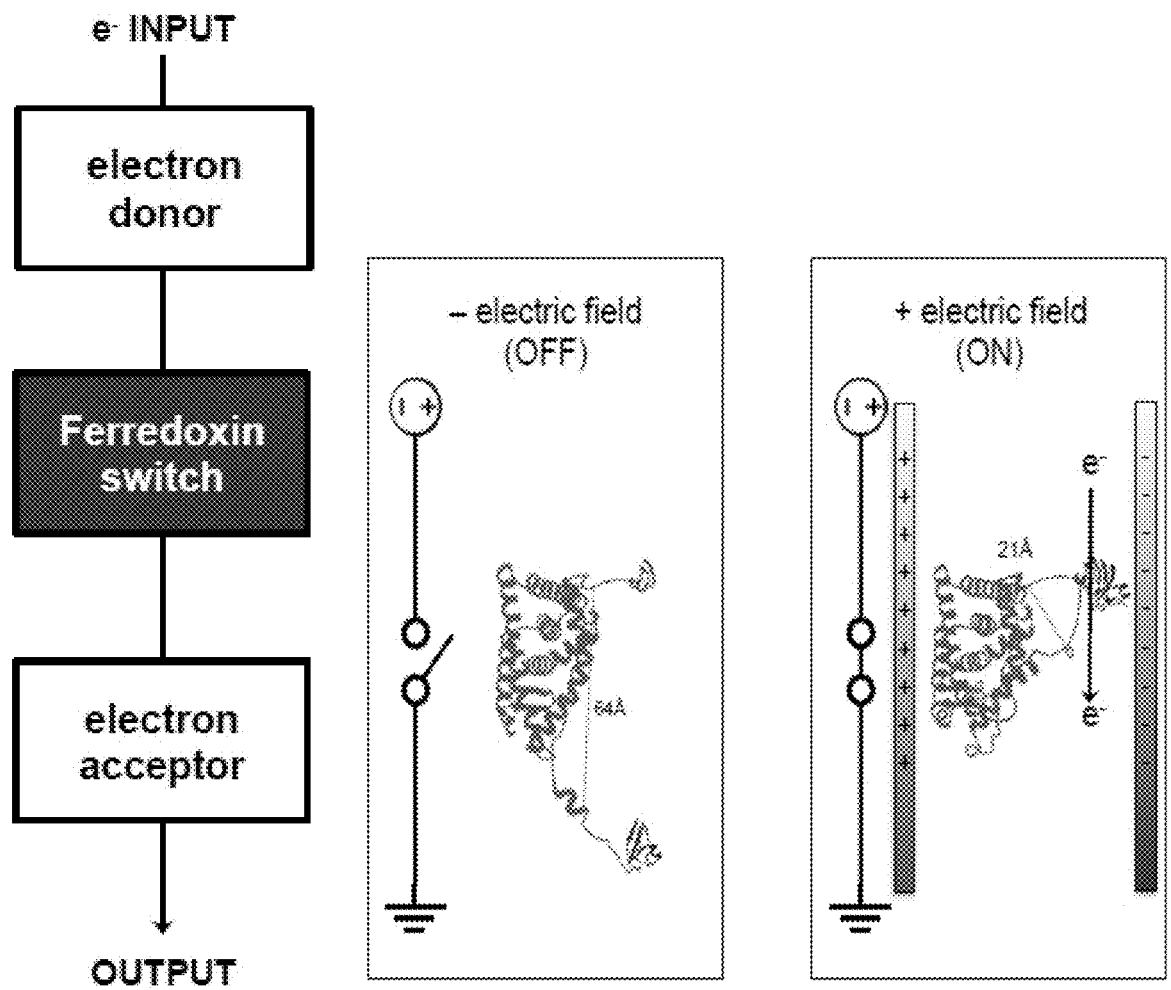
FIG. 22. Alternative switch triggers (electrical field). Fuse fragments to proteins influenced by electric fields.

As discussed above, the inventors' efforts have focused on Fe—S cluster containing protein electron carriers, specifically a 2Fe2S ferredoxin. Initially, the inventors used IPTG and aTc regulated promoters to control fragmented PEC expression and activity. Other examples use one or two promoter systems, and can employ a variety of environmental factors to drive split PEC complementation, such as light, electricity, photosynthesis and fluorescence (see FIGS. 20-22).

IV. CELL EXPRESSION

Initial experiments proceeded in *E. coli* for convenience, but the addition of genes to bacteria is of nearly universal applicability, so it will be possible to use a wide variety of organisms with the selection of suitable vectors for same. A number of databases include vector information and/or a repository of vectors. See, e.g., Addgene.org, which provides both a repository and a searchable database allowing vectors to be easily located and obtained from colleagues. See also Plasmid Information Database (PlasmID) and DNASU having over 191,000 plasmids. A collection of cloning vectors of *E. coli* is also kept at the National Institute of Genetics as a resource for the biological research community. Furthermore, vectors (including particular ORFS therein) are usually available from colleagues.

Once an exemplary sequence (PEC or fusion partner) is obtained, many additional example proteins of similar activity can be identified by BLAST search or database search. The OMNI database is also a good resource for searching human proteins and has links to the sequences. Further, every protein record is linked to a gene record, making it easy to design genome insertion vectors. Many of the needed sequences are already available in vectors, and can often be obtained from cell depositories or from the researchers who cloned them. But, if necessary, new clones can be prepared based on available sequence information using gene synthesis or PCR techniques. Thus, it should be easily possible to obtain all of the needed sequences.

Understanding the inherent degeneracy of the genetic code allows one of ordinary skill in the art to design multiple sequences that encode the same amino acid sequence. NCBI® provides codon usage databases for optimizing DNA sequences for protein expression in various species. Using such databases, a gene or cDNA may be "optimized" for expression in probiotic strains, mice, humans, or other species using the codon bias for the species in which the gene will be expressed.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence).

Alignments may be performed using BLAST homology alignment as described by Tatusova T A & Madden T L (1999) *FEMS Microbiol. Lett.* 174:247-250. Default parameters were used, except the filters were turned OFF. As of Jan. 1, 2001 the default parameters were as follows: BLASTN or BLASTP as appropriate; Matrix=none for BLASTN, BLOSUM62 for BLASTP; G Cost to open gap default=5 for nucleotides, 11 for proteins; E Cost to extend gap [Integer] default=2 for nucleotides, 1 for proteins; q Penalty for nucleotide mismatch [Integer] default=-3; r reward for nucleotide match [Integer] default=1; e expect value [Real] default=10; W word size [Integer] default=11 for nucleotides, 3 for proteins; y Dropoff (X) for blast extensions in bits (default if zero) default=20 for blastn, 7 for other programs; X dropoff value for gapped alignment (in bits) 30 for blastn, 15 for other programs; Z final X dropoff value for gapped alignment (in bits) 50 for blastn, 25 for other programs. This program is available online at NCBI™ (ncbi.nlm.nih.gov/BLAST/). "Positives" includes conservative amino acid changes in addition to identities.

V. DEFINITIONS

The following are general definitions that may be used to better understand the disclosure as presented herein.

A "reporter gene" is an easily monitored gene that is heterologous to said output promoter (thus the normal downstream target is by definition excluded), and preferably is not present in the host species. Fluorescent proteins make excellent reporters. For example, a gene that is normally turned on (or off) by an active PEC would provide a suitable promoter that could be operatively coupled to a green fluorescent protein (GFP) gene, thus making a reporter gene construct with which to assay fragment complementation of PEC fragments. Other fluorescent proteins include, but are not limited to red fluorescent protein, far red fluorescent protein, blue fluorescent protein, orange fluorescent protein, yellow fluorescent protein, mCHERRY, tdTOMATO, mORANGE, mCITRINE, VENUS, YPET, EMERALD, mNEONGREEN and CERULEAN. A great many others are available, see e.g., nic.ucsf.edu/dokuwiki/doku.php?id=fluorescent_proteins, incorporated by reference herein in its entirety for all purposes.

The amount or activity of the reporter protein produced is taken as a proxy for the cellular response to the target. Ideal reporter proteins are easy to detect and quantify (preferably noninvasively), highly sensitive and, ideally, not present in the native organism. They can be set up to detect either gene activated or deactivation. Several currently popular reporter proteins and their characteristics are listed in Table 1.

TABLE 1

Common spectroscopically active reporter proteins and their detection

| Reporter protein | Reporter genes | Origin | Substrate | Detection method | Comments | Refs |
|---|---|---|---|---|---|---|
| Bacterial luciferase | luxAB* or luxCDABE | Bioluminescent bacteria* | $O_2$, $FMNH_2$ and long-chain aldehydes | Bioluminescence | Requires $O_2$; aldehyde addition is required if only luxAB is used | 94, 95 |
| Firefly luciferase | lucFF | Firefly (*Photinus pyralis*) | $O_2$, ATP and luciferin | Bioluminescence | Requires $O_2$ | 96 |
| Click beetle luciferase | lucGR | Click beetle (*Pyrophorus plagiophthalamus*) | $O_2$, ATP and pholasin | Bioluminescence | Requires $O_2$ | 97 |
| *Renilla* luciferase | Rluc | *Renilla reniformis* | Coelenterazine and $Ca^{2+}$ | Bioluminescence | Requires $O_2$ | 98 |
| β-Galactosidase | lacZ | *Escherichia coli* | Galactopyranosides‡ | Chemiluminescence, colorimetry, electrochemistry and fluorescence | External substrate addition (may require cell permeabilization) | 1 |
| Fluorescent proteins | gfp, etc. | *Aequorea victoria* and additional marine invertebrates | N/A | Fluorescence | $O_2$ is required for maturation; different colour varieties exist | 99-101 |
| Spheroidene monooxygenase | crtA | *Rhodovulum sulfidophilum* | Spheroidene | Colorimetry | None | 102 |
| Infrared fluorescent proteins | Various | Bacteriophytochrome Family | N/A | Fluorescence | None | 103 |
| FMN-based fluorescent proteins | Various | Engineered from *Bacillus subtilis* and *Pseudomonas putida* | None | Fluorescence | Functional in both oxic and anoxic conditions; requires endogenous FMN | 104 |

N/A, not applicable.
*Most commonly used species include *Aliivibrio fischeri* (also known as *Vibrio fischeri*), *Vibrio harveyi* and *Photorhabdus luminescens*.
‡For example, O-nitrophenyl-β-D-galactoside (ONPG), 5-bromo-4-chloro-3-indolyl-β-D-galactopyranoside (X-gal), 4-methylumbelliferyl-β-D-galactopyranoside, 4-aminophenyl-β-D-galactopyranoside and D-luciferin-O-β-galactopyranoside.

For in vivo use, a longer lasting reporter signal (8-12 hrs) may be preferred, such that signal can still be detected in stool samples. Using the amount of reporter gene as a readout, and using standard high throughput screening methods, such as fluorimetry or flow-cytometry, PEC fragment pairs can be screened using standard, high throughput laboratory assays. This method can thus be used to identify other suitable fragment pairs for use herein.

A "promoter" is a gene sequence that controls expression of the gene that it is in. An inducible promoter is induced or turned on by the addition, e.g., of an activator, but can also be turned off in response to a ligand. Some amount of constitutive expression may still be present even in a strongly inducible promoter.

"Cognate" refers to two component system that functions together, such as, e.g., a ligand binding domain that will bind to ligand. The ligand binding domain and ligand are thus cognate, meaning they bind each other.

"Expression vectors" are used in accordance with the art-accepted definition of a plasmid, virus or other propagatable sequence designed for protein expression in cells. There are thousands of such vectors commercially available, and typically each has an origin of replication (ori); a multiple cloning site; a selectable marker; ribosome binding sites; a promoter and often enhancers; and the needed termination sequences. Most expression vectors are inducible, although constitutive expressions vectors also exist and either can be used.

As used herein, "inducible" means that gene expression can be controlled by the hand-of-man, by adding e.g., a ligand to induce expression from an inducible promoter. Exemplary inducible promoters include the lac operon, inducible by IPTG, the yeast AOX1 promoter inducible with methanol, the strong LAC4 promoter inducible with lactate, and the like. Low level of constitutive protein synthesis may occur even in expression vectors with tightly controlled promoters.

As used herein, an "integrated sequence" means the sequence has been integrated into the host genome, as opposed to being maintained on an expression vector. It will still be expressible, and preferably is inducible as well, although in other cases a strong constitutive promoter may be preferred.

As used herein, reference to cells, bacteria, microbes, microorganisms and like is understood to include progeny thereof having the same genetic modifications. It is also understood that all progeny may not be precisely identical in DNA content, due to deliberate or inadvertent mutations that have been added to the parent. Mutant progeny that have the same function or biological activity as screened for in the originally transformed cell are included. Where distinct designations are intended, it will be clear from the context.

The terms "operably associated" or "operably linked," as used herein, refer to functionally coupled nucleic acid sequences.

As used herein "recombinant" or "engineered" is relating to, derived from, or containing genetically engineered material. In other words, the genome was intentionally manipulated in some way by the hand-of-man.

"Reduced activity" or "inactivation" is defined herein to be at least a 75% reduction in protein activity, as compared with an appropriate control species. Preferably, at least 80, 85, 90, 95% reduction in activity is attained, and in the most preferred embodiment, the activity is eliminated (100%, aka a "knock-out" or "null" mutants which produce undetectable levels of activity). Proteins can be inactivated with inhibitors, by mutation, or by suppression of expression or translation, and the like. Use of a frame shift mutation, early stop codon, point mutations of critical residues, or deletions or insertions, and the like, can completely inactivate (100%) gene product by completely preventing transcription and/or translation of active protein.

"Overexpression" or "overexpressed" is defined herein to be at least 150% of protein activity as compared with an appropriate control species, and preferably 200, 500, 1000%) or more, or any expression is a species that otherwise lacks the activity. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or up-regulating the endogenous gene, and the like.

The term "endogenous" or "native" means that a gene originated from the species in question, without regard to subspecies or strain, although that gene may be naturally or intentionally mutated, or placed under the control of a promoter that results in overexpression or controlled expression of said gene. Thus, genes from *Clostridia* would not be endogenous to *Escherichia*, but a plasmid expressing a gene from *E. coli* would be considered to be endogenous to any genus of *Escherichia*, even though it may now be overexpressed. By contrast, "wild-type" means the natural functional gene/protein as it exists in nature.

The following abbreviations are used herein:

| ABBREVIATION | TERM |
| --- | --- |
| 4-HT | 4-hydroxytamoxifen |
| aTc | Anhydrotetracycline |
| CID | Chemically-inducible dimerization |
| Cys | Cysteine |
| DBD | DND binding domain |
| e- | Electron |
| F1 | N-terminal fragment |
| F2 | C-terminal fragment |
| Fd | Ferredoxin |
| FNR | Ferredoxin:NADP reductase |
| GFP | Green fluorescent Protein |
| HiPIP | High potential iron-sulfur proteins |
| IPTG | Isopropyl β-D-1-thiogalactopyranoside |
| IPR | InterPro |
| k* | Number of unique amino acids in multiple sequence alignment |
| LBD | Ligand Binding Domain |
| NADH | Nicotinamide adenine dinucleotide |
| NADPH | Isopropyl β-D-1-thiogalactopyranoside |
| PEC | Protein electron carrier |
| PlasmID | Plasmid Information Database |
| sFd | Split ferredoxin |
| SIR | Sulfite reductase |
| TetR | tetracycline repressor |

VI. EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Materials and Methods

Materials. Rapamycin was from TCI America, isopropyl β-D-1-thiogalactopyranoside (IPTG) was from RPI, and all other chemicals were purchased from Sigma-Aldrich.

Vector design. Table 2 lists all of the plasmids. These were constructed using Golden Gate DNA assembly (Engler et al., 2008) of PCR products amplified using Phusion DNAP (Thermo-Fisher). The genes encoding *Zea mays* FNR, *Zea mays* SIR, and *Spinacia oleracea* Fd were a gift from P. Silver (Harvard University). The genes encoding *Mastigocladus laminosus*, *Zea mays*, *Chlamydomonas reinhardtii*, and cyanomyophage PSSM-2 Fd were synthesized as G-blocks by Integrated DNA Technologies. The genes for Ml-Fd and sFd-35-ER were cloned into pET-28b to create expression vectors for protein purification. All vectors were sequence verified.

Calculations. A multiple sequence alignment (MSA) of 60 plant-type Fd sequences was generated using MUSCLE (Edgar, 2004). Positional amino acid sequence divergence was calculated as the number of unique amino acids observed at each Ml-Fd native site. Any sites containing a gap in one or more Fd sequences was given a sequence divergence value of 20. The sequence divergence value for each Fd native site was calculated as the average for a sliding window of three sites. The UniProt numbers for each Fd are provided in Table 3.

Growth assay. For all growth experiments, *E. coli* EW11 were freshly transformed with two plasmids, one encoding the e-donor and acceptor pair (FNR and SIR) and the other encoding either a native Fd, a C42A mutant of Ml Fd that is unable to coordinate a 2Fe-2S cluster, or an engineered Fd. Starter cultures were inoculated using single colonies obtained by selecting for colonies containing both plasmids on LB-agar plates. These starter cultures were grown in deep-well 96-well plates for 18 hours at 37° C. in 1 mL of a non-selective modified M9 medium (M9c), which contained sodium phosphate, dibasic (6.8 g/L), sodium phosphate, monobasic (3 g/L), sodium chloride (0.5 g/L), ammonium chloride (1 g/L), calcium chloride (0.1 mM), magnesium sulfate (10 mM), ferric citrate (24 mg/L), p-aminobenzoic acid (2 mg/L), inositol (20 mg/L), adenine (5 mg/L), uracil (20 mg/L), tryptophan (40 mg/L), tyrosine (1.2 mg/L), and the remaining 18 amino acids (80 mg/L each). For auxotroph complementation analysis, starter cultures that had been grown to stationary phase in M9c were diluted ~1:100 using a 96-well replicator pin into 100 µL of a selective modified M9 medium (M9sa), which is identical to M9c but lacks cysteine and methionine. Cells were grown in the presence of the indicated amount of inducers (aTc, IPTG, rapamycin, or 4-HT) in an Infinite m1000 Pro plate reader (Tecan) at 37° C. with shaking at 250 rpm at an amplitude of 1.5 mm in double-orbital mode. Optical density (OD) measurements were taken every 10 minutes. To select for the Fd and e-donor/acceptor plasmids, all growth steps included chloramphenicol and streptomycin at 34 µg/mL and 100 µg/mL, respectively.

Fluorescence spectroscopy. Whole cell RFP measurements were done as with the growth assay except starter cultures were diluted ~1:100 using a 96-well replicator pin into M9c medium (100 µL) and grown in an incubator at 37° C. with shaking at 250 rpm. After 24 hours of growth, OD and fluorescence (λex=560 nm, λem=650 nm) were measured using an Infinite m1000 Pro plate reader (Tecan). Fluorescence was normalized to OD and scaled relative to the condition without chemical inducer.

Protein purification. *E. coli* Rosetta transformed with pET28b containing the Ml-Fd or sFd-35-ER genes were grown at 37° C. in LB medium containing 50 µg/mL kanamycin to mid-log phase, induced using 50 µM IPTG, and grown overnight at 30° C. while shaking at 250 rpm. Cells harvested by centrifugation (4000 g) were resuspended in 20 mL of lysis buffer (per L of culture), which contained 10 mM Tris pH 8, 5 mM dithiothreitol (DTT), 10 mg/L DNase I, and 0.5 mg/mL lysozyme. After freezing overnight at −80° C., cells were thawed and mixed with a cOmplete™ Mini, EDTA-Free protease inhibitor tablet (Sigma-Aldrich) at a ratio of one tablet per 400 mL of total cell lysate. Cell lysates were loaded onto a DE52 anion exchange column (Whatman) that had been equilibrated with TED buffer (25 mM Tris pH 8, 1 mM EDTA, and 1 mM DTT), the column was washed with TED containing 200 mM NaCl, and Fe—S proteins were eluted using TED containing 300 mM NaCl. The brown eluent was diluted with TED to bring NaCl below 100 mM and loaded onto HiTrap Q XL column (GE Healthcare) that had been equilibrated with TED using an AKTA Start FPLC system (GE Healthcare). This column was washed using TED buffer, a linear gradient was run from 0 to 375 mM NaCl TED, and an isocratic 500 mM NaCl TED solution was used to elute the Fe—S proteins. SDS-page was performed using NuPage 12% Bis-Tris Gels (Invitrogen) and the PageRuler Unstained Broad Range Protein Ladder (Thermo Scientific). Samples were concentrated 20-fold using an Amicon Ultra 10K MWCO spin column. Concentrated samples were flash frozen with liquid nitrogen.

Spectroscopy. Purified Ml-Fd and sFd-35-ER were dialyzed into TED buffer (25 mM Tris pH 8, 1 mM EDTA, 1 mM DTT). Each protein was incubated with 4-HT (100 µM) or the carrier DMSO used to dissolve 4-HT (1% of final volume) for 30 min. A J-815 spectropolarimeter (Jasco) was used to measure the ellipticity of samples from 700 nm to 300 nm. UV/Vis absorbance of samples was read using a Cary 50 UV/Vis Spectrophotometer (Varian) from 600 nm to 250 nm. Measurements used quartz cuvettes with a 1 cm path length.

Cell lysates. Electrocompetent $E.\ coli$ EW11 were transformed with the plasmid (pSAC01) that constitutively expresses $Zea\ mays$ FNR and SIR. Cells were grown to stationary phase at 37° C. and 250 rpm in 2×YTPG medium (16 g/L tryptone, 10 g/L yeast extract, 5 g/L NaCl, 3 g/L KH2PO4, 7 g/L K2HPO4, and 18 g/L glucose) containing 100 µg/mL streptomycin. Cells from overnight cultures were diluted 1:100 in fresh 2×YTPG medium containing streptomycin, grown for 2 hours at 37° C. while shaking at 250 rpm until mid-log phase, and then shifted to 30° C. and grown for an additional 4 hours. Cell cultures were harvested by centrifugation (4000 g), cells were resuspended in equal volume of S30 buffer (10 mM Tris-acetate, 14 mM magnesium acetate, 60 mM potassium acetate pH 8.2), cells were washed twice with S30 buffer, and the pellets were weighed and flash frozen with liquid nitrogen. Pellets were thawed, and resuspended in 2 mL of S30 buffer per gram of cell pellet, and sonicated using a Q500 Sonicator (Qsonica) with the probe at 20 kHz and 40% maximal amplitude until samples had been exposed to ~0.5 Joules of sonication energy per µL of cell slurry (Kwon & Jewett, 2015). To minimize sample overheating, sonication proceeded for 25 seconds followed by a 15 second rest period between sonication pulses. To remove native reduced cofactors like NADH and NADPH, lysates were applied to a Zeba Spin Desalting Column 7K MWCO (Thermo Scientific) that had been equilibrated with S30 buffer. Protein content in lysates was quantified using Bio-Rad Protein Assay Dye Reagent Concentrate (Bio-Rad), using bovine serum albumin (NEB) as a standard.

Sulfide production assay. To visualize sulfide production, cells lysates were diluted 2-fold into S30 buffer to 4.8 mg/mL of total protein. Desalted lysates were diluted 1.25-fold with 5×LSR buffer, which contained 50 mM sodium sulfite, 200 µM β-Nicotinamide adenine dinucleotide 2'-phosphate reduced tetrasodium salt (NADPH), 10 µM Sulfidefluor 7 AM (Tocris) (Aliverti et al., 2001), 670 mM potassium acetate, 50 mM ammonium acetate, 40 mM magnesium acetate, and 50 mM potassium phosphate, dibasic pH 7.2. To analyze background sulfide production from lysates alone, additional NADPH was added to the lysate/LSR mixture to achieve higher concentrations. To analyze Fd-dependent sulfide production, purified Ml-Fd or sFd-35-ER was added at the indicated concentrations to the lysate diluent S30 buffer. To limit disulfide bond formation in the ER-LBD sFd-35-ER, which has been observed in past studies (Tanenbaum et al., 1998), this protein was first reduced with freshly made 1 mM DTT in S30 buffer for 20 minutes on ice and then desalted immediately before addition to the assay using a Zeba Spin Desalting Column 7K MWCO. Following NADPH or protein addition, reactions were arrayed in a Corning 96 well plate at room temperature (Cost ar #3603), transferred to an Infinite m1000 Pro plate reader (Tecan), and heated to 37° C. and shaken at 250 rpm with fluorescence readings ($\lambda$ex=495 nm, $\lambda$em=520 nm) every 15 seconds. When analyzing chemical-dependent sulfide production, 12.5 µM 4-hdyroxytamoxifen (4HT) or blank ethanol was injected into the plate following two minutes of incubation and the lysate diluent S30 buffer volume was reduced accordingly.

Midpoint potentials. Electrochemical experiments were carried out anaerobically in a MBraun Labmaster glovebox using a PGSTAT12 potentiostat. A three-electrode configuration was used in a water-jacketed glass cell. A platinum wire was used as the counter electrode and a standard calomel electrode was used as the reference electrode. Reported potentials are relative to the standard hydrogen electrode. Baseline measurements were collected using an edge-plane graphite (EPG) electrode that was modified with a 100 mM neomycin trisulfate solution, rinsed, and placed into a glass cell containing a 23.5° C. mixed buffer solution (5 mM acetate/MES/MOPS/TAPS/CHES/CAPS) pH 7.0, with 100 mM NaCl. A 5 µL aliquot of 720 µM Ml-Fd or 5 mM sFd-35-ER was applied directly to the electrode surface with or without 1 µL of 50 mM 4-HT, the protein was allowed to reduce in size for approximately one minute at room temperature before being placed into the buffer cell solution. Square wave voltammograms were collected at 23.5° C. with a frequency of 10 Hz and electrochemical signals were analyzed using QSoas.

Statistical analysis. Growth assays and whole cell fluorescence data are reported as the mean and standard deviation of biological replicates (n=3). The sulfide production data are reported as the mean and standard deviation of technical replicates (n=3). All reported p-values were obtained using two-tailed, independent t-tests.

TABLE 2

Vectors constructed

| Plasmid Name | Description |
| --- | --- |
| pSAC01 | $Spec^R$, p15a vector constitutively expressing $Zea\ mays$ FNR and $Z.\ mays$ SIR |
| pFd003 | $Cam^R$, ColE1 vector with aTc inducible $Spinacia\ oleracea$ Fd1 |
| pFd004 | $Cam^R$, ColE1 vector with aTc inducible $Chlamydomonas\ reinhardtii$ Fd1 |

TABLE 2-continued

Vectors constructed

| Plasmid Name | Description |
| --- | --- |
| pFd007 | Cam$^R$, ColE1 vector with aTc inducible *Mastigocladus laminosus* Fd1 |
| pFd022 | Cam$^R$, ColE1 vector with aTc inducible *Prochlorococcus* phage P-SSM2Fd1 |
| pFd025 | Cam$^R$, ColE1 vector with aTc inducible *Z. mays* Fd3 |
| pFd007_C42A/lacI | Cam$^R$, ColE1 vector with aTc inducible *M. laminosus* Fd1-C42A mutant with constitutively expressed lacI to mimic split protein vectors |
| pFd007/lacI | Cam$^R$, ColE1 vector with aTc inducible *M. laminosus* Fd1 with constitutively expressed lacI to mimic split protein vectors |
| pNF007.9 | Cam$^R$, ColE1 vector with aTc inducible *M. laminosus* Fd$_{f1-9}$ and IPTG inducible Fd$_{f1-9}$ |
| pNF007.35 | Cam$^R$, ColE1 vector with aTc inducible *M. laminosus* Fd$_{f1-35}$ and IPTG inducible Fd$_{f1-35}$ |
| pNF007.65 | Cam$^R$, ColE1 vector with aTc inducible *M. laminosus* Fd$_{f1-65}$ and IPTG inducible Fd$_{f1-65}$ |
| pNF007.72 | Cam$^R$, ColE1 vector with aTc inducible *M. laminosus* Fd$_{f1-72}$ and IPTG inducible Fd$_{f1-72}$ |
| pSZ007.9 | Cam$^R$, ColE1 vector with aTc inducible *M. laminosus* Fd$_{f1-9}$-SZ17 and IPTG inducible SZ18-Fd$_{f1-9}$ |
| pSZ007.35 | Cam$^R$, ColE1 vector with aTc inducible *M. laminosus* Fd$_{f1-35}$-SZ17 and IPTG inducible SZ18-Fd$_{f1-35}$ |
| pSZ007.65 | Cam$^R$, ColE1 vector with aTc inducible *M. laminosus* Fd$_{f1-65}$-SZ17 and IPTG inducible SZ18-Fd$_{f1-65}$ |
| pSZ007.72 | Cam$^R$, ColE1 vector with aTc inducible *M. laminosus* Fd$_{f1-72}$-SZ17 and IPTG inducible SZ18-Fd$_{f1-72}$ |
| pSZ007.9(-S17) | Cam$^R$, ColE1 vector with aTc inducible *M. laminosus* Fd$_{f1-9}$ and IPTG inducible SZ18-Fd$_{f1-9}$ |
| pSZ007.35(-S17) | Cam$^R$, ColE1 vector with aTc inducible *M. laminosus* Fd$_{f1-35}$ and IPTG inducible SZ18-Fd$_{f1-35}$ |
| pSZ007.65(-S17) | Cam$^R$, ColE1 vector with aTc inducible *M. laminosus* Fd$_{f1-65}$ and IPTG inducible SZ18-Fd$_{f1-65}$ |
| pSZ007.72(-S17) | Cam$^R$, ColE1 vector with aTc inducible *M. laminosus* Fd$_{f1-72}$ and IPTG inducible SZ18-Fd$_{f1-72}$ |
| pRAP007.9 | Cam$^R$, ColE1 vector with aTc inducible *M. laminosus* Fd$_{f1-9}$-FKBP and IPTG inducible FRB-Fd$_{f1-9}$ |
| pRAP007.35 | Cam$^R$, ColE1 vector with aTc inducible *M. laminosus* Fd$_{f1-35}$-FKBP and IPTG inducible FRB-Fd$_{f1-35}$ |
| pRAP007.65 | Cam$^R$, ColE1 vector with aTc inducible *M. laminosus* Fd$_{f1-65}$-FKBP and IPTG inducible FRB-Fd$_{f1-65}$ |
| pRAP007.72 | Cam$^R$, ColE1 vector with aTc inducible *M. laminosus* Fd$_{f1-72}$-FKBP and IPTG inducible FRB-Fd$_{f1-72}$ |
| pRAP007.35-F1.RFP | CamR, ColE1 vector with aTc inducible *M. laminosus* Fd$_{f1-35}$-FKBP-L12-RFP and IPTG inducible FRB-Fd$_{f1-35}$ |
| pRAP007.35-F2.RFP | Cam$^R$, ColE1 vector with aTc inducible *M. laminosus* Fd$_{f1-35}$-FKBP and IPTG inducible FRB-Fd$_{f1-35}$-L12-RFP |
| pERA007.35 | Cam$^R$, ColE1 vector with aTc inducible sFd-35-ER with econstitutively expressed lacI to mimic split protein vectors |
| pERA007.35-RFP | Cam$^R$, ColE1 vector with aTc inducible sFd-35-ER-L12-RFP with constitutively expressed lacI to mimic split protein vectors |
| pJTA007 | Kan$^R$, ColE1 pET28b derived vector with T7-lac inducible *M. laminosus* Fd1 |
| pJTA_ERA007.35 | Kan$^R$, ColE1 pET28b derived vector pET28b with T7-lac inducible sFd-35-ER |

TABLE 3

Full length multiple structure/sequence alignment of plant-type Fds used for sequence divergence profile calculation. Fasta formatted multiple structure/sequence alignment used to calculate the Fd family sequence divergence profile shown in FIGS. 25D and 28. A MSA of 60 plant-type 2Fe-2S Fds was generated using a hybrid multiple structure/sequence alignment approach. Two initial MSAs were generated, for the plant-type Fd with known structures (n = 22), an MSA was generated using the structural alignment algorithm MATT (Menke et al., 2008), and the remaining Fd lacking solved structures (n = 38) were used to generate a MSA using the sequence alignment algorithm MUSCLE (Edgar, 2014). The two MSAs were then merged using the profile-profile alignment function in MUSCLE that maintains the aligned columns from each original MSA and, as needed, inserts additional gaps.

| UniProt Accession Number | Sequence Alignment | SEQ ID NO: |
| --- | --- | --- |
| soFd1_P00221 | -------AA---YKVTLVT---P------------------<br>----------TGNVEFQCPDDVYILDAAEEEGID---L---<br>---PYSCRA-GSCSSCAGKLKTGSLNQDDQS----FLDDD-<br>QIDE-G---WVLTCAAYPV-SDVTIETHK----------K<br>EELTA------------------------------------ | 1 |
| sfFd1_P56408 | ------------YKVTLKT---P------------------<br>----------SGEETIECPEDTYILDAAEEAGLD---L---<br>---PYSCRA-GACSSCAGKVESGEVDQSDQS----FLDDA-<br>QMGK-G---FVLTCVAYPT-SDVTILTHQ----------E<br>AALY------------------------------------- | 2 |
| nspFd1_P0A3C8 | -------AT---FKVTLINE-AE------------------<br>----------GTKHEIEVPDDEYILDAAEEQGYD---L---<br>---PFSCRA-GACSTCAGKLVSGTVDQSDQS----FLDDD-<br>QIEA-G---YVLTCVAYPT-SDVVIQTHK----------E<br>EDLY------------------------------------- | 3 |

TABLE 3-continued

Full length multiple structure/sequence alignment of plant-type Fds used for sequence divergence profile calculation. Fasta formatted multiple structure/sequence alignment used to calculate the Fd family sequence divergence profile shown in FIGS. 25D and 28. A MSA of 60 plant-type 2Fe-2S Fds was generated using a hybrid multiple structure/sequence alignment approach. Two initial MSAs were generated, for the plant-type Fd with known structures (n = 22), an MSA was generated using the structural alignment algorithm MATT (Menke et al., 2008), and the remaining Fd lacking solved structures (n = 38) were used to generate a MSA using the sequence alignment algorithm MUSCLE (Edgar, 2014). The two MSAs were then merged using the profile-profile alignment function in MUSCLE that maintains the aligned columns from each original MSA and, as needed, inserts additional gaps.

| UniProt Accession Number | Sequence Alignment | SEQ ID NO: |
|---|---|---|
| hmFd1_P00217 | ------------PTVEYLN-YEVVDDNGWDMYDDDVFGEAS DMDLDD----EDYGSLEVNEGEYILEAAEAQGYD---W--- ---PFSCRA-GACANCAAIVLEGDIDMDQQ----ILSDE- EVEDKN---VRLTCIGSPDADEVKIVYNA----------K HLDY-LQNRVI----------------------------- | 4 |
| hasFd1_P00216 | ------------PTVEYLN-YETLDDQGWDMDDDDLFEKAA DAGLDG----EDYGTMEVAEGEYILEAAEAQGYD---W--- ---PFSCRA-GACANCASIVKEGEIDMDQQ----ILSDE- EVEEKD---VRLTCIGSPAADEVKIVYNA----------X HLDY-L-----QNRVI------------------------ | 5 |
| nspFd2_P11053 | --------AS---YQVRLINK--K----------------- ------Q---DIDTTIEIDEETTILDGAEENGIE---L--- ---PFSCHS-GSCSSCVGKVVEGEVDQSDQI----FLDDE- QMGK-G---FALLCVTYPR-SNCTIKTHQ-----------E PYLA------------------------------------ | 6 |
| eaFd1_P00235 | --------A---YKTVLKT---P------------------ ----------SGEFTLDVPEGTTILDAAEEAGYD---L--- ---PFSCRA-GACSSCLGKVVSGSVDESEGS----FLDDG- QMEE-G---FVLTCIAIPE-SDLVIETHK-----------E EELF------------------------------------ | 7 |
| pfaFd1_Q8IED5 | -------AF---YNITLRT---N------------------ ----------DGEKKIECNEDEYILDASERQNVE---L--- ---PYSCRG-GSCSTCAAKLVEGEVDNDDQS----YLDEE- QIKK-K---YILLCTCYPK-SDCVIETHK-----------E DELH-D----------M----------------------- | 8 |
| s6803Fd1_P27320 | -------MAS--YTVKLIT---P------------------ ----------DGESSIECSDDTYILDAAEEAGLD---L--- ---PYSCRA-GACSTCAGKITAGSVDQSDQS----FLDDD- QIEA-G---YVLTCVAYPT-SDCTIETHK-----------E EDL-------------Y----------------------- | 9 |
| pcFd1_Q7M1S1 | -------AT---YNVKLIT---P ----------------- ----------DGEVEFKCDDDVYVLDQAEEEGID---I--- ---PYSCRA-GSCSSCAGKVVSGSIDQSDQS----FLDDE- QMDA-G---YVLTCHAYPT-SDVVIETHK-----------E EEIV------------------------------------ | 10 |
| mlFd1_P00248 | -------AT---YKVTLIN--------------------- --------EAEGLNKTIEVPDDQYILDAAEEAGID---L--- ---PYSCRA-GACSTCAGKLISGTVDQSDQS----FLDDD- QIEA-G---YVLTCVAYPT-SDCVIETHK-----------E EELY------------------------------------ | 11 |
| teFd1_P0A3C9 | -------AT---YKVTLVR---PD----------------- ----------GSETTIDVPEDEYI-LDVA-EEQGLD-L--- ---PFSCRA-GACSTCAGKLLEG-EVDQSD-QSF-LDDD- QIEK-G---FVLTCVAYPR-SDCKILTNQ-----------E EEL-Y------------------------------------ | 12 |
| eaFd2_P00237 | --------A---YKVTLKT---P------------------ ----------DGDITFDVEPGERLIDIGS-EKAD---L--- ---PLSCQA-GACSTCLGKIVSGTVDQSEGS----FLDDE- QIEQ-G---YVLTCIAIPE-SDVVIETHK-----------E DEL-------------------------------------- | 13 |

TABLE 3-continued

Full length multiple structure/sequence alignment of plant-type
Fds used for sequence divergence profile calculation. Fasta
formatted multiple structure/sequence alignment used to calculate
the Fd family sequence divergence profile shown in FIGS. 25D and
28. A MSA of 60 plant-type 2Fe-2S Fds was generated using a hybrid
multiple structure/sequence alignment approach. Two initial MSAs
were generated, for the plant-type Fd with known structures
(n = 22), an MSA was generated using the structural alignment
algorithm MATT (Menke et al., 2008), and the remaining Fd lacking
solved structures (n = 38) were used to generate a MSA using the
sequence alignment algorithm MUSCLE (Edgar, 2014). The two MSAs were
then merged using the profile-profile alignment function in MUSCLE
that maintains the aligned columns from each original MSA and, as
needed, inserts additional gaps.

| UniProt Accession Number | Sequence Alignment | SEQ ID NO: |
|---|---|---|
| crFd1_P07839 | --------M---YKVTLKT---P------------------<br>----------SGDKTIECPADTYILDAAE-EAGL--DL---<br>---PYSCRA-GACSSCAGKVAAGTVDQSDQ-----SFLDDA<br>QMGN-G---FVLTCVAYPT-SDCTIQTHQ-----------E<br>EALY-----------E-NLYFQ------------------ | 14 |
| cmFd1_Q85FT5 | --------M---YKIQLVNQ--K------------------<br>------E---GIDVTIQCAGDQYILDAAEEQGVD---L---<br>---PYSCRA-GACSTCAGKLVKGSVDQSDQS----FLDED-<br>QISK-G---FILTCVAYPT-SDCVIQTHQ-----------E<br>EALY------------------------------------- | 15 |
| asFd1_P00250 | -------AS---YKVTLKT---P------------------<br>----------DGDNVITVPDDEYILDVAEEQGLD---L---<br>---PYSCRA-GACSTCAGKLVSGPAPDQSDQ---SFLDDD-<br>QIQA-G---YILTCVAYPT-GDCVIETHK-----------E<br>EALY------------------------------------- | 16 |
| zmFd1_P27787 | -------AT---YNVKLIT---P------------------<br>----------EGEVELQVPDDVYILDQAEEDGID---L---<br>---PYSCRA-GSCSSCAGKVVSGSVDQSDQS----YLDDG-<br>QIAD-G---WVLTCHAYPT-SDVVIETHK-----------E<br>EELT------------------GA----------------- | 17 |
| lbFd1_Q51577 | -------PS---FKVTLINE--T------------------<br>------E---GLNTTIEVPDDEYILDAAEEQGID---L---<br>---PYSCRA-GACSTCAGKITAGTVDQSDQS----FLDDD-<br>QIQA-G---YVLTCVAYPT-SDCTILTHQ-----------E<br>EDLY------------------------------------- | 18 |
| apFd1_P00246 | --------A-T-YKVTLINE--A------------------<br>------E---GINETIDCDDDTYILDAAEEAGLD---L---<br>---PYSCRA-GACSTCAGTITSGTIDQSDQS----FLDDD-<br>QIEA-G---YVLTCVAYPT-SDCTIKTHQ-----------E<br>EGLY------------------------------------- | 19 |
| crFd2_Q2HZ25 | --------M---FKVTFKT---P------------------<br>----------KGEKTIDVEADKYLLDAAEEAGMD---L---<br>---PYSCRS-GGCSTCCGKLESGTVDQSDQN----MLDED-<br>QLKQ-G---FVLTCVAYPT-SDIVILTDQ-----------E<br>SKLP--I-----------------GGSENLYFQ-------- | 20 |
| atFd2_P16972 | -------MA--TYKVKFIT---P------------------<br>----------EGELEVECDDDVYVLDAAEEAGID---L---<br>---PYSCRA-GSCSSCAGKVVSGSVDQSDQS----FLDDE-<br>QIGE-G---FVLTCAAYPT-SDVTIETHK-----------E<br>EAIM-L--------------------------EHHHHHH | 21 |
| pmpFd4_Q7V2Y3 | -------------IIRFIR---E------------------<br>------------GIDIECKPGENLRELVIREKLQ---LYGL<br>KGILGNCGGVGQCSTCFVSVEGGAKNSL---SPLTSVEEE-<br>KLNN-RPDNWRLACQTLIN-SSAVILTKP-----------Q<br>SPPSNLKDLKESAESKKLPR--------------------- | 22 |
| ppFd5_Q53527 | ---------PTVFEITVRP---D------------------<br>------------GESFVCQPQQSVLRAMEAQNKH---CL--<br>---PVGCRG-GGCGLCKVRVLTGDYECGRMSC--KHVPVE-<br>AREQ-G---YALACRLFAR-SDLCIERYS-------KPCYE<br>NTVDPQQREKVTS--------------------------- | 23 |

TABLE 3-continued

Full length multiple structure/sequence alignment of plant-type
Fds used for sequence divergence profile calculation. Fasta
formatted multiple structure/sequence alignment used to calculate
the Fd family sequence divergence profile shown in FIGS. 25D and
28. A MSA of 60 plant-type 2Fe-2S Fds was generated using a hybrid
multiple structure/sequence alignment approach. Two initial MSAs
were generated, for the plant-type Fd with known structures
(n = 22), an MSA was generated using the structural alignment
algorithm MATT (Menke et al., 2008), and the remaining Fd lacking
solved structures (n = 38) were used to generate a MSA using the
sequence alignment algorithm MUSCLE (Edgar, 2014). The two MSAs were
then merged using the profile-profile alignment function in MUSCLE
that maintains the aligned columns from each original MSA and, as
needed, inserts additional gaps.

| UniProt Accession Number | Sequence Alignment | SEQ ID NO: |
|---|---|---|
| ppFd3_P23103 | --------NSAGYEVFEVL---S------------------<br>------------GQSFRCAEGQSVLRAMEAQGKR----CI--<br>---PVGCRG-GGCGLCRVRVLSGAYRSGRMSR--GHVPAK-<br>AAAE-A---LALACQVFPQ-TDLTIEYFR-----HVGGNKP<br>DNMNYEEVTS------------------------------- | 24 |
| ppFd6_Q52176 | --------SSPPFQVHETN---S------------------<br>------------GQSFTCRPDQSVLRAMEEQGKR----CV--<br>---PVGCRG-GGCGLCKVRVLSGDYQCGRMSC--SQVPPE-<br>AGEQ-G---LALACQLYPR-ADLYIESLR-----------Q<br>VRSNP----------------------------------- | 25 |
| ppFd4_Q52061 | --------NRAGYEIRETV---S------------------<br>------------GQTFRCLPDQSVLSAMEQQGKR----CV--<br>---PVGCRG-GGCGLCKVRVLSGTYQCHKMSC--NHVPPE-<br>AAKQ-G---LALACQLFPQ-TDLNIECLRRQGPGDHNNKNQ<br>QEVSS----------------------------------- | 26 |
| mcFd1_P22868 | --------MQRVHTITAVT---E-D----------------<br>----------GESLRFECRSDEDVITAALRQNIF---L----<br>---MSSCRE-GGCATCKALCSEGDYDLKG--CSVQALPPE-<br>EEEE-G---LVLLCRTYPK-TDLEIELPY-----------T<br>H--------------------------------------- | 27 |
| crFd3_Q2HZ24 | ------------YKVTFVG---A-D----------------<br>----------GETREISCPDNQYILDAAEAQGLD---L----<br>---PATCRG-GICGACVARVAKGTIDPSDIADLTFTLDEE-<br>EQAK-G---MALLCMTRAT-SDLTLETQS-------------<br>DWGYSLGVGEWKGATGKFSSRPEPTMGKGWAELQK------ | 28 |
| crFd5_Q2HZ22 | ------------FQVTLRM---P-S----------------<br>----------GKTKTMEVGPDEALFDAVERYDVD---L----<br>---PYLCRT-GTCGTCAGRVQEGQVELKG--Q--HILDPD-<br>QVKA-G---FILMCSAYPR-SDCTILTHQ-----------E<br>ERLHTCEYGKHQ---------------------------- | 29 |
| crFd4_Q2HZ23 | ------------YKISLTH-----E----------------<br>----------GKQVDLAVPEGESILSVALDKGLD---L----<br>---PHDCKL-GVCMTCPAKLVSGTVDASG-----SMLSDD-<br>VAEK-G---YTLLCVAVPK-SDCQVKTIS-----------E<br>DELLDMQLMTSQ---------------------------- | 30 |
| s6803Fd4_P74449 | ---------GAIYSVNLVN---PAT----------------<br>----------GSDVTIEVAEDELILEAAENQGLD---L----<br>---PYSCRA-ASCVACAGRLLEGTVEHTDKGS--DFLKPE-<br>ELAA-G---CVLLCAAYAT-SDCKILTHQ-----------E<br>EALFG----------------------------------- | 31 |
| atFd4_Q9FIA7 | -------AKES-RKVKLIS---P-E----------------<br>----------GEEQEIEGNEDCCILESAENGALE---L----<br>---PYSCRS-GTCGTCCGKLVSGKVDQSL--G--SFLEEE-<br>QIQK-G---YILTCIALPL-EDCVVYTHK-----------Q<br>SDLI------------------------------------ | 32 |
| tgFd1_Q8MPF8 | ---------LF-HRIKLQT---P-D ---------------<br>----------GETKELECAEDEYILDAAEAAGIE---L----<br>---PYSCRG-GSCSTCAGKLLVGSVDGSE--Q--VYLDDA-<br>QQKK-G---YVLLCTAYPK-EDCTILTHQ-----------E<br>DQLHSEGGDE------------------------------ | 33 |

TABLE 3-continued

Full length multiple structure/sequence alignment of plant-type Fds used for sequence divergence profile calculation. Fasta formatted multiple structure/sequence alignment used to calculate the Fd family sequence divergence profile shown in FIGS. 25D and 28. A MSA of 60 plant-type 2Fe-2S Fds was generated using a hybrid multiple structure/sequence alignment approach. Two initial MSAs were generated, for the plant-type Fd with known structures (n = 22), an MSA was generated using the structural alignment algorithm MATT (Menke et al., 2008), and the remaining Fd lacking solved structures (n = 38) were used to generate a MSA using the sequence alignment algorithm MUSCLE (Edgar, 2014). The two MSAs were then merged using the profile-profile alignment function in MUSCLE that maintains the aligned columns from each original MSA and, as needed, inserts additional gaps.

| UniProt Accession Number | Sequence Alignment | SEQ ID NO: |
|---|---|---|
| avaFd2_P46046 | ---------AT-YQVRLIS---KKE----------------<br>----------NIDTTIEIDEETTILDGAEENGIE---L---<br>---PFSCHS-GSCSSCVGKVVEGEVDQSD--Q--IFLDDE-<br>QVGK-G---FALLCVTYPR-SNCTIKTHQ----------E<br>PYLA------------------------------------ | 34 |
| avaFd4_P46047 | ---------TT-YQVRLIN---KKR----------------<br>----------AIDITIPVDENTTILDAAEQQDIE---L---<br>---PFSCQS-GSCSSCVAKVVEGEVDQSE--Q--VFLDEE-<br>QMAK-G---FIVLCVSYPR-SDCTIRTHQ----------E<br>PYLV------------------------------------ | 35 |
| PSSM2Fd1_Q58M74 | ---------A--YSITLRS---P-D----------------<br>----------GAEEVVQCEEDQYILEAAEDAGLD---M---<br>---PSSCRA-GACSACLGKVLEGSVNNEE--Q--SFLDDD-<br>QLEE-G---WSLLCVAMPQ-SDCVILTEQ----------E<br>DNLD------------------------------------ | 36 |
| Syn33Fd1_E3SQZ8 | ---------T--YNVTLQS---P-D----------------<br>----------GTEAVIQCEADQYILEAAEEAGVD---L---<br>---PSSCKA-GACSACAGKLVSGTVDNEE--Q--SFLDDD-<br>QLED-G---WVLTCVAYPT-SDCVILTEQ----------E<br>ENL------------------------------------- | 37 |
| puFd1_P00242 | ---------AD-YKIHLVS---KEE----------------<br>----------GIDVTFDCSEDTYILDAAEEEGIE---L---<br>---PYSCRA-GACSTCAGKVTEGTVDQSD--Q--SFLDDE-<br>QMLK-G---YVLTCIAYPE-SDCTILTHV----------E<br>QELY------------------------------------ | 38 |
| atFd3_Q9ZQG8 | ANSGGATMSAV-YKVKLLG---P-D----------------<br>----------GQEDEFEVQDDQYILDAAEEAGVD---L---<br>---PYSCRA-GACSTCAGQIVSGNVDQSD--G--SFLEDS-<br>HLEK-G---YVLTCVAYPQ-SDCVIHTHK----------E<br>TELF------------------------------------ | 39 |
| zmFd3_P27788 | ---------AV-YKVKLVG---P-E----------------<br>----------GEEHEFDAPDDAYILDAAETAGVE---L---<br>---PYSCRA-GACSTCAGKIESGSVDQSD--G--SFLDDG-<br>QQEE-G---YVLTCVSYPK-SDCVIHTHK----------E<br>GDLY------------------------------------ | 40 |
| zmFd6_P94044 | ---------VL-HKVKLVG---P-D----------------<br>----------GTEHEFEAPDDTYILEAAETAGVE---L---<br>---PFSCRA-GSCSTCAGRMSAGEVDQSE--G--SFLDDG-<br>QMAE-G---YLLTCISYPK-ADCVIHTHK----------E<br>EDLY------------------------------------ | 41 |
| dmuFd2_P00249 | ---------AT-YKVRLFN---AAE----------------<br>----------GLDETIEVPDDEYILDAAEEAGLD---L---<br>---PFSCRS-GSCSSCNGILKKGTVDQSD--Q--NFLDDD-<br>QIAA-G---NVLTCVAYPT-SNCEIETHR----------E<br>DAIA------------------------------------ | 42 |
| s7002Fd1_P31965 | ------------YKVTLIT---P-D----------------<br>----------G-EVSYDAPDDEYILDSAGDAGYD---L---<br>---PASCRA-GACSTCAGKIVSGTVDQSE--Q--SFLDDD-<br>QIEA-G---YVLTCIAYPQ-SDVTIETNK----------E<br>E--------------------------------------- | 43 |

TABLE 3-continued

Full length multiple structure/sequence alignment of plant-type
Fds used for sequence divergence profile calculation. Fasta
formatted multiple structure/sequence alignment used to calculate
the Fd family sequence divergence profile shown in FIGS. 25D and
28. A MSA of 60 plant-type 2Fe-2S Fds was generated using a hybrid
multiple structure/sequence alignment approach. Two initial MSAs
were generated, for the plant-type Fd with known structures
(n = 22), an MSA was generated using the structural alignment
algorithm MATT (Menke et al., 2008), and the remaining Fd lacking
solved structures (n = 38) were used to generate a MSA using the
sequence alignment algorithm MUSCLE (Edgar, 2014). The two MSAs were
then merged using the profile-profile alignment function in MUSCLE
that maintains the aligned columns from each original MSA and, as
needed, inserts additional gaps.

| UniProt Accession Number | Sequence Alignment | SEQ ID NO: |
|---|---|---|
| pmFd1_Q7TUS8 | ---------AS-YKVTLIS---ESE----------------<br>----------GLNKTIEVPDDQYILDAAEEQGID---L---<br>---PYSCRA-GACSTCAGKLTGGSVDQSD--Q--SFLDDD-<br>QLEA-G---FVLTCVAYPT-SDCTIKTHA----------E<br>EELY----------------------------------- | 44 |
| pmpFd2_Q7V0B6 | ---------AS-YKVTLIS---ESE----------------<br>----------GLNSTIEVPDDQYILDAAEEQGVD---L---<br>---PYSCRA-GACSTCAGKITSGTVDQSD--Q--SFLDDD-<br>QLEA-G---FVLTCVAYPS-SDVTITTHA----------E<br>EELY----------------------------------- | 45 |
| dmuFd1_P00252 | ---------ATVYKVTLVD---Q-E----------------<br>----------GTETTIDVPDDEYILDIAEDQGLD---L---<br>---PYSCRA-GACSTCAGKIVSGTVDQSD--Q--SFLDDD-<br>QIEK-G---YVLTCVAYPT-SDLKIETHK----------E<br>EDLY----------------------------------- | 46 |
| seFd1_P0A3D2 | ---------AT-YKVTLVN---AAE ---------------<br>----------GLNTTIDVADDTYILDAAEEQGID---L---<br>---PYSCRA-GACSTCAGKVVSGTVDQSD--Q--SFLDDD-<br>QIAA-G---FVLTCVAYPT-SDVTIETHK----------E<br>EDLY----------------------------------- | 47 |
| avaFd1_P00254 | ---------AT-FKVTLIN---EAE----------------<br>----------GTSNTIDVPDDEYILDAAEEQGYD---L---<br>---PFSCRA-GACSTCAGKLVSGTVDQSD--Q--SFLDDD-<br>QIEA-G---YVLTCVAYPT-SDVTIQTHK----------E<br>EDLY----------------------------------- | 48 |
| dsFd1_P68165 | ---------AT-YKVKLVT---P-D----------------<br>----------G-PVEFNCPDDVYILDQAEEEGHD---L---<br>---PYSCRA-GSCSSCAGKVTAGTVDQSD--G--NYLDDD-<br>QMAD-G---FVLTCVAYPQ-SDVTIETHK----------E<br>EELTG---------------------------------- | 49 |
| amFd1_P81372 | ---------AT-YKVKLVT---P-Q----------------<br>----------G-QQEFDCPDDVYILDQAEEEGID---L---<br>---PYSCRA-GSCSSCAGKVKQGEVDQSD--G--SFLDDE-<br>QMEQ-G---WVLTCVAFPT-SDVVIETHK----------E<br>EELTA----------------------------------- | 50 |
| atFd1_O04090 | ---------AT-YKVKFIT---P-E----------------<br>----------G-EQEVECEEDVYVLDAAEEAGLD---L---<br>---PYSCRA-GSCSSCAGKVVSGSIDQSD--Q--SFLDDE-<br>QMSE-G---YVLTCVAYPT-SDVVIETHK----------E<br>EAIM----------------------------------- | 51 |
| zmFd5_P27789 | ---------AT-YNVKLIT---P-E----------------<br>----------G-EVELQVPDDVYILDYAEEEGID---L---<br>---PYSCRA-GSCSSCAGKVVSGSLDQSD--Q--SFLDDS-<br>QVAD-G---WVLTCVAYPT-SDVVIETHK----------E<br>DDLIS----------------------------------- | 52 |
| zmFd2_O80429 | ---------AT-YNVKLIT---P-E----------------<br>----------G-EVELQVPDDVYILDFAEEEGID---L---<br>---PFSCRA-GSCSSCAGKVVSGSVDQSD--Q--SFLNDN-<br>QVAD-G---WVLTCAAYPT-SDVVIETHK----------E<br>DDLL----------------------------------- | 53 |

TABLE 3-continued

Full length multiple structure/sequence alignment of plant-type
Fds used for sequence divergence profile calculation. Fasta
formatted multiple structure/sequence alignment used to calculate
the Fd family sequence divergence profile shown in FIGS. 25D and
28. A MSA of 60 plant-type 2Fe-2S Fds was generated using a hybrid
multiple structure/sequence alignment approach. Two initial MSAs
were generated, for the plant-type Fd with known structures
(n = 22), an MSA was generated using the structural alignment
algorithm MATT (Menke et al., 2008), and the remaining Fd lacking
solved structures (n = 38) were used to generate a MSA using the
sequence alignment algorithm MUSCLE (Edgar, 2014). The two MSAs were
then merged using the profile-profile alignment function in MUSCLE
that maintains the aligned columns from each original MSA and, as
needed, inserts additional gaps.

| UniProt Accession Number | Sequence Alignment | SEQ ID NO: |
|---|---|---|
| pmpFd3_Q7V039 | ---------SE-YNIKVEL-----E---------------<br>----------KKTYVFLCPEDQDIISAAKANGID---L---<br>---PSSCCS-GVCTSCASMVIDGSVEQED--A--MGLNDD-<br>LKEK-G---FALLCVAYPK-SDLHIIIGD---------EVE<br>DNLYNNQFGKYQI--------------------------- | 54 |
| seFd6_Q31RE9 | ---------AT-YQVEVIY-----Q---------------<br>----------GQSQTFTADSDQSVLDSAQAAGVD---L---<br>---PASCLT-GVCTTCAARILSGEVDQPD--A--MGVGPE-<br>PAKQ-G---YTLLCVAYPR-SDLKIETHK----------E<br>DELYALQFGQPG---------------------------- | 55 |
| s6803Fd3_P73388 | ---------VNTYTAEIQH-----Q---------------<br>----------GQTYTISVPEDKTVLQAADDEGIQ---L---<br>---PTSCGA-GVCTTCAALITEGTAEQAD--G--MGVSAE-<br>LQAE-G---YALLCVAYPR-SDLKIITEK----------E<br>DEVYQRQFGGQG---------------------------- | 56 |
| crFd6_Q2HZ21 | -------------KIKIFD---HYG---------------<br>----------NQEIDVEVPEDRYILWEAEDKGLE---L---<br>---PYACRM-GCCTACAVRVKEGEVHQPE--A--LGISAE-<br>LREM-G---YALMCVGYPT-SDAVMETVS----------E<br>DEIYELQFGKYFAQQALDPNSESIERDDYALSIANMDE--- | 57 |
| pmpFd1_Q7V1H3 | ---------KKTFKVTITN---KET---------------<br>----------GKIYQENISDQEYILKEFEKKGLR---L---<br>---PFSCRN-GCCTSCAVKIISGKLDQPE--A--MGVSQD-<br>LKDK-G---YALLCVAKVI-EDIEVETTY----------Y<br>DEVYDLQFGQYFGKGKTRKAPPWEFEED------------- | 58 |
| seFd3_Q31K08 | ---------SDTYTVRIRD---RRT---------------<br>----------DEEFTVQVPPDRYILQTAEEQGYE---L---<br>---PFSCRN-GACTACAVRVLGGAIEQTE--A--MGLSAP-<br>LRQR-G---YALLCVSYPR-SDVIVETQD----------E<br>DEVYMLQFGRYFGQGKVSFGLPLDEE-------------- | 59 |
| s6803Fd2_P74159 | ---------SRSHRVLIHD---RQN---------------<br>----------EKDYSVIVSDDRYILHQAEDQGFE---L---<br>---PFSCRN-GACTACAVRVISGQIHQPE--A--MGLSPD-<br>LQRQ-G---YALLCVSYAQ-SDLEVETQD----------E<br>DEVYELQFGRYFGAGRVRLGLPLDED-------------- | 60 |

Example 1—Identifying Ferredoxin Cleavage Sites to Produce Non-Functional Fragments that Retain Metal Co-Factor Binding Natural Fds may at time dynamically control their ET through post-translational modifications. Upon Fe—S cluster oxidation, nitrogenase-protecting Fds alter their conformation and binding affinity to nitrogenase to protect from oxidative damage (Schlesier et al., 2016). Phosphorylated and calcium-bound forms of Fds were recently discovered in cyanobacteria (Angeleri et al., 2018) and *rhizobia* (Moscatiello et al., 2015), respectively. These discoveries suggest that Fd ET may also be dynamically regulated through signaling cascades, although the exact mechanisms by which these modifications affect Fd ET remain unclear. Protein design efforts have investigated whether Fd ET can be deliberately controlled. Fds have been rationally mutated using structural information (Rumpel et al., 2014) and fused to acceptor proteins to tune the relative proportions of electrons transferred to different metabolic pathways (Eilenberg et al., 2016). While these efforts have shown how changes in energy flow can arise during evolution, they have yet to yield insight into the ways that Fds acquire new allosteric functions.

Protein fragment complementation could be used to create synthetic Fds whose control over ET is regulated by environmental conditions (FIGS. 13-19). Previous studies have shown that proteins can be fragmented into polypeptides whose stable association and cooperative activities are dependent upon ligand-binding events. This has been achieved by fusing engineered fragments to pairs of proteins whose association is stabilized by ligand binding (Pelletier et al., 1998; Thomas et al., 2017), and by fusing protein fragments to the termini of ligand binding domains (Thomas et al., 2017; Guntas et al., 2005).

Figure 25A:
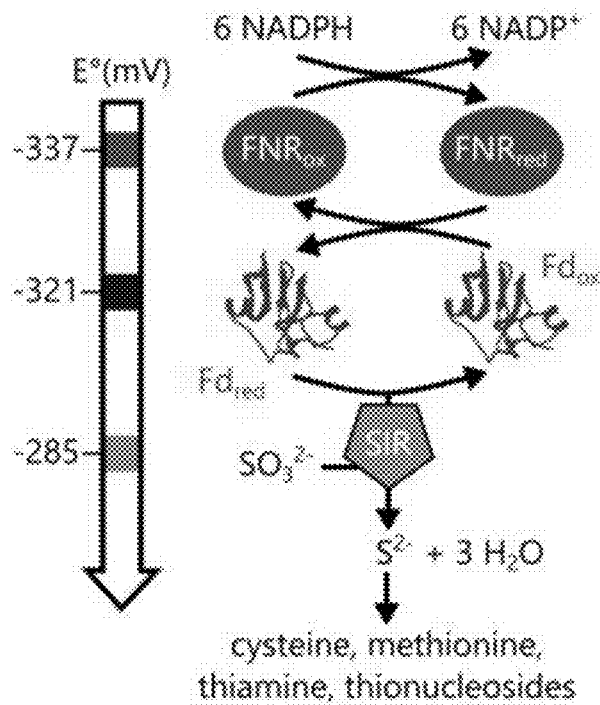
FIGS. 25A-H. Designing split Fds that transfer electrons within cells.
Figure 25B:
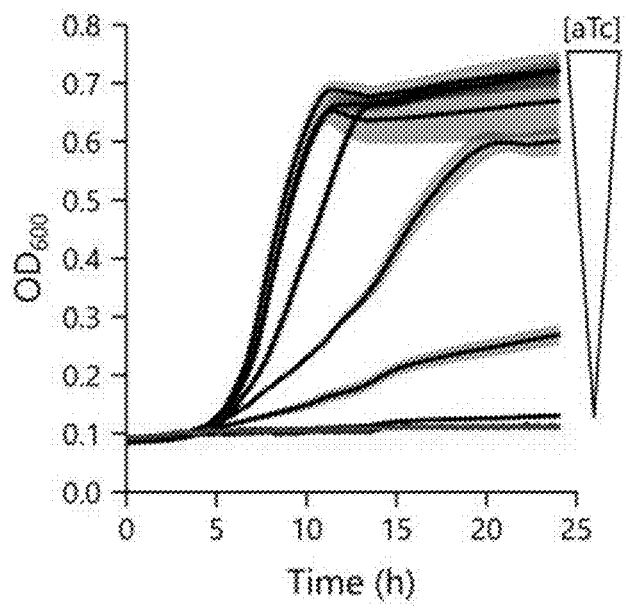

To rapidly assay ET mediated by engineered Fds, an *Escherichia coli* sulfide auxotroph (EW11; Barstow et al., 2011), which cannot grow in minimal medium containing sulfate as a sulfur source unless it expresses a synthetic ET chain consisting of a Fd-NADP+ reductase (FNR) electron donor, a Fd electron carrier, and a Fd-dependent sulfite reductase (SIR) electron acceptor, was used (FIG. 25A). Endogenous oxidoreductases were systematically removed from the genome of this strain to insulate Fd-dependent redox pathways from native redox reactions (Barstow et al., 2011). To evaluate Fd ET, *Zea mays* FNR and SIR were constitutively expressed and a TetR-repressible promoter was used to control the expression of plant-type 2Fe-2S Fds. *E. coli* EW11 cells were transformed with pairs of vectors to analyze split Fd function. The first vector expresses the e-donor (FNR) and acceptor (SIR), which cannot complement growth alone are which are constitutively expressed. This vector was used in every experiment. A second vector encoded the different split Fd variants and varied across experiments. In this vector, the expression of N-terminal fragment (F1) is regulated by TetR, such that its expression is induced when anhydrotetracycline (aTc) is added to growth medium. The C-terminal fragment (F2) is regulated by LacI, such that its expression is induced when isopropyl-β-D-thiogalactopyranoside (IPTG) is added to growth medium. See FIGS. 4-6.

With this expression strategy, the inventors can quickly assess which split Fds require two fragments to function in complementation assays by assessing growth in the presence and absence of both inducers because growth depended upon the level of anhydrotetracycline (aTc) (FIG. 25B), and thus, the amount of Fd available to mediate ET. The inventors have tested a number of constructs expressing different split Fds. For these experiments, they assessed split Fd function in the presence of a constant high concentration of aTc, and varying concentrations of IPTG, which selectively drive the distinct promoters.

Figure 25C:
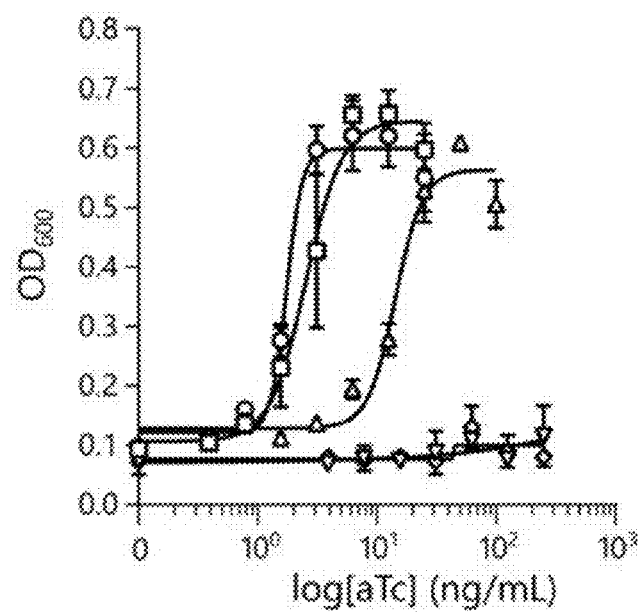

This cellular assay was used for comparing Fd activities in *Escherichia coli* through expression of a three-component redox pathway that rescues the growth of a sulfide auxotroph that cannot use sulfite as the only sulfur source. The inventors showed that auxotroph growth is rescued when it expresses an e-donor protein (Fd-NADP reductase, FNR, both bacterial and plant), *Mastigocladus laminosus* ferredoxin, and an e-acceptor (Fd-dependent sulfite reductase, SIR, both bacterial and plant). The effect of aTc on complementation by five 2Fe-2S Fds was analyzed, including plant, cyanobacterial, algal, and phage family members. *Mastigocladus laminosus* Fd (Ml-Fd) yielded half-maximal complementation at the lowest aTc concentration (FIG. 25C). This thermostable Fd, which displays optimal ET at 65° C. (Fish et al., 2005) was targeted for all subsequent design efforts to minimize the destabilizing effects of mutations, since previous studies have shown that tolerance to fission correlates with thermostability (Segall-Shapiro et al., 2011).

Figure 25D:
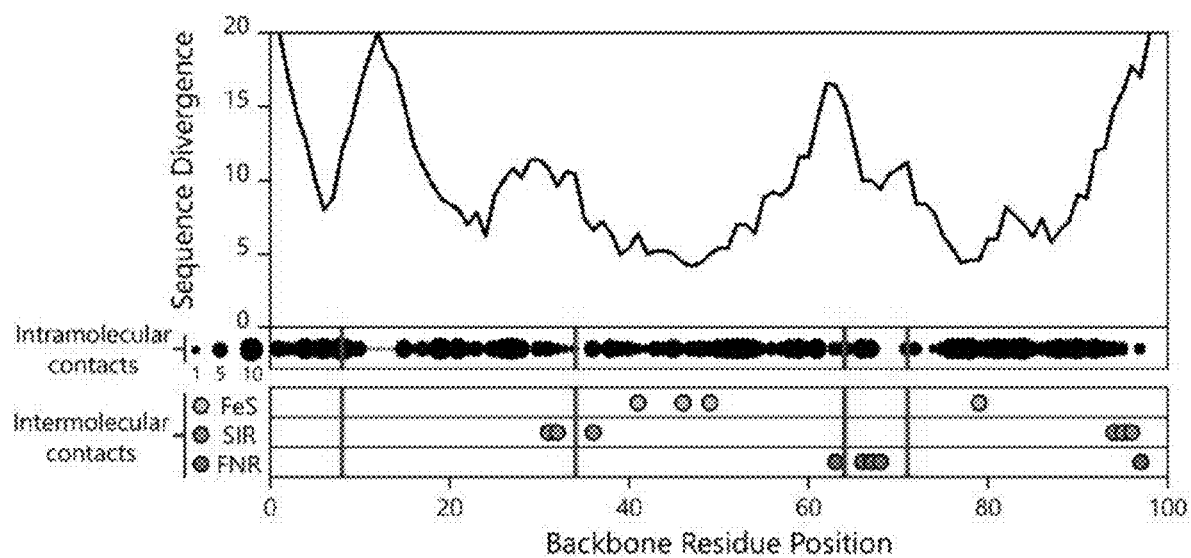

To identify backbone fission locations that are non-disruptive to Ml-Fd structure, a multiple sequence alignment of 2Fe-2S Fds was generated (FIG. 28) and the number of different amino acids at each native Ml-Fd position was calculated (FIG. 25D). Using this alignment, the inventors calculated sequence diversity at each native position in the family alignment as the number of unique amino acids that are observed ($k^*$), and they used this metric to identify potential backbone fission sites for the inventors' initial efforts. Four sites with moderate sequence divergence were targeted for backbone fission, including the peptide bonds following residues 9, 35, 65, and 72. These sites were chosen because they vary in their distances from the 2Fe-2S cluster, and they differ in the number of cofactor and partner-binding residues encoded distributed across the pair of fragments.

These initial efforts focused on plant-type Fd (1×2Fe2S) whose activities are easiest to evaluate using bacterial selection, although ongoing efforts are focused on performing the same analysis with *Clostridial* Fd (2×4Fe4S). This analysis revealed that the sequence conservation varied significantly across the Fd structure and suggested locations where Fd would be most tolerant to the large perturbations arising from the introduction of new termini generated by fission, i.e., regions with this highest $k^*$ (see FIG. 25D). The red lines indicate cut sites that were actually tested.

To analyze the tolerance of a Fd to backbone fragmentation, the inventors targeted *Mastigocladus laminosus* Fd, whose structure has been reported. They chose this Fd because it is thermostable, and because they found that after splitting is it still able to coordinate an 2Fe2S cluster.

This meant that the inventors' bacterial selection could be used to assay the function of split variants of *Mastigocladus laminosus* Fd and that LacI and TetR can be used to control expression of the different Fd fragments created for analysis. They chose *Mastigocladus laminosus* Fd as an initial starting point for fission experiments because it has high Tm>75° C., and previous studies have shown that proteins with enhanced stability display increased tolerance to backbone fission. For initial experiments, they created four rationally designed split Fd, including variants that had been fragmented after residues 9, 35, 65 and 72.

To maximize the likelihood that Fd would retain activity upon fission, the inventors expressed each split Fd as fusions to peptides that themselves readily associate. When they applied this approach to a bacteriophytochrome recently, they found that peptide fusions enhanced the folding of the protein, suggesting that this approach would help us identify Fd fragments that complement each other and recreate a functional Fd. They used the SYNZIP17 and SYNZIP18 peptides to assist with fragment complementation, which have high affinity for one another and associate to form an antiparallel coiled-coil.

The inventors found that all of their split Fds display greater complementation in the presence of 1 mM IPTG compared with that observed in the absence of IPTG. However, strong complementation was only observed with two-fragment Fds arising from backbone fragmentation after residues 35, 65 and 72. Moderate complementation was observed the Fd was observed with a fourth variant with fragmentation after residue 9. See FIGS. 5-6.

The four sites targeted for fission, which yielded active split Fds upon fusion to SYNZIP17 and SYNZIP18 peptides (FIG. 6), were created by targeting sites having $k^* \geq 9$. In the Ml-Fd structure (Fish et al., 2005), the backbone cleavage sites occur 9.5 to 18.5 Å from the 2Fe-2S cluster (FIG. 29). For two of the split Fd (sFd) proteins, sFd-9 and sFd-35, all of the cysteines that coordinate iron reside on a single polypeptide (FIG. 25D). The other split proteins, sFd-65 and sFd-72, have their iron-coordinating cysteines dispersed across the fragments, potentially requiring 2Fe-2S cluster maturation following fragment complementation. Mapping the backbone fission sites onto the Fd-SIR complex structure (Kim et al., 2016) reveals that the SIR contacting residues in these sFds are divided among the different polypeptide fragments in sFd-35, sFd-65, and sFd-72 (FIG. 30). In contrast, the FNR contacting residues in the Fd-FNR complex (Kurisu et al., 2001) are only divided among the different fragments in sFd-65 and sFd-72.

Example 2—Fusion to Interacting Proteins for Activity

The inventors have evaluated the dependence of Fd fragment complementation on the fusion to peptides that themselves associate. They compared the expression of two versions of Fd split after each split residue. First, they analyzed the activity of Fd fragments when the different fragments were fused to SYNZIP17 and SYNZIP18, peptides that associate. The inventors then made identical constructs but removed the peptide from the end of both Fd fragments. The split Fd that lacked assistance had no detectable activity indicating that this split Fd requires post-translational assistance to function. This experiment shows a third level of control, namely the association of the SYNZIP peptides, in addition to control over the two promoters.

A two-fragment Fd whose activity is switched on by a chemical, in this case rapamycin was used to stabilize the protein complex. In this case, the ternary complex of FKBP' Rapamycin' and FRB was used. As predicted, rapamycin caused the other two members of the ternary complex to associate, and that lead to association of the PEC fragments to form active PEC. While other ternary systems can be used in this same way, the inventors have developed simplified unimolecular systems, such as that shown in FIGS. 10A-B.

Figure 25E:
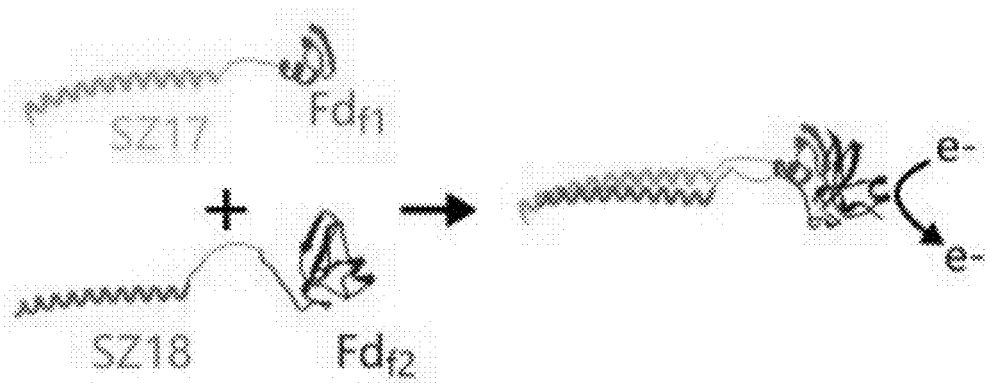
Figure 25F:
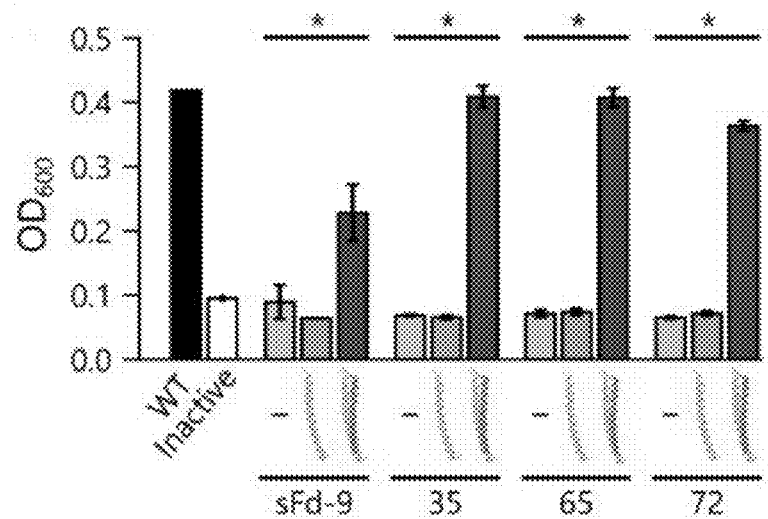
Figure 25G:
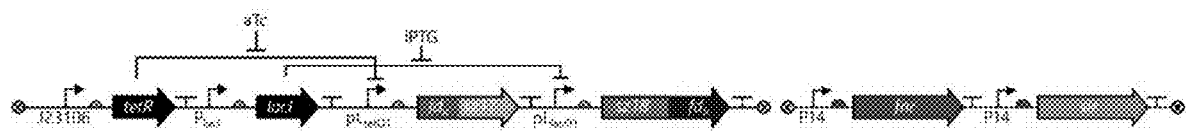
Figure 25H:
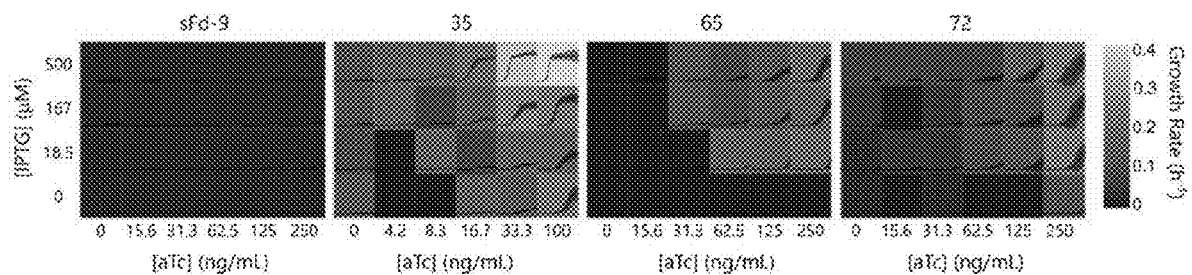

To assist with sFd ET, each pair of Fd fragments was initially expressed as fusions to SYNZIP-17 and SYNZIP-18 (FIG. 25E), synthetic peptides that stably associate to form a coiled coil (Reinke et al., 2010). When the sFds were expressed in E. coli EW11, complementation was observed with all four variants (FIG. 25F), albeit to varying extents. Removal of one or both SYNZIP peptides abolished growth in all cases, suggesting that these split proteins uniformly require assistance with fragment association for efficient ET. TetR- and LacI-repressible promoters were also used to control the expression of each Fd-fragment fusion (FIG. 25G), and complementation was analyzed over a range of aTc and isopropyl β-D-1-thiogalactopyranoside (IPTG) concentrations (FIG. 25H). sFd-35, sFd-65, and sFd-72 all functioned as a two-input AND gate to control the production of a reduced sulfur metabolite with sFd-35 exhibiting the highest tunable range.

Example 3—Using a Chemical to Switch on Fragmented Fd Activity

To determine if the activity of a fragmented Fd can be regulated by addition of a chemical, the activity of a Fd whose fragments were produced as fusions to the FKBP12 and the FKBP-binding rapamycin domain of mTOR (FRB) were analyzed. FKBP and FRB have strong affinity in the presence of rapamycin ($K_D$=12 nM) but no detectable interaction in its absence. This experiment was performed with three of the split proteins described above including the variants arising from fragmentation of the Fd after residue 35, 65, and 72. As shown in FIGS. 7-9, one of these split Fd displays rapamycin-dependent activity. The advantages of such a system include:

providing increased transcriptional control over electron flow in cells using protein electron carriers, which allows for regulation of activity using combinations of natural promoters;

allowing for post-translational control over electron flow in cells using protein electron carriers, and most importantly;

allowing for the creation of split proteins that are able to acquire their complex cofactors even when they are not able to transfer electrons so that they are poised to function upon a triggering event, such as direct binding;

upon the triggering event, the electron transfer is "fast", such as on the order of 60 seconds or less, 45 seconds or less 30 second or less, 20 seconds or less, 15 second or less, 10 seconds or less, 5 seconds or less, 4 seconds or less, 3 seconds or less, or two seconds or less, or about a second;

cells can be engineered with these protein electron carriers to conserve energy by directing electron flow to desired partner proteins under desired conditions; and increased control over electron flow in cells can be used to improve the production of synthesized products.

These constructs and methods can be used to fine tune the level of protein electron carrier proteins in the cell. Thus, they can be combined with other genetic modifications used to produce a product, and optimize the level of product formation by directly controlling the redox levels in the cell through judicious use of promoters and ligands.

Figure 26A:
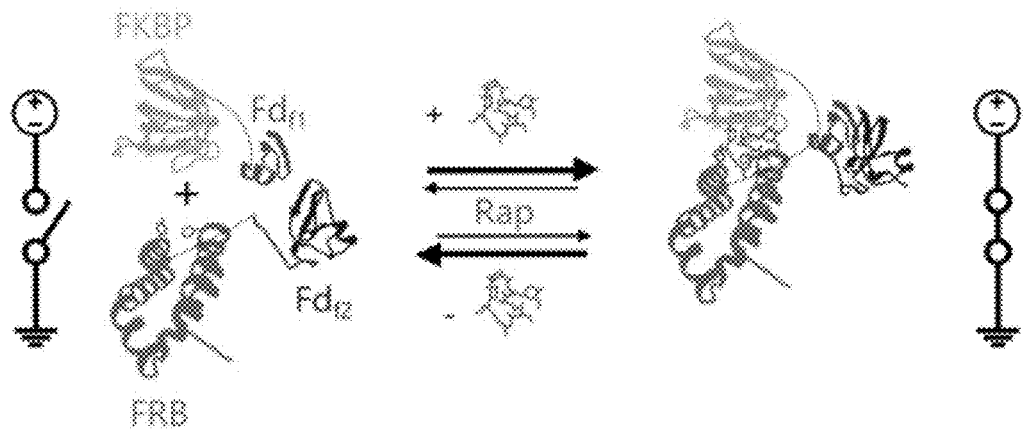
FIGS. 26A-G. Post-translation control over Fd electron transfer in cells.
Figure 26B:
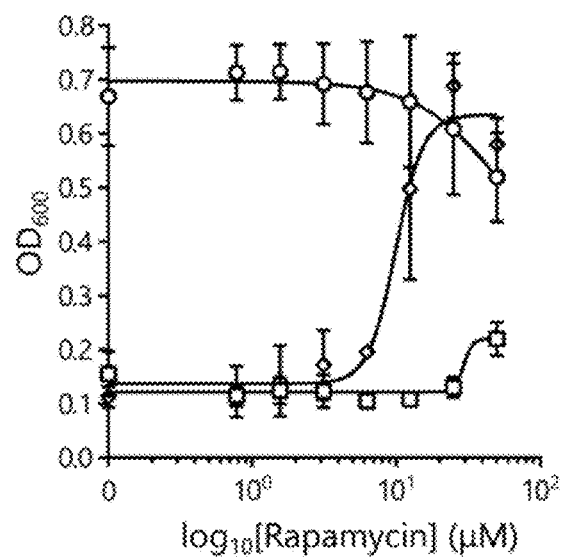

To investigate whether sFd ET can be regulated post-translationally, vectors were created for expressing the three most active split proteins as fusions to FKBP12 and the FKBP-rapamycin binding (FRB) domain of mTOR (FIG. 26A), proteins whose interaction is stabilized by rapamycin (Michnick et al., 1991) and their complementation of E. coli EW11 growth±rapamycin was assessed. These sFds were expressed using TetR- and LacI-repressible promoters (FIG. 31A), and complementation was measured using inducer concentrations that yielded maximal growth when sFds were fused to SYNZIP peptides. In the absence of rapamycin, none of the sFds complemented growth. Addition of rapamycin enhanced the growth of cells expressing sFd-35 (FIG. 26B), but not sFd-65 and sFd-72. With sFd-35, growth was dose dependent and could be tuned to a similar maximal density as cells expressing Ml-Fd.

Figure 26C:
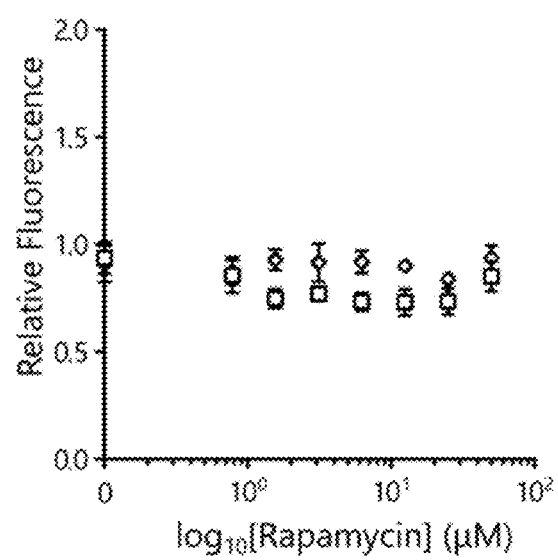
Figure 26D:
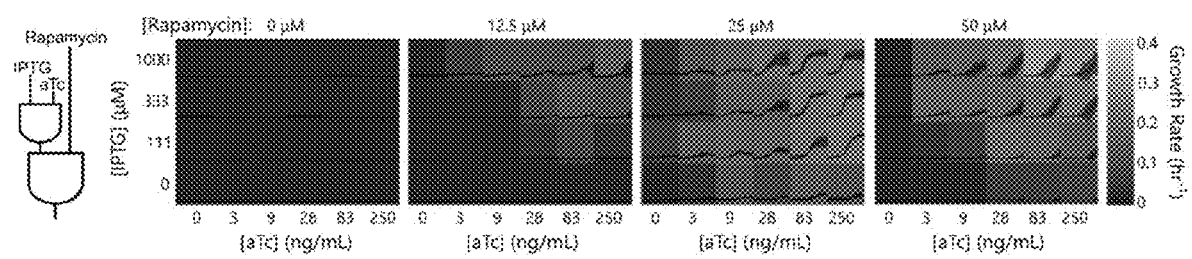

To evaluate whether rapamycin affected sFd-35 expression, rapamycin effects on protein accumulation were examined using fragments fused to red fluorescent protein (RFP). With each sFd fragment, this analysis revealed similar RFP levels in the presence and absence of rapamycin (FIG. 26C). These findings provide evidence that ET is controlled post-translationally by rapamycin stabilization of sFd fragment complex. Complementation measurements performed using different combinations of aTc, IPTG, and rapamycin revealed that sFd-35 can be used as a three-input AND gate to control ET for sulfide production and growth (FIG. 26D).

Figure 26E:
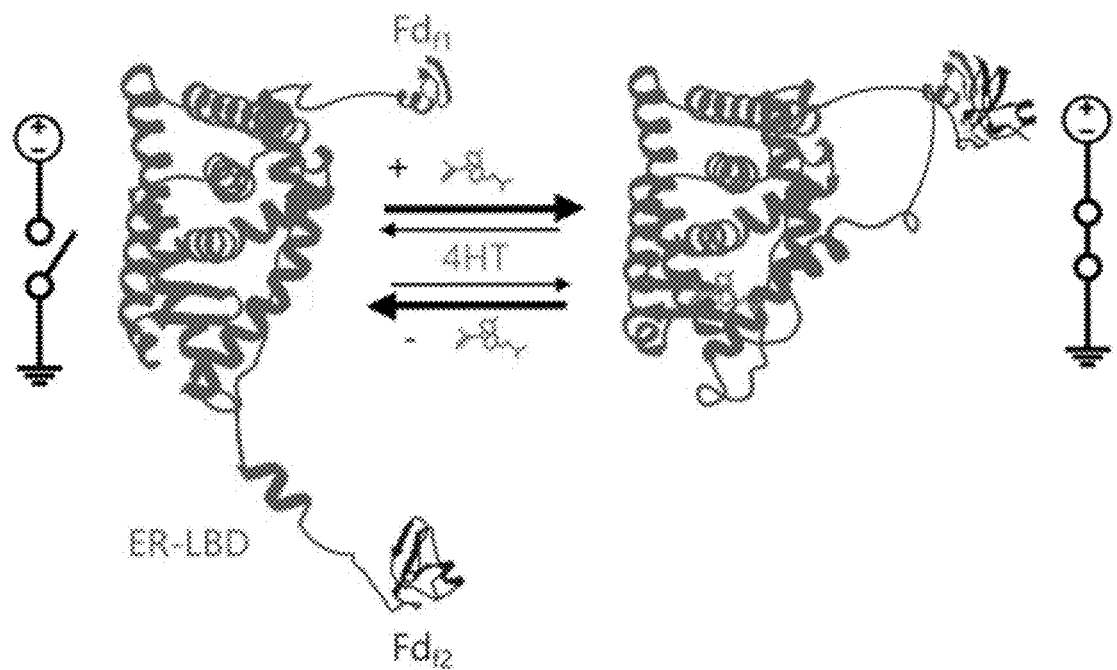

Allosteric protein switches have been engineered by fusing protein fragments to the termini of domains that undergo chemical-dependent conformational changes (Thomas et al., 2017; Guntas et al., 2005). To test whether this domain-insertion strategy can be used to diversify the chemical regulation of sFd-35, the ligand-binding domain (LBD) of the human estrogen receptor (ER) was inserted after residue 35 to create sFd-35-ER (FIG. 26E). This LBD was chosen because it undergoes a conformational change upon 4-hydroxytamoxifen (4-HT) binding that alters the proximity of the protein termini (Shiau et al., 1998). In addition, insertion of the ER-LBD into an amino acyl tRNA synthetase yields protein switches with 4-HT dependent activities (Thomas et al., 2017).

Figure 26F:
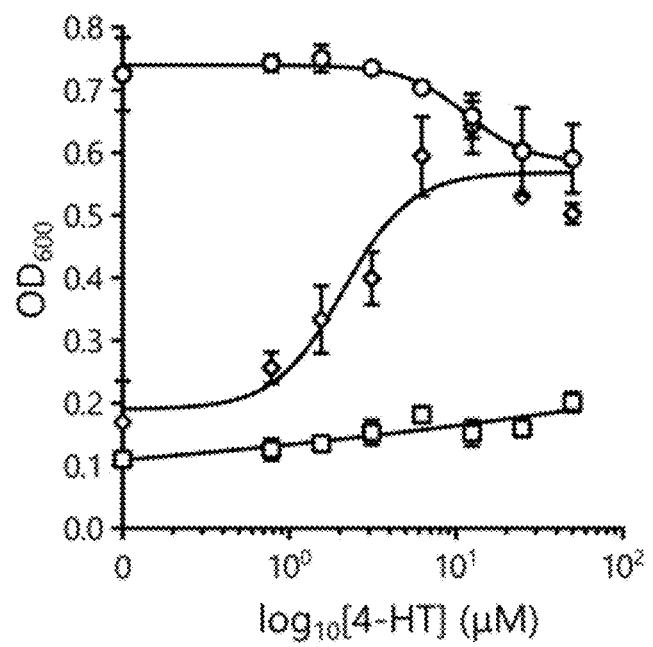
Figure 26G:
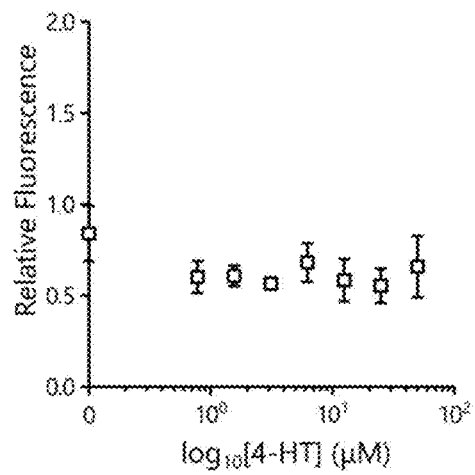

The activity of sFd-35-ER was evaluated by expressing this protein using an aTc-inducible promoter (FIG. 31B). In medium containing aTc, sFd-35-ER did not significantly enhance *E. coli* EW11 growth following a 48 hour incubation (FIG. 26F). In contrast, complementation was enhanced to Ml-Fd levels when cells were grown in the presence of aTc and 4-HT. This protein was also expressed as a fusion to RFP (sFd-35-ER-RFP) to evaluate how 4-HT affects protein expression. This analysis revealed similar expression across a range of 4-HT concentrations (FIG. 26G), providing evidence that the increased complementation arises from 4-HT effects on sFd-35-ER ET rather than increases in expression.

The ER-LBD binds two classes of estrogen receptor modulators, agonists and antagonists, which elicit distinct conformational shifts (FIGS. 32A-C) and tissue-specific responses in vivo (Shiau et al., 1998; Paige et al., 1999). To evaluate how these different modulators affect sFd-35-ER ET, sFd-35-ER growth complementation was evaluated in the presence of agonists, antagonists, and an endocrine disruptor (FIG. 32D). This analysis revealed that sFd-35-ER ET is chemically selective and activated by the ER antagonists (4-HT, raloxifene, lasoxifene) and endocrine disruptor (bisphenol-A). However, this switch is not activated by ER agonists (17β-estradiol, diethylstilbestrol, hexestrol).

To understand how Ml-Fd Fe—S cluster binding and ET are affected by domain insertion, sFd-35-ER was overexpressed in *E. coli* and purified under aerobic conditions. Recombinant sFd-35-ER was brown in color throughout the purification protocol (FIGS. 33A&B) and presented absorbance (FIG. 27A) and visible circular dichroism (CD) spectra (FIG. 27B) that were consistent with the presence of a 2Fe-2S metallocluster and similar to Ml-Fd.

To investigate if domain insertion affects the reduction potential of Ml-Fd, Ml-Fd and sFd-35-ER were characterized using protein film voltammetry. In the absence of 4-HT, the midpoint potentials of both Ml-Fd and sFd-35-ER (FIG. 27C) were −336 and −320 mV, respectively. These measurements indicate that sFd-35-ER retains a potential that is adequate for coupling NADPH oxidation by FNR (FAD $E°=-337$ mV) (Aliverti et al., 2001) to sulfite reduction by SIR ([4Fe-4S] $E°=-415$ mV, siroheme=−285 mV) (Hirasawa et al., 2004). In the presence of 4-HT, Ml-Fd presented a similar midpoint potential (−330 mV) as in the absence of ligand, while sFd-35-ER yielded a +27 mV shift in potential (−293 mV). These findings provide evidence that domain insertion can be used to create a Fd whose redox potential is tuned by chemical binding, and they suggest that this design approach could be applied to proteins with alternative 2Fe-2S cluster ligands to create switches capable of regulating ET over a range of potentials (Atkinson et al., 2016; Bak et al., 2014).

Figure 27A:
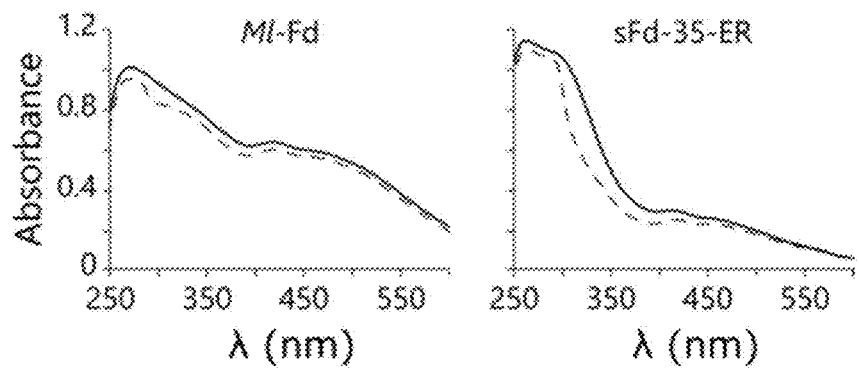
Figure 27B:
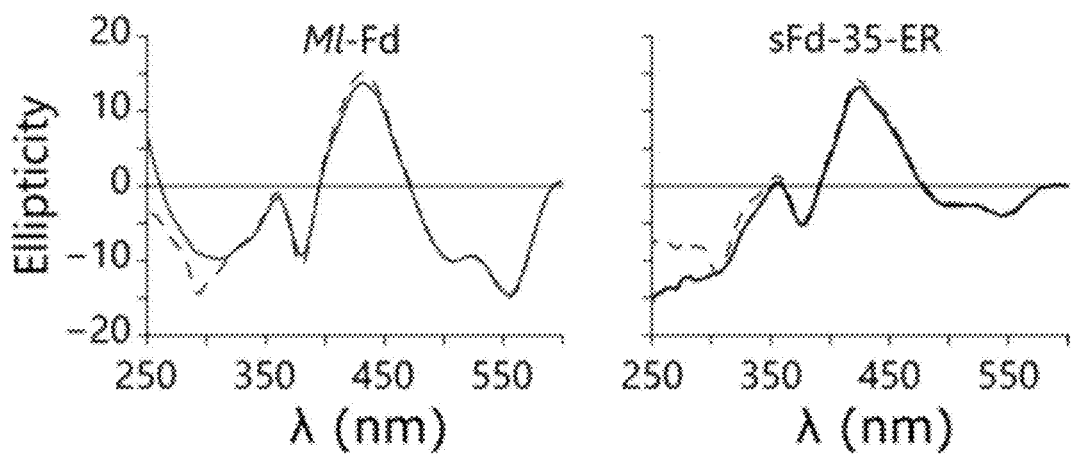
Figure 27C:
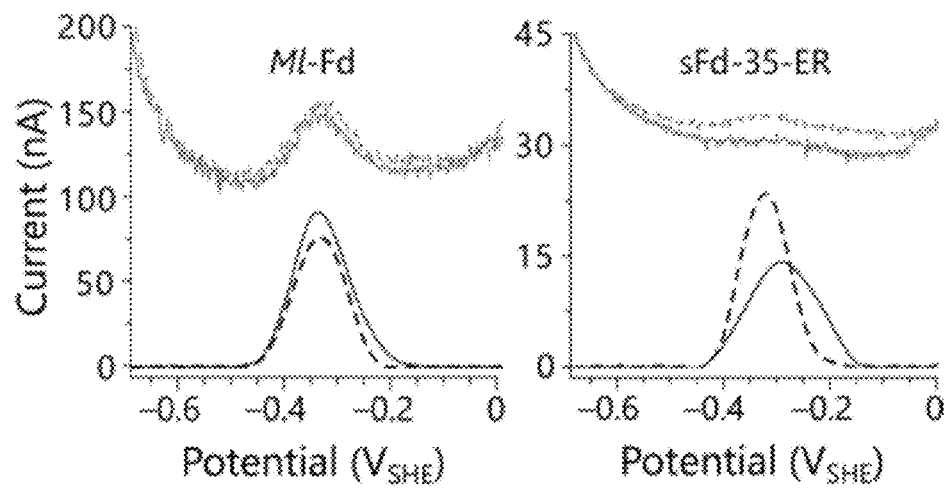
Figure 27D:
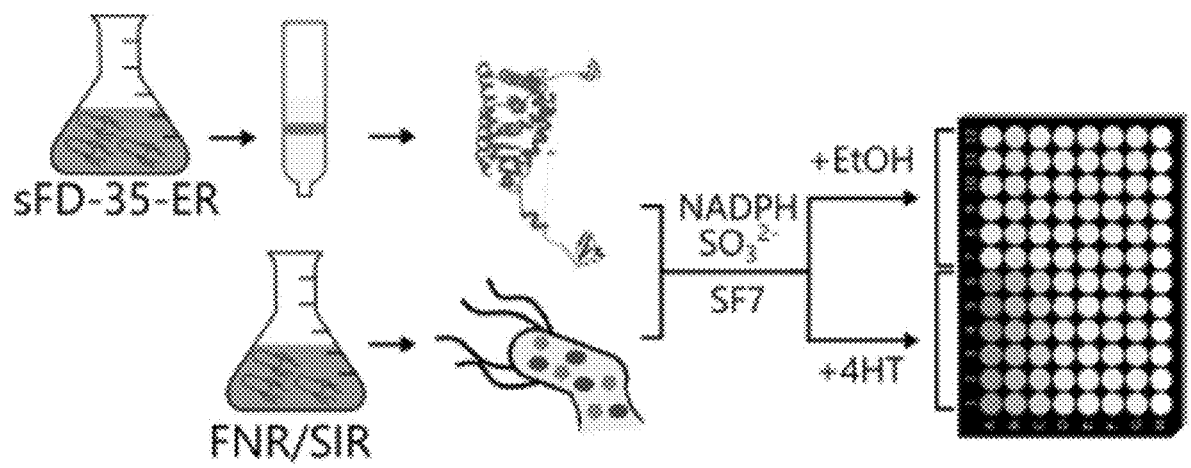
Figure 27E:
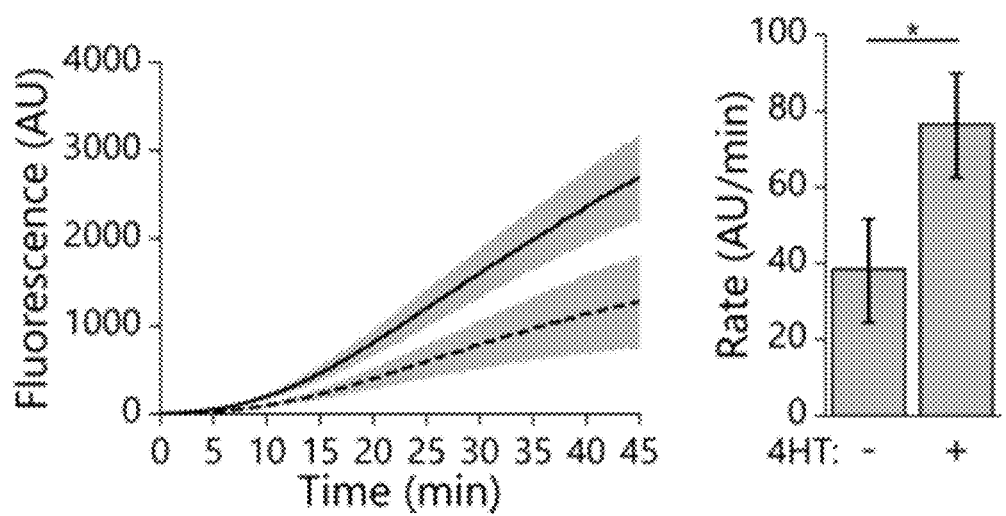

To directly demonstrate that purified sFd-35-ER functions as a switch in vitro, whether this protein could support sulfide production in lysates derived from *E. coli* EW11 expressing only FNR and SIR was examined (FIG. 27D). SIR activity was monitored in desalted cell lysates using sulfidefluor-7 (Lin et al., 2013), a fluorescent probe for hydrogen sulfide. Cell extracts derived from *E. coli* EW11 expressing FNR and SIR presented sulfide production rates that depended upon NADPH concentration (FIGS. 34A&B). To minimize this background signal, a low level of NADPH (40 μM) that did not yield large sulfide production rates over the time course of the measurements was added. With this in vitro assay, the rate of sulfide production is proportional to the concentration of Ml-Fd added to cell lysates (FIGS. 35A&B). The sulfide production rate was not enhanced by adding 4-HT alone, demonstrating that this chemical does not support ET to SIR in the absence of a Fd. Addition of purified sFd-35-ER to cell lysates containing FNR and SIR increased the sulfide production rate (FIG. 27E), indicating that this protein can mediate ET to SIR in the absence of 4-HT. However, in the presence of 4-HT, the sulfide production rate was significantly enhanced. Taken together, these measurements provide direct evidence that 4-HT regulates sulfide production by altering the conformation of sFd-35-ER and the efficiency with which it transfers electrons from FNR to SIR.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Aliverti et al., "Biochemical and crystallographic characterization of ferredoxin-NADP(+) reductase from nonphotosynthetic tissues," *Biochemistry,* 40:14501-14508, 2001.

Angeleri et al., "Interplay of SpkG kinase and the Slr0151 protein in the phosphorylation of ferredoxin 5 in *Synechocystis* sp. strain PCC 6803," *FEBS Letters,* 592:411-421, 2018.

Atkinson et al., "Cellular Assays for Ferredoxins: A Strategy for Understanding Electron Flow through Protein Carriers That Link Metabolic Pathways," *Biochemistry,* 55:7047-7064, 2016.

Bak & Elliott, "Alternative FeS cluster ligands: tuning redox potentials and chemistry," *Current Opinion in Chemical Biology,* 19:50-58, 2014.

Banaszynski et al., "Characterization of the FKBP.rapamycin.FRB ternary complex," *J. Am. Chem. Soc.,* 127:4715-4721, 2005.

Barstow et al., "A synthetic system links FeFe-hydrogenases to essential *E. coli* sulfur metabolism," *Journal of Biological Engineering,* 5:7, 2011.

Edgar, "MUSCLE: multiple sequence alignment with high accuracy and high throughput," *Nucleic Acids Research,* 32:1792-1797, 2004.

Eilenberg et al., "The dual effect of a ferredoxin-hydrogenase fusion protein in vivo: successful divergence of the photosynthetic electron flux towards hydrogen production and elevated oxygen tolerance," *Biotechnology for Biofuels,* 9:182, 2016.

Engler et al., "A One Pot, One Step, Precision Cloning Method with High Throughput Capability," *PLoS ONE,* 3:e3647, 2008.

Fish et al., "Structural basis for the thermostability of ferredoxin from the cyanobacterium *Mastigocladus laminosus*," *Journal of Molecular Biology*, 350:599-608, 2005.

Guntas et al., "Directed evolution of protein switches and their application to the creation of ligand-binding proteins," *Proceedings of the National Academy of Sciences of the United States of America*, 102:11224-11229, 2005.

Hirasawa et al., "Oxidation-reduction properties of maize ferredoxin: sulfite oxidoreductase," *Biochimica Et Biophysica Acta*, 1608:140-148, 2004.

Jensen et al., "Engineering of a synthetic electron conduit in living cells," *Proceedings of the National Academy of Sciences of the United States of America*, 107:19213-19218, 2010.

Kallio et al., "An engineered pathway for the biosynthesis of renewable propane" *Nature Communications*, 5:4731, 2014.

Kim et al., "Structural and mutational studies of an electron transfer complex of maize sulfite reductase and ferredoxin," *Journal of Biochemistry*, 160:101-109, 2016.

Kracke, et al., "Microbial electron transport and energy conservation—the foundation for optimizing bioelectrochemical systems," *Frontiers in Microbiology*, 6:575, 2015.

Kurisu et al., "Structure of the electron transfer complex between ferredoxin and ferredoxin-NADP(+) reductase," *Nature Structural Biology*, 8:117-121, 2001.

Kwon & Jewett, "High-throughput preparation methods of crude extract for robust cell-free protein synthesis," *Scientific Reports*, 5:srep08663, 2015.

Lin et al., "Cell-trappable fluorescent probes for endogenous hydrogen sulfide signaling and imaging H2O2-dependent H2S production," *Proceedings of the National Academy of Sciences of the United States of America*, 110:7131-7135, 2013.

Menke et al., "MATT: Local Flexibility Aids Protein Multiple Structure Alignment," *PLoS Computational Biology*, 4:e10, 2008.

Michnick, et al., "Solution structure of FKBP," *Science* (New York, N.Y.), 252:836-839, 1991.

Moscatiello et al., "Identification of ferredoxin II as a major calcium binding protein in the nitrogen-fixing symbiotic bacterium *Mesorhizobium loti*," *BMC Microbiology*, 15:16, 2015.

Paige et al., "Estrogen receptor (ER) modulators each induce distinct conformational changes in ER alpha and ER beta," *Proceedings of the National Academy of Sciences of the United States of America*, 96:3999-4004, 1999.

Pelletier et al., "Oligomerization domain-directed reassembly of active dihydrofolate reductase from rationally designed fragments," *Proceedings of the National Academy of Sciences of the United States of America*, 95:12141-12146, 1998.

Reinke et al., "A synthetic coiled-coil interactome provides heterospecific modules for molecular engineering," *Journal the American Chemical Society*, 132:6025-6031, 2010.

Rumpel et al., "Enhancing hydrogen production of microalgae by redirecting electrons from photosystem I to hydrogenase," *Energy Environ. Sci.*, 7:3296-3301, 2014.

Salis et al., "Automated design of synthetic ribosome binding sites to control protein expression," *Nature Biotechnology*, 27:946-950, 2009.

Schlesier et al., "A Conformational Switch Triggers Nitrogenase Protection from Oxygen Damage by Shethna Protein II (FeSII)," *Journal of the American Chemical Society* 138:239-247, 2016.

Segall-Shapiro et al., "Mesophilic and hyperthermophilic adenylate kinases differ in their tolerance to random fragmentation." *Journal of Molecular Biology*, 406:135-148, 2011.

Shiau et al., "The structural basis of estrogen receptor/coactivator recognition and the antagonism of this interaction by tamoxifen," *Cell*, 95:927-937, 1998.

Shomar et al., "Metabolic engineering of a carbapenem antibiotic synthesis pathway in *Escherichia coli*," *Nature Chemical Biology*, 14:794-800, 2018.

Sousa et al., "Early bioenergetic evolution," *Philosophical Transactions of the Royal Society of London. Series B, Biological Sciences*, 368:20130088, 2013.

Ta & Vickery, "Cloning, sequencing, and overexpression of a [2Fe-2S] ferredoxin gene from *Escherichia coli*," *The Journal of Biological Chemistry*, 267:11120-11125, 1992

Tanenbaum et al., "Crystallographic comparison of the estrogen and progesterone receptor's ligand binding domains," *Proceedings of the National Academy of Sciences of the United States of America*, 95:5998-6003, 1998.

Thomas et al., "Programming Post-Translational Control over the Metabolic Labeling of Cellular Proteins with a Noncanonical Amino Acid," *ACS Synthetic Biology*, 6:1572-1583, 2017.

Thompson et al., "SYNZIP protein interaction toolbox: in vitro and in vivo specifications of heterospecific coiled-coil interaction domains," *ACS Synth. Biol.*, 1:118-129, 2012.

Webster et al., "An arsenic-specific biosensor with genetically engineered *Shewanella oneidensis* in a bioelectrochemical system," *Biosensors & Bioelectronics*, 62:320-324, 2014.

Yang et al., "Modular electron-transport chains from eukaryotic organelles function to support nitrogenase activity," *Proceedings of the National Academy of Sciences of the United States of America*, 114:E2460-E2465, 2017.

What is claimed is:

1. An engineered cell comprising: a) a first nucleic acid segment encoding a first protein electron carrier (PEC) fragment, and b) a second nucleic acid segment encoding a second PEC fragment, wherein said first and second nucleic acid segments are under the transcriptional control of one or more promoters, wherein the PEC is a ferredoxin, a cytochrome, a flavodoxin, a rubredoxin, a cytochrome, a blue copper protein, or a Rieske protein, and wherein said first and second fragments, when co-expressed, are able to functionally associate to reconstitute the PEC and transport electrons, wherein said first and second nucleic acid segments are under the control of distinct promoters and/or wherein said one or more promoters are inducible.

2. The cell of claim 1, wherein said first nucleic acid segment encodes said first fragment fused to a first heterologous peptide or polypeptide, and said second nucleic acid segment encodes said second fragment fused to a second heterologous peptide or polypeptide, wherein said first and second heterologous peptides or polypeptides associate with each other and facilitate functional association of said first fragment and said second fragment.

3. The cell of claim 1, wherein said first and second nucleic acid segments are fused in a non-contiguous fashion to a third nucleic acid segment encoding a ligand-binding polypeptide that, when bound to said ligand, facilitates functional association of said first fragment and said second fragment.

4. The cell of claim 1, wherein said first nucleic acid segment encodes said first fragment fused to a first heterologous peptide or polypeptide, and said second nucleic acid segment encodes said second fragment fused to a second heterologous peptide or polypeptide, wherein said first and second peptides or polypeptides form a ternary complex in the presence of ternary complex forming agent, thereby facilitating functional association of said first fragment and said second fragment.

5. An expression vector comprising:
 a) a first nucleic acid segment encoding a first protein electron carrier (PEC) fragment, and
 b) a second nucleic acid segment encoding a second PEC fragment, wherein said first and second nucleic acid segments are under the transcriptional control of one or more promoters,
 wherein the PEC is a ferredoxin, a cytochrome, a flavodoxin, a rubredoxin, a cytochrome, a blue copper protein, or a Rieske protein,
 wherein said first and second fragments, when co-expressed, are able to functionally associate to reconstitute the PEC and transport electrons, wherein said first and second nucleic acid segments are under the control of distinct promoters and/or wherein said one or more promoters are inducible.

6. The vector of claim 5, wherein said first nucleic acid segment encodes said first fragment fused to a first heterologous peptide or polypeptide, and said second nucleic acid segment encodes said second fragment fused to a second heterologous peptide or polypeptide, wherein said first and second heterologous peptides or polypeptides associate with each other and facilitate functional association of said first fragment and said second fragment.

7. The vector of claim 5, wherein said first and second nucleic acid segments are fused in a non-contiguous fashion to a third nucleic acid segment encoding a ligand-binding polypeptide that, when bound to said ligand, facilitates functional association of said first fragment and said second fragment.

8. The vector of claim 5, wherein said first nucleic acid segment encodes said first fragment fused to a first heterologous peptide or polypeptide, and said second nucleic acid segment encodes said second fragment fused to a second heterologous peptide or polypeptide, wherein said first and second peptides or polypeptides form a ternary complex in the presence of ternary complex forming agent, thereby facilitating functional association of said first fragment and said second fragment.

9. A method of assessing activity of a protein electron carrier (PEC) comprising:
    a) providing a first PEC fragment and a second PEC fragment, wherein said first and second fragments, when associated, are capable of binding a cofactor necessary for electron transport by said PEC;
    b) subjecting said first and second PEC fragments to conditions permitting their association; and
    c) measuring electron transport by said PEC.

10. The method of claim 9, wherein conditions permitting association are:
    i) physical association of said first and second PEC fragments by fragment-fused first and second heterologous peptides or polypeptides that drive self-assembly of a functional PEC;
    ii) binding of a ligand that induces a conformational change in a polypeptide to which said first and second PEC fragments are fused; or
    iii) binding of a ternary complex binding agent to first and second heterologous peptides fused to said first and second PEC fragments that induces binding.

11. The engineered cell of claim 1, wherein the ferredoxin is a $Fe_2S_2$ ferredoxin, a $Fe_4S_4$ ferredoxin, or a high-potential (HiPIP) ferredoxin.

12. The engineered cell of claim 1, wherein the PEC is a ferredoxin, and wherein the ferredoxin is split after a residue corresponding to residue 9, 35, 65, or 72 of SEQ ID NO: 11 to generate the first fragment and the second fragment.

13. The vector of claim 5, wherein the ferredoxin is a $Fe_2S_2$ ferredoxin, a $Fe_4S_4$ ferredoxin, or a high-potential (HiPIP) ferredoxin.

14. The vector of claim 5, wherein the PEC is a ferredoxin, and wherein the ferredoxin is split after a residue corresponding to residue 9, 35, 65, or 72 of SEQ ID NO: 11 to generate the first fragment and the second fragment.

* * * * *

```
SEQUENCE LISTING

<160> NUMBER OF SEQ ID NOS: 60

<210> SEQ ID NO 1
<211> LENGTH: 97
<212> TYPE: PRT
<213> ORGANISM: Spinacia oleracea

<400> SEQUENCE: 1

Ala Ala Tyr Lys Val Thr Leu Val Thr Pro Thr Gly Asn Val Glu Phe
1               5                   10                  15
```

```
Gln Cys Pro Asp Asp Val Tyr Ile Leu Asp Ala Ala Glu Glu Gly
             20                  25                  30

Ile Asp Leu Pro Tyr Ser Cys Arg Ala Gly Ser Cys Ser Cys Ala
         35                  40                  45

Gly Lys Leu Lys Thr Gly Ser Leu Asn Gln Asp Gln Ser Phe Leu
 50                  55                  60

Asp Asp Asp Gln Ile Asp Glu Gly Trp Val Leu Thr Cys Ala Ala Tyr
 65                  70                  75                  80

Pro Val Ser Asp Val Thr Ile Glu Thr His Lys Lys Glu Glu Leu Thr
                 85                  90                  95

Ala

<210> SEQ ID NO 2
<211> LENGTH: 94
<212> TYPE: PRT
<213> ORGANISM: Chlorella fusca

<400> SEQUENCE: 2

Tyr Lys Val Thr Leu Lys Thr Pro Ser Gly Glu Glu Thr Ile Glu Cys
 1               5                  10                  15

Pro Glu Asp Thr Tyr Ile Leu Asp Ala Ala Glu Glu Ala Gly Leu Asp
             20                  25                  30

Leu Pro Tyr Ser Cys Arg Ala Gly Ala Cys Ser Ser Cys Ala Gly Lys
         35                  40                  45

Val Glu Ser Gly Glu Val Asp Gln Ser Asp Gln Ser Phe Leu Asp Asp
 50                  55                  60

Ala Gln Met Gly Lys Gly Phe Val Leu Thr Cys Val Ala Tyr Pro Thr
 65                  70                  75                  80

Ser Asp Val Thr Ile Leu Thr His Gln Glu Ala Ala Leu Tyr
                 85                  90

<210> SEQ ID NO 3
<211> LENGTH: 98
<212> TYPE: PRT
<213> ORGANISM: Anabaena PCC7119

<400> SEQUENCE: 3

Ala Thr Phe Lys Val Thr Leu Ile Asn Glu Ala Glu Gly Thr Lys His
 1               5                  10                  15

Glu Ile Glu Val Pro Asp Asp Glu Tyr Ile Leu Asp Ala Ala Glu Glu
             20                  25                  30

Gln Gly Tyr Asp Leu Pro Phe Ser Cys Arg Ala Gly Ala Cys Ser Thr
         35                  40                  45

Cys Ala Gly Lys Leu Val Ser Gly Thr Val Asp Gln Ser Asp Gln Ser
 50                  55                  60

Phe Leu Asp Asp Asp Gln Ile Glu Ala Gly Tyr Val Leu Thr Cys Val
 65                  70                  75                  80

Ala Tyr Pro Thr Ser Asp Val Val Ile Gln Thr His Lys Glu Glu Asp
                 85                  90                  95

Leu Tyr

<210> SEQ ID NO 4
<211> LENGTH: 128
<212> TYPE: PRT
<213> ORGANISM: Haloarcula marismortui

<400> SEQUENCE: 4
```

```
Pro Thr Val Glu Tyr Leu Asn Tyr Glu Val Asp Asp Asn Gly Trp
1               5                  10                 15

Asp Met Tyr Asp Asp Val Phe Gly Glu Ala Ser Asp Met Asp Leu
            20                 25                 30

Asp Asp Glu Asp Tyr Gly Ser Leu Glu Val Asn Glu Gly Tyr Ile
            35                 40                 45

Leu Glu Ala Ala Glu Ala Gln Gly Tyr Asp Trp Pro Phe Ser Cys Arg
50                  55                  60

Ala Gly Ala Cys Ala Asn Cys Ala Ala Ile Val Leu Glu Gly Asp Ile
65                  70                  75                  80

Asp Met Asp Met Gln Gln Ile Leu Ser Asp Glu Val Glu Asp Lys
            85                 90                 95

Asn Val Arg Leu Thr Cys Ile Gly Ser Pro Asp Ala Asp Glu Val Lys
            100                105                110

Ile Val Tyr Asn Ala Lys His Leu Asp Tyr Leu Gln Asn Arg Val Ile
        115                120                125
```

<210> SEQ ID NO 5
<211> LENGTH: 128
<212> TYPE: PRT
<213> ORGANISM: Halobacterium salinarum
<220> FEATURE:
<221> NAME/KEY: misc_feature
<222> LOCATION: (118)..(118)
<223> OTHER INFORMATION: Xaa can be any naturally occurring amino acid

<400> SEQUENCE: 5

```
Pro Thr Val Glu Tyr Leu Asn Tyr Glu Thr Leu Asp Asp Gln Gly Trp
1               5                  10                 15

Asp Met Asp Asp Asp Asp Leu Phe Glu Lys Ala Ala Asp Ala Gly Leu
            20                 25                 30

Asp Gly Glu Asp Tyr Gly Thr Met Glu Val Ala Glu Gly Tyr Ile
            35                 40                 45

Leu Glu Ala Ala Glu Ala Gln Gly Tyr Asp Trp Pro Phe Ser Cys Arg
50                  55                  60

Ala Gly Ala Cys Ala Asn Cys Ala Ser Ile Val Lys Glu Gly Glu Ile
65                  70                  75                  80

Asp Met Asp Met Gln Gln Ile Leu Ser Asp Glu Val Glu Glu Lys
            85                 90                 95

Asp Val Arg Leu Thr Cys Ile Gly Ser Pro Ala Ala Asp Glu Val Lys
            100                105                110

Ile Val Tyr Asn Ala Xaa His Leu Asp Tyr Leu Gln Asn Arg Val Ile
        115                120                125
```

<210> SEQ ID NO 6
<211> LENGTH: 98
<212> TYPE: PRT
<213> ORGANISM: Nostoc sp. PCC7120

<400> SEQUENCE: 6

```
Ala Ser Tyr Gln Val Arg Leu Ile Asn Lys Lys Gln Asp Ile Asp Thr
1               5                  10                 15

Thr Ile Glu Ile Asp Glu Glu Thr Thr Ile Leu Asp Gly Ala Glu Glu
            20                 25                 30

Asn Gly Ile Glu Leu Pro Phe Ser Cys His Ser Gly Ser Cys Ser Ser
            35                 40                 45

Cys Val Gly Lys Val Val Glu Gly Glu Val Asp Gln Ser Asp Gln Ile
```

```
                    50                  55                  60
Phe Leu Asp Asp Glu Gln Met Gly Lys Gly Phe Ala Leu Leu Cys Val
 65                  70                  75                  80

Thr Tyr Pro Arg Ser Asn Cys Thr Ile Lys Thr His Gln Glu Pro Tyr
                 85                  90                  95

Leu Ala

<210> SEQ ID NO 7
<211> LENGTH: 95
<212> TYPE: PRT
<213> ORGANISM: Equisetum arvense

<400> SEQUENCE: 7

Ala Tyr Lys Thr Val Leu Lys Thr Pro Ser Gly Glu Phe Thr Leu Asp
  1               5                  10                  15

Val Pro Glu Gly Thr Thr Ile Leu Asp Ala Ala Glu Glu Ala Gly Tyr
                 20                  25                  30

Asp Leu Pro Phe Ser Cys Arg Ala Gly Ala Cys Ser Ser Cys Leu Gly
             35                  40                  45

Lys Val Val Ser Gly Ser Val Asp Glu Ser Gly Ser Phe Leu Asp Asp
         50                  55                  60

Asp Gly Gln Met Glu Glu Gly Phe Val Leu Thr Cys Ile Ala Ile Pro
 65                  70                  75                  80

Glu Ser Asp Leu Val Ile Glu Thr His Lys Glu Glu Leu Phe
                 85                  90                  95

<210> SEQ ID NO 8
<211> LENGTH: 98
<212> TYPE: PRT
<213> ORGANISM: Plasmodium falciparum

<400> SEQUENCE: 8

Ala Phe Tyr Asn Ile Thr Leu Arg Thr Asn Asp Gly Glu Lys Lys Ile
  1               5                  10                  15

Glu Cys Asn Glu Asp Glu Tyr Ile Leu Asp Ala Ser Glu Arg Gln Asn
                 20                  25                  30

Val Glu Leu Pro Tyr Ser Cys Arg Gly Gly Ser Cys Ser Thr Cys Ala
             35                  40                  45

Ala Lys Leu Val Glu Gly Glu Val Asp Asn Asp Gln Ser Tyr Leu
         50                  55                  60

Asp Glu Glu Gln Ile Lys Lys Tyr Ile Leu Leu Cys Thr Cys Tyr
 65                  70                  75                  80

Pro Lys Ser Asp Cys Val Ile Glu Thr His Lys Glu Asp Glu Leu His
                 85                  90                  95

Asp Met

<210> SEQ ID NO 9
<211> LENGTH: 97
<212> TYPE: PRT
<213> ORGANISM: Synechocystis PCC6803

<400> SEQUENCE: 9

Met Ala Ser Tyr Thr Val Lys Leu Ile Thr Pro Asp Gly Glu Ser Ser
  1               5                  10                  15

Ile Glu Cys Ser Asp Asp Thr Tyr Ile Leu Asp Ala Ala Glu Glu Ala
                 20                  25                  30

Gly Leu Asp Leu Pro Tyr Ser Cys Arg Ala Gly Ala Cys Ser Thr Cys
```

```
            35                  40                  45
Ala Gly Lys Ile Thr Ala Gly Ser Val Asp Gln Ser Asp Gln Ser Phe
 50                  55                  60

Leu Asp Asp Asp Gln Ile Glu Ala Gly Tyr Val Leu Thr Cys Val Ala
 65                  70                  75                  80

Tyr Pro Thr Ser Asp Cys Thr Ile Glu Thr His Lys Glu Glu Asp Leu
                 85                  90                  95

Tyr

<210> SEQ ID NO 10
<211> LENGTH: 96
<212> TYPE: PRT
<213> ORGANISM: Petroselinum crispum

<400> SEQUENCE: 10

Ala Thr Tyr Asn Val Lys Leu Ile Thr Pro Asp Gly Glu Val Glu Phe
 1               5                  10                  15

Lys Cys Asp Asp Asp Val Tyr Val Leu Asp Gln Ala Glu Glu Glu Gly
                 20                  25                  30

Ile Asp Ile Pro Tyr Ser Cys Arg Ala Gly Ser Cys Ser Ser Cys Ala
             35                  40                  45

Gly Lys Val Val Ser Gly Ser Ile Asp Gln Ser Asp Gln Ser Phe Leu
 50                  55                  60

Asp Asp Glu Gln Met Asp Ala Gly Tyr Val Leu Thr Cys His Ala Tyr
 65                  70                  75                  80

Pro Thr Ser Asp Val Val Ile Glu Thr His Lys Glu Glu Glu Ile Val
                 85                  90                  95

<210> SEQ ID NO 11
<211> LENGTH: 98
<212> TYPE: PRT
<213> ORGANISM: Mastigocladus laminosus

<400> SEQUENCE: 11

Ala Thr Tyr Lys Val Thr Leu Ile Asn Glu Ala Glu Gly Leu Asn Lys
 1               5                  10                  15

Thr Ile Glu Val Pro Asp Asp Gln Tyr Ile Leu Asp Ala Ala Glu Glu
                 20                  25                  30

Ala Gly Ile Asp Leu Pro Tyr Ser Cys Arg Ala Gly Ala Cys Ser Thr
             35                  40                  45

Cys Ala Gly Lys Leu Ile Ser Gly Thr Val Asp Gln Ser Asp Gln Ser
 50                  55                  60

Phe Leu Asp Asp Asp Gln Ile Glu Ala Gly Tyr Val Leu Thr Cys Val
 65                  70                  75                  80

Ala Tyr Pro Thr Ser Asp Cys Val Ile Glu Thr His Lys Glu Glu Glu
                 85                  90                  95

Leu Tyr

<210> SEQ ID NO 12
<211> LENGTH: 97
<212> TYPE: PRT
<213> ORGANISM: Thermosynechococcus elongatus

<400> SEQUENCE: 12

Ala Thr Tyr Lys Val Thr Leu Val Arg Pro Asp Gly Ser Glu Thr Thr
 1               5                  10                  15

Ile Asp Val Pro Glu Asp Glu Tyr Ile Leu Asp Val Ala Glu Glu Gln
```

```
                    20                  25                  30

Gly Leu Asp Leu Pro Phe Ser Cys Arg Ala Gly Ala Cys Ser Thr Cys
            35                  40                  45

Ala Gly Lys Leu Leu Glu Gly Glu Val Asp Gln Ser Asp Gln Ser Phe
        50                  55                  60

Leu Asp Asp Asp Gln Ile Glu Lys Gly Phe Val Leu Thr Cys Val Ala
65                  70                  75                  80

Tyr Pro Arg Ser Asp Cys Lys Ile Leu Thr Asn Gln Glu Glu Glu Leu
                85                  90                  95

Tyr

<210> SEQ ID NO 13
<211> LENGTH: 93
<212> TYPE: PRT
<213> ORGANISM: Equisetum arvense

<400> SEQUENCE: 13

Ala Tyr Lys Val Thr Leu Lys Thr Pro Asp Gly Asp Ile Thr Phe Asp
1               5                   10                  15

Val Glu Pro Gly Glu Arg Leu Ile Asp Ile Gly Ser Glu Lys Ala Asp
                20                  25                  30

Leu Pro Leu Ser Cys Gln Ala Gly Ala Cys Ser Thr Cys Leu Gly Lys
            35                  40                  45

Ile Val Ser Gly Thr Val Asp Gln Ser Glu Gly Ser Phe Leu Asp Asp
        50                  55                  60

Glu Gln Ile Glu Gln Gly Tyr Val Leu Thr Cys Ile Ala Ile Pro Glu
65                  70                  75                  80

Ser Asp Val Val Ile Glu Thr His Lys Glu Asp Glu Leu
                85                  90

<210> SEQ ID NO 14
<211> LENGTH: 101
<212> TYPE: PRT
<213> ORGANISM: Chlamydomonas reinhardtii

<400> SEQUENCE: 14

Met Tyr Lys Val Thr Leu Lys Thr Pro Ser Gly Asp Lys Thr Ile Glu
1               5                   10                  15

Cys Pro Ala Asp Thr Tyr Ile Leu Asp Ala Ala Glu Glu Ala Gly Leu
                20                  25                  30

Asp Leu Pro Tyr Ser Cys Arg Ala Gly Ala Cys Ser Ser Cys Ala Gly
            35                  40                  45

Lys Val Ala Ala Gly Thr Val Asp Gln Ser Asp Gln Ser Phe Leu Asp
        50                  55                  60

Asp Ala Gln Met Gly Asn Gly Phe Val Leu Thr Cys Val Ala Tyr Pro
65                  70                  75                  80

Thr Ser Asp Cys Thr Ile Gln Thr His Gln Glu Glu Ala Leu Tyr Glu
                85                  90                  95

Asn Leu Tyr Phe Gln
            100

<210> SEQ ID NO 15
<211> LENGTH: 97
<212> TYPE: PRT
<213> ORGANISM: Cyanidioschyzon merolae

<400> SEQUENCE: 15
```

```
Met Tyr Lys Ile Gln Leu Val Asn Gln Lys Glu Gly Ile Asp Val Thr
1               5                   10                  15

Ile Gln Cys Ala Gly Asp Gln Tyr Ile Leu Asp Ala Ala Glu Glu Gln
            20                  25                  30

Gly Val Asp Leu Pro Tyr Ser Cys Arg Ala Gly Ala Cys Ser Thr Cys
        35                  40                  45

Ala Gly Lys Leu Val Lys Gly Ser Val Asp Gln Ser Asp Gln Ser Phe
    50                  55                  60

Leu Asp Glu Asp Gln Ile Ser Lys Gly Phe Ile Leu Thr Cys Val Ala
65                  70                  75                  80

Tyr Pro Thr Ser Asp Cys Val Ile Gln Thr His Gln Glu Glu Ala Leu
                85                  90                  95

Tyr
```

```
<210> SEQ ID NO 16
<211> LENGTH: 97
<212> TYPE: PRT
<213> ORGANISM: Aphanothece sacrum

<400> SEQUENCE: 16
```

```
Ala Ser Tyr Lys Val Thr Leu Lys Thr Pro Asp Gly Asp Asn Val Ile
1               5                   10                  15

Thr Val Pro Asp Asp Glu Tyr Ile Leu Asp Val Ala Glu Glu Gln Gly
            20                  25                  30

Leu Asp Leu Pro Tyr Ser Cys Arg Ala Gly Ala Cys Ser Thr Cys Ala
        35                  40                  45

Gly Lys Leu Val Ser Gly Pro Ala Pro Asp Gln Ser Asp Gln Ser Phe
    50                  55                  60

Leu Asp Asp Asp Gln Ile Gln Ala Gly Tyr Ile Leu Thr Cys Val Ala
65                  70                  75                  80

Tyr Pro Thr Gly Asp Cys Val Ile Glu Thr His Lys Glu Glu Ala Leu
                85                  90                  95

Tyr
```

```
<210> SEQ ID NO 17
<211> LENGTH: 98
<212> TYPE: PRT
<213> ORGANISM: Zea mays

<400> SEQUENCE: 17
```

```
Ala Thr Tyr Asn Val Lys Leu Ile Thr Pro Glu Gly Glu Val Glu Leu
1               5                   10                  15

Gln Val Pro Asp Asp Val Tyr Ile Leu Asp Gln Ala Glu Glu Asp Gly
            20                  25                  30

Ile Asp Leu Pro Tyr Ser Cys Arg Ala Gly Ser Cys Ser Ser Cys Ala
        35                  40                  45

Gly Lys Val Val Ser Gly Ser Val Asp Gln Ser Asp Gln Ser Tyr Leu
    50                  55                  60

Asp Asp Gly Gln Ile Ala Asp Gly Trp Val Leu Thr Cys His Ala Tyr
65                  70                  75                  80

Pro Thr Ser Asp Val Val Ile Glu Thr His Lys Glu Glu Glu Leu Thr
                85                  90                  95

Gly Ala
```

```
<210> SEQ ID NO 18
<211> LENGTH: 98
```

```
<212> TYPE: PRT
<213> ORGANISM: Leptolyngbya boryanum

<400> SEQUENCE: 18

Pro Ser Phe Lys Val Thr Leu Ile Asn Glu Thr Glu Gly Leu Asn Thr
1               5                   10                  15

Thr Ile Glu Val Pro Asp Asp Glu Tyr Ile Leu Asp Ala Ala Glu Glu
                20                  25                  30

Gln Gly Ile Asp Leu Pro Tyr Ser Cys Arg Ala Gly Ala Cys Ser Thr
            35                  40                  45

Cys Ala Gly Lys Ile Thr Ala Gly Thr Val Asp Gln Ser Asp Gln Ser
    50                  55                  60

Phe Leu Asp Asp Asp Gln Ile Gln Ala Gly Tyr Val Leu Thr Cys Val
65                  70                  75                  80

Ala Tyr Pro Thr Ser Asp Cys Thr Ile Leu Thr His Gln Glu Glu Asp
                85                  90                  95

Leu Tyr

<210> SEQ ID NO 19
<211> LENGTH: 98
<212> TYPE: PRT
<213> ORGANISM: Spirulina platensis

<400> SEQUENCE: 19

Ala Thr Tyr Lys Val Thr Leu Ile Asn Glu Ala Glu Gly Ile Asn Glu
1               5                   10                  15

Thr Ile Asp Cys Asp Asp Asp Thr Tyr Ile Leu Asp Ala Ala Glu Glu
                20                  25                  30

Ala Gly Leu Asp Leu Pro Tyr Ser Cys Arg Ala Gly Ala Cys Ser Thr
            35                  40                  45

Cys Ala Gly Thr Ile Thr Ser Gly Thr Ile Asp Gln Ser Asp Gln Ser
    50                  55                  60

Phe Leu Asp Asp Asp Gln Ile Glu Ala Gly Tyr Val Leu Thr Cys Val
65                  70                  75                  80

Ala Tyr Pro Thr Ser Asp Cys Thr Ile Lys Thr His Gln Glu Glu Gly
                85                  90                  95

Leu Tyr

<210> SEQ ID NO 20
<211> LENGTH: 105
<212> TYPE: PRT
<213> ORGANISM: Chlamydomonas reinhardtii

<400> SEQUENCE: 20

Met Phe Lys Val Thr Phe Lys Thr Pro Lys Gly Glu Lys Thr Ile Asp
1               5                   10                  15

Val Glu Ala Asp Lys Tyr Leu Leu Asp Ala Ala Glu Glu Ala Gly Met
                20                  25                  30

Asp Leu Pro Tyr Ser Cys Arg Ser Gly Gly Cys Ser Thr Cys Cys Gly
            35                  40                  45

Lys Leu Glu Ser Gly Thr Val Asp Gln Ser Asp Gln Asn Met Leu Asp
    50                  55                  60

Glu Asp Gln Leu Lys Gln Gly Phe Val Leu Thr Cys Val Ala Tyr Pro
65                  70                  75                  80

Thr Ser Asp Ile Val Ile Leu Thr Asp Gln Glu Ser Lys Leu Pro Ile
                85                  90                  95
```

```
Gly Gly Ser Glu Asn Leu Tyr Phe Gln
            100                 105

<210> SEQ ID NO 21
<211> LENGTH: 105
<212> TYPE: PRT
<213> ORGANISM: Arabidopsis thaliana

<400> SEQUENCE: 21

Met Ala Thr Tyr Lys Val Lys Phe Ile Thr Pro Glu Gly Glu Leu Glu
1               5                   10                  15

Val Glu Cys Asp Asp Val Tyr Val Leu Asp Ala Ala Glu Glu Ala
            20                  25                  30

Gly Ile Asp Leu Pro Tyr Ser Cys Arg Ala Gly Ser Cys Ser Ser Cys
        35                  40                  45

Ala Gly Lys Val Val Ser Gly Ser Val Asp Gln Ser Asp Gln Ser Phe
    50                  55                  60

Leu Asp Asp Glu Gln Ile Gly Glu Gly Phe Val Leu Thr Cys Ala Ala
65                  70                  75                  80

Tyr Pro Thr Ser Asp Val Thr Ile Glu Thr His Lys Glu Glu Ala Ile
                85                  90                  95

Met Leu Glu His His His His His His
            100                 105

<210> SEQ ID NO 22
<211> LENGTH: 118
<212> TYPE: PRT
<213> ORGANISM: Prochlorococcus marinus

<400> SEQUENCE: 22

Ile Ile Arg Phe Ile Arg Glu Gly Ile Asp Ile Glu Cys Lys Pro Gly
1               5                   10                  15

Glu Asn Leu Arg Glu Leu Val Ile Arg Glu Lys Leu Gln Leu Tyr Gly
            20                  25                  30

Leu Lys Gly Ile Leu Gly Asn Cys Gly Gly Val Gly Gln Cys Ser Thr
        35                  40                  45

Cys Phe Val Ser Val Glu Gly Gly Ala Lys Asn Ser Leu Ser Pro Leu
    50                  55                  60

Thr Ser Val Glu Glu Lys Leu Asn Asn Arg Pro Asp Asn Trp Arg
65                  70                  75                  80

Leu Ala Cys Gln Thr Leu Ile Asn Ser Ser Ala Val Ile Leu Thr Lys
                85                  90                  95

Pro Gln Ser Pro Pro Ser Asn Leu Lys Asp Leu Lys Glu Ser Ala Glu
            100                 105                 110

Ser Lys Lys Leu Pro Arg
        115

<210> SEQ ID NO 23
<211> LENGTH: 111
<212> TYPE: PRT
<213> ORGANISM: Pseudomonas putida

<400> SEQUENCE: 23

Pro Thr Val Phe Glu Ile Thr Val Arg Pro Asp Gly Glu Ser Phe Val
1               5                   10                  15

Cys Gln Pro Gln Gln Ser Val Leu Arg Ala Met Glu Ala Gln Asn Lys
            20                  25                  30

His Cys Leu Pro Val Gly Cys Arg Gly Gly Gly Cys Gly Leu Cys Lys
```

```
             35                  40                  45
Val Arg Val Leu Thr Gly Asp Tyr Glu Cys Gly Arg Met Ser Cys Lys
 50                  55                  60

His Val Pro Val Glu Ala Arg Glu Gln Gly Tyr Ala Leu Ala Cys Arg
 65                  70                  75                  80

Leu Phe Ala Arg Ser Asp Leu Cys Ile Glu Arg Tyr Ser Lys Pro Cys
                 85                  90                  95

Tyr Glu Asn Thr Val Asp Pro Gln Gln Arg Gly Lys Val Thr Ser
                100                 105                 110

<210> SEQ ID NO 24
<211> LENGTH: 111
<212> TYPE: PRT
<213> ORGANISM: Pseudomonas putida

<400> SEQUENCE: 24

Asn Ser Ala Gly Tyr Glu Val Phe Glu Val Leu Ser Gly Gln Ser Phe
 1               5                  10                  15

Arg Cys Ala Glu Gly Gln Ser Val Leu Arg Ala Met Glu Ala Gln Gly
                20                  25                  30

Lys Arg Cys Ile Pro Val Gly Cys Arg Gly Gly Cys Gly Leu Cys
                35                  40                  45

Arg Val Arg Val Leu Ser Gly Ala Tyr Arg Ser Gly Arg Met Ser Arg
 50                  55                  60

Gly His Val Pro Ala Lys Ala Ala Glu Ala Leu Ala Leu Ala Cys
 65                  70                  75                  80

Gln Val Phe Pro Gln Thr Asp Leu Thr Ile Glu Tyr Phe Arg His Val
                 85                  90                  95

Gly Gly Asn Lys Pro Asp Asn Met Asn Tyr Glu Glu Val Thr Ser
                100                 105                 110

<210> SEQ ID NO 25
<211> LENGTH: 100
<212> TYPE: PRT
<213> ORGANISM: Pseudomonas putida

<400> SEQUENCE: 25

Ser Ser Pro Pro Phe Gln Val His Glu Thr Asn Ser Gly Gln Ser Phe
 1               5                  10                  15

Thr Cys Arg Pro Asp Gln Ser Val Leu Arg Ala Met Glu Glu Gln Gly
                20                  25                  30

Lys Arg Cys Val Pro Val Gly Cys Arg Gly Gly Cys Gly Leu Cys
                35                  40                  45

Lys Val Arg Val Leu Ser Gly Asp Tyr Gln Cys Gly Arg Met Ser Cys
 50                  55                  60

Ser Gln Val Pro Pro Glu Ala Gly Glu Gln Gly Leu Ala Leu Ala Cys
 65                  70                  75                  80

Gln Leu Tyr Pro Arg Ala Asp Leu Tyr Ile Glu Ser Leu Arg Gln Val
                 85                  90                  95

Arg Ser Asn Pro
                100

<210> SEQ ID NO 26
<211> LENGTH: 111
<212> TYPE: PRT
<213> ORGANISM: Pseudomonas putida

<400> SEQUENCE: 26
```

Asn Arg Ala Gly Tyr Glu Ile Arg Glu Thr Val Ser Gly Gln Thr Phe
1               5                   10                  15

Arg Cys Leu Pro Asp Gln Ser Val Leu Ser Ala Met Glu Gln Gln Gly
            20                  25                  30

Lys Arg Cys Val Pro Val Gly Cys Arg Gly Gly Cys Gly Leu Cys
        35                  40                  45

Lys Val Arg Val Leu Ser Gly Thr Tyr Gln Cys His Lys Met Ser Cys
    50                  55                  60

Asn His Val Pro Pro Glu Ala Ala Lys Gln Gly Leu Ala Leu Ala Cys
65                  70                  75                  80

Gln Leu Phe Pro Gln Thr Asp Leu Asn Ile Glu Cys Leu Arg Arg Gln
            85                  90                  95

Gly Pro Gly Asp His Asn Asn Lys Asn Gln Gln Glu Val Ser Ser
            100                 105                 110

<210> SEQ ID NO 27
<211> LENGTH: 98
<212> TYPE: PRT
<213> ORGANISM: Methylococcus capsulatus

<400> SEQUENCE: 27

Met Gln Arg Val His Thr Ile Thr Ala Val Thr Glu Asp Gly Glu Ser
1               5                   10                  15

Leu Arg Phe Glu Cys Arg Ser Asp Glu Asp Val Ile Thr Ala Ala Leu
            20                  25                  30

Arg Gln Asn Ile Phe Leu Met Ser Ser Cys Arg Glu Gly Gly Cys Ala
        35                  40                  45

Thr Cys Lys Ala Leu Cys Ser Glu Gly Asp Tyr Asp Leu Lys Gly Cys
    50                  55                  60

Ser Val Gln Ala Leu Pro Pro Glu Glu Glu Glu Gly Leu Val Leu
65                  70                  75                  80

Leu Cys Arg Thr Tyr Pro Lys Thr Asp Leu Glu Ile Glu Leu Pro Tyr
            85                  90                  95

Thr His

<210> SEQ ID NO 28
<211> LENGTH: 129
<212> TYPE: PRT
<213> ORGANISM: Chlamydomonas reinhardtii

<400> SEQUENCE: 28

Tyr Lys Val Thr Phe Val Gly Ala Asp Gly Glu Thr Arg Glu Ile Ser
1               5                   10                  15

Cys Pro Asp Asn Gln Tyr Ile Leu Asp Ala Ala Glu Ala Gln Gly Leu
            20                  25                  30

Asp Leu Pro Ala Thr Cys Arg Gly Gly Ile Cys Gly Ala Cys Val Ala
        35                  40                  45

Arg Val Ala Lys Gly Thr Ile Asp Pro Ser Asp Ile Ala Asp Leu Thr
    50                  55                  60

Phe Thr Leu Asp Glu Glu Glu Gln Ala Lys Gly Met Ala Leu Leu Cys
65                  70                  75                  80

Met Thr Arg Ala Thr Ser Asp Leu Thr Leu Glu Thr Gln Ser Asp Trp
            85                  90                  95

Gly Tyr Ser Leu Gly Val Gly Glu Trp Lys Gly Ala Thr Gly Lys Phe
            100                 105                 110

Ser Ser Arg Pro Glu Pro Thr Met Gly Lys Gly Trp Ala Glu Leu Gln
         115                 120                 125

Lys

<210> SEQ ID NO 29
<211> LENGTH: 103
<212> TYPE: PRT
<213> ORGANISM: Chlamydomonas reinhardtii

<400> SEQUENCE: 29

Phe Gln Val Thr Leu Arg Met Pro Ser Gly Lys Thr Lys Thr Met Glu
1               5                   10                  15

Val Gly Pro Asp Glu Ala Leu Phe Asp Ala Val Glu Arg Tyr Asp Val
            20                  25                  30

Asp Leu Pro Tyr Leu Cys Arg Thr Gly Thr Cys Gly Thr Cys Ala Gly
        35                  40                  45

Arg Val Gln Glu Gly Gln Val Glu Leu Lys Gly Gln His Ile Leu Asp
    50                  55                  60

Pro Asp Gln Val Lys Ala Gly Phe Ile Leu Met Cys Ser Ala Tyr Pro
65                  70                  75                  80

Arg Ser Asp Cys Thr Ile Leu Thr His Gln Glu Glu Arg Leu His Thr
                85                  90                  95

Cys Glu Tyr Gly Lys His Gln
            100

<210> SEQ ID NO 30
<211> LENGTH: 101
<212> TYPE: PRT
<213> ORGANISM: Chlamydomonas reinhardtii

<400> SEQUENCE: 30

Tyr Lys Ile Ser Leu Thr His Glu Gly Lys Gln Val Asp Leu Ala Val
1               5                   10                  15

Pro Glu Gly Glu Ser Ile Leu Ser Val Ala Leu Asp Lys Gly Leu Asp
            20                  25                  30

Leu Pro His Asp Cys Lys Leu Gly Val Cys Met Thr Cys Pro Ala Lys
        35                  40                  45

Leu Val Ser Gly Thr Val Asp Ala Ser Gly Ser Met Leu Ser Asp Asp
    50                  55                  60

Val Ala Glu Lys Gly Tyr Thr Leu Leu Cys Val Ala Val Pro Lys Ser
65                  70                  75                  80

Asp Cys Gln Val Lys Thr Ile Ser Glu Asp Glu Leu Leu Asp Met Gln
                85                  90                  95

Leu Met Thr Ser Gln
            100

<210> SEQ ID NO 31
<211> LENGTH: 102
<212> TYPE: PRT
<213> ORGANISM: Synechocystis PCC6803

<400> SEQUENCE: 31

Gly Ala Ile Tyr Ser Val Asn Leu Val Asn Pro Ala Thr Gly Ser Asp
1               5                   10                  15

Val Thr Ile Glu Val Ala Glu Asp Glu Leu Ile Leu Glu Ala Ala Glu
            20                  25                  30

Asn Gln Gly Leu Asp Leu Pro Tyr Ser Cys Arg Ala Ala Ser Cys Val
        35                  40                  45

Ala Cys Ala Gly Arg Leu Leu Glu Gly Thr Val Glu His Thr Asp Lys
    50                  55                  60

Gly Ser Asp Phe Leu Lys Pro Glu Glu Leu Ala Ala Gly Cys Val Leu
 65                  70                  75                  80

Leu Cys Ala Ala Tyr Ala Thr Ser Asp Cys Lys Ile Leu Thr His Gln
                 85                  90                  95

Glu Glu Ala Leu Phe Gly
            100

<210> SEQ ID NO 32
<211> LENGTH: 99
<212> TYPE: PRT
<213> ORGANISM: Arabidopsis thaliana

<400> SEQUENCE: 32

Ala Lys Glu Ser Arg Lys Val Lys Leu Ile Ser Pro Glu Gly Glu Glu
 1               5                  10                  15

Gln Glu Ile Glu Gly Asn Glu Asp Cys Cys Ile Leu Glu Ser Ala Glu
             20                  25                  30

Asn Ala Gly Leu Glu Leu Pro Tyr Ser Cys Arg Ser Gly Thr Cys Gly
         35                  40                  45

Thr Cys Cys Gly Lys Leu Val Ser Gly Lys Val Asp Gln Ser Leu Gly
 50                  55                  60

Ser Phe Leu Glu Glu Glu Gln Ile Gln Lys Gly Tyr Ile Leu Thr Cys
 65                  70                  75                  80

Ile Ala Leu Pro Leu Glu Asp Cys Val Val Tyr Thr His Lys Gln Ser
                 85                  90                  95

Asp Leu Ile

<210> SEQ ID NO 33
<211> LENGTH: 103
<212> TYPE: PRT
<213> ORGANISM: Toxoplasma gondii

<400> SEQUENCE: 33

Leu Phe His Arg Ile Lys Leu Gln Thr Pro Asp Gly Glu Thr Lys Glu
 1               5                  10                  15

Leu Glu Cys Ala Glu Asp Glu Tyr Ile Leu Asp Ala Ala Glu Ala Ala
             20                  25                  30

Gly Ile Glu Leu Pro Tyr Ser Cys Arg Gly Gly Ser Cys Ser Thr Cys
         35                  40                  45

Ala Gly Lys Leu Leu Val Gly Ser Val Asp Gly Ser Glu Gln Val Tyr
 50                  55                  60

Leu Asp Asp Ala Gln Gln Lys Lys Gly Tyr Val Leu Leu Cys Thr Ala
 65                  70                  75                  80

Tyr Pro Lys Glu Asp Cys Thr Ile Leu Thr His Gln Glu Asp Gln Leu
                 85                  90                  95

His Ser Glu Gly Gly Asp Glu
            100

<210> SEQ ID NO 34
<211> LENGTH: 98
<212> TYPE: PRT
<213> ORGANISM: Anabaena variabilis

<400> SEQUENCE: 34

Ala Thr Tyr Gln Val Arg Leu Ile Ser Lys Lys Glu Asn Ile Asp Thr

```
                1               5                  10                  15
                Thr Ile Glu Ile Asp Glu Glu Thr Thr Ile Leu Asp Gly Ala Glu Glu
                                 20                  25                  30

Asn Gly Ile Glu Leu Pro Phe Ser Cys His Ser Gly Ser Cys Ser Ser
                            35                  40                  45

Cys Val Gly Lys Val Val Gly Glu Val Asp Gln Ser Asp Gln Ile
                 50                  55                  60

Phe Leu Asp Asp Glu Gln Val Gly Lys Gly Phe Ala Leu Leu Cys Val
                65                  70                  75                  80

Thr Tyr Pro Arg Ser Asn Cys Thr Ile Lys Thr His Gln Glu Pro Tyr
                                 85                  90                  95

Leu Ala
```

<210> SEQ ID NO 35
<211> LENGTH: 98
<212> TYPE: PRT
<213> ORGANISM: Anabaena variabilis

<400> SEQUENCE: 35

```
                Thr Thr Tyr Gln Val Arg Leu Ile Asn Lys Lys Arg Ala Ile Asp Ile
                1               5                  10                  15

Thr Ile Pro Val Asp Glu Asn Thr Thr Ile Leu Asp Ala Ala Glu Gln
                                 20                  25                  30

Gln Asp Ile Glu Leu Pro Phe Ser Cys Gln Ser Gly Ser Cys Ser Ser
                            35                  40                  45

Cys Val Ala Lys Val Val Glu Gly Glu Val Asp Gln Ser Glu Gln Val
                 50                  55                  60

Phe Leu Asp Glu Glu Gln Met Ala Lys Gly Phe Ile Val Leu Cys Val
                65                  70                  75                  80

Ser Tyr Pro Arg Ser Asp Cys Thr Ile Arg Thr His Gln Glu Pro Tyr
                                 85                  90                  95

Leu Val
```

<210> SEQ ID NO 36
<211> LENGTH: 96
<212> TYPE: PRT
<213> ORGANISM: Prochlorococcus phage P-SSM2

<400> SEQUENCE: 36

```
                Ala Tyr Ser Ile Thr Leu Arg Ser Pro Asp Gly Ala Glu Glu Val Val
                1               5                  10                  15

Gln Cys Glu Glu Asp Gln Tyr Ile Leu Glu Ala Ala Glu Asp Ala Gly
                                 20                  25                  30

Leu Asp Met Pro Ser Ser Cys Arg Ala Gly Ala Cys Ser Ala Cys Leu
                            35                  40                  45

Gly Lys Val Leu Glu Gly Ser Val Asn Asn Glu Glu Gln Ser Phe Leu
                 50                  55                  60

Asp Asp Asp Gln Leu Glu Gly Gly Trp Ser Leu Leu Cys Val Ala Met
                65                  70                  75                  80

Pro Gln Ser Asp Cys Val Ile Leu Thr Glu Gln Glu Asp Asn Leu Asp
                                 85                  90                  95
```

<210> SEQ ID NO 37
<211> LENGTH: 95
<212> TYPE: PRT
<213> ORGANISM: Prochlorococcus phage Syn33

```
<400> SEQUENCE: 37

Thr Tyr Asn Val Thr Leu Gln Ser Pro Asp Gly Thr Glu Ala Val Ile
1               5                   10                  15

Gln Cys Glu Ala Asp Gln Tyr Ile Leu Glu Ala Ala Glu Ala Gly
            20                  25                  30

Val Asp Leu Pro Ser Ser Cys Lys Ala Gly Ala Cys Ser Ala Cys Ala
            35                  40                  45

Gly Lys Leu Val Ser Gly Thr Val Asp Asn Glu Glu Gln Ser Phe Leu
50                  55                  60

Asp Asp Asp Gln Leu Glu Asp Gly Trp Val Leu Thr Cys Val Ala Tyr
65                  70                  75                  80

Pro Thr Ser Asp Cys Val Ile Leu Thr Glu Gln Glu Glu Asn Leu
                85                  90                  95

<210> SEQ ID NO 38
<211> LENGTH: 98
<212> TYPE: PRT
<213> ORGANISM: Porphyra umbilicalis

<400> SEQUENCE: 38

Ala Asp Tyr Lys Ile His Leu Val Ser Lys Glu Glu Gly Ile Asp Val
1               5                   10                  15

Thr Phe Asp Cys Ser Glu Asp Thr Tyr Ile Leu Asp Ala Ala Glu Glu
            20                  25                  30

Glu Gly Ile Glu Leu Pro Tyr Ser Cys Arg Ala Gly Ala Cys Ser Thr
            35                  40                  45

Cys Ala Gly Lys Val Thr Glu Gly Thr Val Asp Gln Ser Asp Gln Ser
50                  55                  60

Phe Leu Asp Asp Glu Gln Met Leu Lys Gly Tyr Val Leu Thr Cys Ile
65                  70                  75                  80

Ala Tyr Pro Glu Ser Asp Cys Thr Ile Leu Thr His Val Glu Gln Glu
                85                  90                  95

Leu Tyr

<210> SEQ ID NO 39
<211> LENGTH: 106
<212> TYPE: PRT
<213> ORGANISM: Arabidopsis thaliana

<400> SEQUENCE: 39

Ala Asn Ser Gly Gly Ala Thr Met Ser Ala Val Tyr Lys Val Lys Leu
1               5                   10                  15

Leu Gly Pro Asp Gly Gln Glu Asp Glu Phe Glu Val Gln Asp Asp Gln
            20                  25                  30

Tyr Ile Leu Asp Ala Ala Glu Ala Gly Val Asp Leu Pro Tyr Ser
            35                  40                  45

Cys Arg Ala Gly Ala Cys Ser Thr Cys Ala Gly Gln Ile Val Ser Gly
            50                  55                  60

Asn Val Asp Gln Ser Asp Gly Ser Phe Leu Glu Asp Ser His Leu Glu
65                  70                  75                  80

Lys Gly Tyr Val Leu Thr Cys Val Ala Tyr Pro Gln Ser Asp Cys Val
                85                  90                  95

Ile His Thr His Lys Glu Thr Glu Leu Phe
            100                 105

<210> SEQ ID NO 40
```

```
<211> LENGTH: 97
<212> TYPE: PRT
<213> ORGANISM: Zea mays

<400> SEQUENCE: 40

Ala Val Tyr Lys Val Lys Leu Val Gly Pro Glu Gly Glu His Glu
1               5                   10                  15

Phe Asp Ala Pro Asp Asp Ala Tyr Ile Leu Asp Ala Ala Glu Thr Ala
            20                  25                  30

Gly Val Glu Leu Pro Tyr Ser Cys Arg Ala Gly Ala Cys Ser Thr Cys
        35                  40                  45

Ala Gly Lys Ile Glu Ser Gly Ser Val Asp Gln Ser Asp Gly Ser Phe
    50                  55                  60

Leu Asp Asp Gly Gln Gln Glu Glu Gly Tyr Val Leu Thr Cys Val Ser
65                  70                  75                  80

Tyr Pro Lys Ser Asp Cys Val Ile His Thr His Lys Glu Gly Asp Leu
                85                  90                  95

Tyr

<210> SEQ ID NO 41
<211> LENGTH: 97
<212> TYPE: PRT
<213> ORGANISM: Zea mays

<400> SEQUENCE: 41

Val Leu His Lys Val Lys Leu Val Gly Pro Asp Gly Thr Glu His Glu
1               5                   10                  15

Phe Glu Ala Pro Asp Asp Thr Tyr Ile Leu Glu Ala Ala Glu Thr Ala
            20                  25                  30

Gly Val Glu Leu Pro Phe Ser Cys Arg Ala Gly Ser Cys Ser Thr Cys
        35                  40                  45

Ala Gly Arg Met Ser Ala Gly Glu Val Asp Gln Ser Glu Gly Ser Phe
    50                  55                  60

Leu Asp Asp Gly Gln Met Ala Glu Gly Tyr Leu Leu Thr Cys Ile Ser
65                  70                  75                  80

Tyr Pro Lys Ala Asp Cys Val Ile His Thr His Lys Glu Glu Asp Leu
                85                  90                  95

Tyr

<210> SEQ ID NO 42
<211> LENGTH: 98
<212> TYPE: PRT
<213> ORGANISM: Desmonostoc muscorum

<400> SEQUENCE: 42

Ala Thr Tyr Lys Val Arg Leu Phe Asn Ala Ala Glu Gly Leu Asp Glu
1               5                   10                  15

Thr Ile Glu Val Pro Asp Asp Glu Tyr Ile Leu Asp Ala Ala Glu Glu
            20                  25                  30

Ala Gly Leu Asp Leu Pro Phe Ser Cys Arg Ser Gly Ser Cys Ser Ser
        35                  40                  45

Cys Asn Gly Ile Leu Lys Lys Gly Thr Val Asp Gln Ser Asp Gln Asn
    50                  55                  60

Phe Leu Asp Asp Asp Gln Ile Ala Ala Gly Asn Val Leu Thr Cys Val
65                  70                  75                  80

Ala Tyr Pro Thr Ser Asn Cys Glu Ile Glu Thr His Arg Glu Asp Ala
                85                  90                  95
```

Ile Ala

<210> SEQ ID NO 43
<211> LENGTH: 91
<212> TYPE: PRT
<213> ORGANISM: Synechococcus PCC7002

<400> SEQUENCE: 43

Tyr Lys Val Thr Leu Ile Thr Pro Asp Gly Glu Val Ser Tyr Asp Ala
1               5                   10                  15

Pro Asp Asp Glu Tyr Ile Leu Asp Ser Ala Gly Asp Ala Gly Tyr Asp
            20                  25                  30

Leu Pro Ala Ser Cys Arg Ala Gly Ala Cys Ser Thr Cys Ala Gly Lys
        35                  40                  45

Ile Val Ser Gly Thr Val Asp Gln Ser Glu Gln Ser Phe Leu Asp Asp
    50                  55                  60

Asp Gln Ile Glu Ala Gly Tyr Val Leu Thr Cys Ile Ala Tyr Pro Gln
65                  70                  75                  80

Ser Asp Val Thr Ile Glu Thr Asn Lys Glu Glu
                85                  90

<210> SEQ ID NO 44
<211> LENGTH: 98
<212> TYPE: PRT
<213> ORGANISM: Prochlorococcus marinus

<400> SEQUENCE: 44

Ala Ser Tyr Lys Val Thr Leu Ile Ser Glu Ser Glu Gly Leu Asn Lys
1               5                   10                  15

Thr Ile Glu Val Pro Asp Asp Gln Tyr Ile Leu Asp Ala Ala Glu Glu
            20                  25                  30

Gln Gly Ile Asp Leu Pro Tyr Ser Cys Arg Ala Gly Ala Cys Ser Thr
        35                  40                  45

Cys Ala Gly Lys Leu Thr Gly Gly Ser Val Asp Gln Ser Asp Gln Ser
    50                  55                  60

Phe Leu Asp Asp Asp Gln Leu Glu Ala Gly Phe Val Leu Thr Cys Val
65                  70                  75                  80

Ala Tyr Pro Thr Ser Asp Cys Thr Ile Lys Thr His Ala Glu Glu
                85                  90                  95

Leu Tyr

<210> SEQ ID NO 45
<211> LENGTH: 98
<212> TYPE: PRT
<213> ORGANISM: Prochlorococcus marinus

<400> SEQUENCE: 45

Ala Ser Tyr Lys Val Thr Leu Ile Ser Glu Ser Glu Gly Leu Asn Ser
1               5                   10                  15

Thr Ile Glu Val Pro Asp Asp Gln Tyr Ile Leu Asp Ala Ala Glu Glu
            20                  25                  30

Gln Gly Val Asp Leu Pro Tyr Ser Cys Arg Ala Gly Ala Cys Ser Thr
        35                  40                  45

Cys Ala Gly Lys Ile Thr Ser Gly Thr Val Asp Gln Ser Asp Gln Ser
    50                  55                  60

Phe Leu Asp Asp Asp Gln Leu Glu Ala Gly Phe Val Leu Thr Cys Val
65                  70                  75                  80

Ala Tyr Pro Ser Ser Asp Val Thr Ile Thr Thr His Ala Glu Glu Glu
                85                  90                  95

Leu Tyr

<210> SEQ ID NO 46
<211> LENGTH: 98
<212> TYPE: PRT
<213> ORGANISM: Nostoc muscorum

<400> SEQUENCE: 46

Ala Thr Val Tyr Lys Val Thr Leu Val Asp Gln Glu Gly Thr Glu Thr
1               5                   10                  15

Thr Ile Asp Val Pro Asp Asp Glu Tyr Ile Leu Asp Ile Ala Glu Asp
                20                  25                  30

Gln Gly Leu Asp Leu Pro Tyr Ser Cys Arg Ala Gly Ala Cys Ser Thr
            35                  40                  45

Cys Ala Gly Lys Ile Val Ser Gly Thr Val Asp Gln Ser Asp Gln Ser
        50                  55                  60

Phe Leu Asp Asp Asp Gln Ile Glu Lys Gly Tyr Val Leu Thr Cys Val
65                  70                  75                  80

Ala Tyr Pro Thr Ser Asp Leu Lys Ile Glu Thr His Lys Glu Glu Asp
                85                  90                  95

Leu Tyr

<210> SEQ ID NO 47
<211> LENGTH: 98
<212> TYPE: PRT
<213> ORGANISM: Synechococcus elongatus

<400> SEQUENCE: 47

Ala Thr Tyr Lys Val Thr Leu Val Asn Ala Ala Glu Gly Leu Asn Thr
1               5                   10                  15

Thr Ile Asp Val Ala Asp Asp Thr Tyr Ile Leu Asp Ala Ala Glu Glu
                20                  25                  30

Gln Gly Ile Asp Leu Pro Tyr Ser Cys Arg Ala Gly Ala Cys Ser Thr
            35                  40                  45

Cys Ala Gly Lys Val Val Ser Gly Thr Val Asp Gln Ser Asp Gln Ser
        50                  55                  60

Phe Leu Asp Asp Asp Gln Ile Ala Ala Gly Phe Val Leu Thr Cys Val
65                  70                  75                  80

Ala Tyr Pro Thr Ser Asp Val Thr Ile Glu Thr His Lys Glu Glu Asp
                85                  90                  95

Leu Tyr

<210> SEQ ID NO 48
<211> LENGTH: 98
<212> TYPE: PRT
<213> ORGANISM: Anabaena variabilis

<400> SEQUENCE: 48

Ala Thr Phe Lys Val Thr Leu Ile Asn Glu Ala Glu Gly Thr Ser Asn
1               5                   10                  15

Thr Ile Asp Val Pro Asp Asp Glu Tyr Ile Leu Asp Ala Ala Glu Glu
                20                  25                  30

Gln Gly Tyr Asp Leu Pro Phe Ser Cys Arg Ala Gly Ala Cys Ser Thr
            35                  40                  45

```
Cys Ala Gly Lys Leu Val Ser Gly Thr Val Asp Gln Ser Asp Gln Ser
    50                  55                  60

Phe Leu Asp Asp Asp Gln Ile Glu Ala Gly Tyr Val Leu Thr Cys Val
65                  70                  75                  80

Ala Tyr Pro Thr Ser Asp Val Thr Ile Gln Thr His Lys Glu Glu Asp
                85                  90                  95

Leu Tyr
```

<210> SEQ ID NO 49
<211> LENGTH: 97
<212> TYPE: PRT
<213> ORGANISM: Datura stramonium

<400> SEQUENCE: 49

```
Ala Thr Tyr Lys Val Lys Leu Val Thr Pro Asp Gly Pro Val Glu Phe
1               5                   10                  15

Asn Cys Pro Asp Asp Val Tyr Ile Leu Asp Gln Ala Glu Glu Glu Gly
                20                  25                  30

His Asp Leu Pro Tyr Ser Cys Arg Ala Gly Ser Cys Ser Ser Cys Ala
            35                  40                  45

Gly Lys Val Thr Ala Gly Thr Val Asp Gln Ser Asp Gly Asn Tyr Leu
    50                  55                  60

Asp Asp Asp Gln Met Ala Asp Gly Phe Val Leu Thr Cys Val Ala Tyr
65                  70                  75                  80

Pro Gln Ser Asp Val Thr Ile Glu Thr His Lys Glu Glu Leu Thr
                85                  90                  95

Gly
```

<210> SEQ ID NO 50
<211> LENGTH: 97
<212> TYPE: PRT
<213> ORGANISM: Alocasia macrorrhiza

<400> SEQUENCE: 50

```
Ala Thr Tyr Lys Val Lys Leu Val Thr Pro Gln Gly Gln Gln Glu Phe
1               5                   10                  15

Asp Cys Pro Asp Asp Val Tyr Ile Leu Asp Gln Ala Glu Glu Glu Gly
                20                  25                  30

Ile Asp Leu Pro Tyr Ser Cys Arg Ala Gly Ser Cys Ser Ser Cys Ala
            35                  40                  45

Gly Lys Val Lys Gln Gly Glu Val Asp Gln Ser Asp Gly Ser Phe Leu
    50                  55                  60

Asp Asp Glu Gln Met Glu Gln Gly Trp Val Leu Thr Cys Val Ala Phe
65                  70                  75                  80

Pro Thr Ser Asp Val Val Ile Glu Thr His Lys Glu Glu Glu Leu Thr
                85                  90                  95

Ala
```

<210> SEQ ID NO 51
<211> LENGTH: 96
<212> TYPE: PRT
<213> ORGANISM: Arabidopsis thaliana

<400> SEQUENCE: 51

```
Ala Thr Tyr Lys Val Lys Phe Ile Thr Pro Glu Gly Glu Gln Glu Val
1               5                   10                  15

Glu Cys Glu Glu Asp Val Tyr Val Leu Asp Ala Ala Glu Glu Ala Gly
```

```
                20                  25                  30

Leu Asp Leu Pro Tyr Ser Cys Arg Ala Gly Ser Cys Ser Cys Ala
            35                  40                  45

Gly Lys Val Val Ser Gly Ser Ile Asp Gln Ser Asp Gln Ser Phe Leu
            50                  55                  60

Asp Asp Glu Gln Met Ser Glu Gly Tyr Val Leu Thr Cys Val Ala Tyr
65                  70                  75                  80

Pro Thr Ser Asp Val Val Ile Glu Thr His Lys Glu Glu Ala Ile Met
                85                  90                  95

<210> SEQ ID NO 52
<211> LENGTH: 97
<212> TYPE: PRT
<213> ORGANISM: Zea mays

<400> SEQUENCE: 52

Ala Thr Tyr Asn Val Lys Leu Ile Thr Pro Glu Gly Glu Val Glu Leu
1               5                   10                  15

Gln Val Pro Asp Asp Val Tyr Ile Leu Asp Tyr Ala Glu Glu Glu Gly
                20                  25                  30

Ile Asp Leu Pro Tyr Ser Cys Arg Ala Gly Ser Cys Ser Ser Cys Ala
            35                  40                  45

Gly Lys Val Val Ser Gly Ser Leu Asp Gln Ser Asp Gln Ser Phe Leu
            50                  55                  60

Asp Asp Ser Gln Val Ala Asp Gly Trp Val Leu Thr Cys Val Ala Tyr
65                  70                  75                  80

Pro Thr Ser Asp Val Val Ile Glu Thr His Lys Glu Asp Asp Leu Ile
                85                  90                  95

Ser

<210> SEQ ID NO 53
<211> LENGTH: 96
<212> TYPE: PRT
<213> ORGANISM: Zea mays

<400> SEQUENCE: 53

Ala Thr Tyr Asn Val Lys Leu Ile Thr Pro Glu Gly Glu Val Glu Leu
1               5                   10                  15

Gln Val Pro Asp Asp Val Tyr Ile Leu Asp Phe Ala Glu Glu Glu Gly
                20                  25                  30

Ile Asp Leu Pro Phe Ser Cys Arg Ala Gly Ser Cys Ser Ser Cys Ala
            35                  40                  45

Gly Lys Val Val Ser Gly Ser Val Asp Gln Ser Asp Gln Ser Phe Leu
            50                  55                  60

Asn Asp Asn Gln Val Ala Asp Gly Trp Val Leu Thr Cys Ala Ala Tyr
65                  70                  75                  80

Pro Thr Ser Asp Val Val Ile Glu Thr His Lys Glu Asp Asp Leu Leu
                85                  90                  95

<210> SEQ ID NO 54
<211> LENGTH: 107
<212> TYPE: PRT
<213> ORGANISM: Prochlorococcus marinus

<400> SEQUENCE: 54

Ser Glu Tyr Asn Ile Lys Val Glu Leu Glu Lys Lys Thr Tyr Val Phe
1               5                   10                  15
```

Leu Cys Pro Glu Asp Gln Asp Ile Ile Ser Ala Ala Lys Ala Asn Gly
                20                  25                  30

Ile Asp Leu Pro Ser Ser Cys Ser Gly Val Cys Thr Ser Cys Ala
            35                  40                  45

Ser Met Val Ile Asp Gly Ser Val Glu Gln Glu Asp Ala Met Gly Leu
50                      55                  60

Asn Asp Asp Leu Lys Glu Lys Gly Phe Ala Leu Leu Cys Val Ala Tyr
65                  70                  75                  80

Pro Lys Ser Asp Leu His Ile Ile Gly Asp Glu Val Glu Asp Asn
                85                  90                  95

Leu Tyr Asn Asn Gln Phe Gly Lys Tyr Gln Ile
            100                 105

<210> SEQ ID NO 55
<211> LENGTH: 104
<212> TYPE: PRT
<213> ORGANISM: Synechococcus elongatus

<400> SEQUENCE: 55

Ala Thr Tyr Gln Val Glu Val Ile Tyr Gln Gly Gln Ser Gln Thr Phe
1               5                   10                  15

Thr Ala Asp Ser Asp Gln Ser Val Leu Asp Ser Ala Gln Ala Ala Gly
                20                  25                  30

Val Asp Leu Pro Ala Ser Cys Leu Thr Gly Val Cys Thr Thr Cys Ala
            35                  40                  45

Ala Arg Ile Leu Ser Gly Glu Val Asp Gln Pro Asp Ala Met Gly Val
50                      55                  60

Gly Pro Glu Pro Ala Lys Gln Gly Tyr Thr Leu Leu Cys Val Ala Tyr
65                  70                  75                  80

Pro Arg Ser Asp Leu Lys Ile Glu Thr His Lys Glu Asp Glu Leu Tyr
                85                  90                  95

Ala Leu Gln Phe Gly Gln Pro Gly
            100

<210> SEQ ID NO 56
<211> LENGTH: 105
<212> TYPE: PRT
<213> ORGANISM: Synechocystis PCC6803

<400> SEQUENCE: 56

Val Asn Thr Tyr Thr Ala Glu Ile Gln His Gln Gly Gln Thr Tyr Thr
1               5                   10                  15

Ile Ser Val Pro Glu Asp Lys Thr Val Leu Gln Ala Ala Asp Asp Glu
                20                  25                  30

Gly Ile Gln Leu Pro Thr Ser Cys Gly Ala Gly Val Cys Thr Thr Cys
            35                  40                  45

Ala Ala Leu Ile Thr Glu Gly Thr Ala Glu Gln Ala Asp Gly Met Gly
50                      55                  60

Val Ser Ala Glu Leu Gln Ala Glu Gly Tyr Ala Leu Leu Cys Val Ala
65                  70                  75                  80

Tyr Pro Arg Ser Asp Leu Lys Ile Ile Thr Glu Lys Glu Asp Glu Val
                85                  90                  95

Tyr Gln Arg Gln Phe Gly Gly Gln Gly
            100                 105

<210> SEQ ID NO 57
<211> LENGTH: 129

```
<212> TYPE: PRT
<213> ORGANISM: Chlamydomonas reinhardtii

<400> SEQUENCE: 57

Lys Ile Lys Ile Phe Asp His Tyr Gly Asn Gln Glu Ile Asp Val Glu
1               5                   10                  15

Val Pro Glu Asp Arg Tyr Ile Leu Trp Glu Ala Glu Asp Lys Gly Leu
            20                  25                  30

Glu Leu Pro Tyr Ala Cys Arg Met Gly Cys Cys Thr Ala Cys Ala Val
        35                  40                  45

Arg Val Lys Glu Gly Glu Val His Gln Pro Glu Ala Leu Gly Ile Ser
    50                  55                  60

Ala Glu Leu Arg Glu Met Gly Tyr Ala Leu Met Cys Val Gly Tyr Pro
65                  70                  75                  80

Thr Ser Asp Ala Val Met Glu Thr Val Ser Asp Glu Ile Tyr Glu
                85                  90                  95

Leu Gln Phe Gly Lys Tyr Phe Ala Gln Gln Ala Leu Asp Pro Asn Ser
            100                 105                 110

Glu Ser Ile Glu Arg Asp Asp Tyr Ala Leu Ser Ile Ala Asn Met Asp
        115                 120                 125

Glu

<210> SEQ ID NO 58
<211> LENGTH: 123
<212> TYPE: PRT
<213> ORGANISM: Prochlorococcus marinus

<400> SEQUENCE: 58

Lys Lys Thr Phe Lys Val Thr Ile Thr Asn Lys Glu Thr Gly Lys Ile
1               5                   10                  15

Tyr Gln Glu Asn Ile Ser Asp Gln Glu Tyr Ile Leu Lys Glu Phe Glu
            20                  25                  30

Lys Lys Gly Leu Arg Leu Pro Phe Ser Cys Arg Asn Gly Cys Cys Thr
        35                  40                  45

Ser Cys Ala Val Lys Ile Ile Ser Gly Lys Leu Asp Gln Pro Glu Ala
    50                  55                  60

Met Gly Val Ser Gln Asp Leu Lys Asp Lys Gly Tyr Ala Leu Leu Cys
65                  70                  75                  80

Val Ala Lys Val Ile Glu Asp Ile Glu Val Glu Thr Thr Tyr Tyr Asp
                85                  90                  95

Glu Val Tyr Asp Leu Gln Phe Gly Gln Tyr Phe Gly Lys Gly Lys Thr
            100                 105                 110

Arg Lys Ala Pro Pro Trp Glu Phe Glu Glu Asp
        115                 120

<210> SEQ ID NO 59
<211> LENGTH: 121
<212> TYPE: PRT
<213> ORGANISM: Synechococcus elongatus

<400> SEQUENCE: 59

Ser Asp Thr Tyr Thr Val Arg Ile Arg Asp Arg Arg Thr Asp Glu Glu
1               5                   10                  15

Phe Thr Val Gln Val Pro Pro Asp Arg Tyr Ile Leu Gln Thr Ala Glu
            20                  25                  30

Glu Gln Gly Tyr Glu Leu Pro Phe Ser Cys Arg Asn Gly Ala Cys Thr
        35                  40                  45
```

-continued

```
Ala Cys Ala Val Arg Val Leu Gly Gly Ala Ile Glu Gln Thr Glu Ala
    50                  55                  60

Met Gly Leu Ser Ala Pro Leu Arg Gln Arg Gly Tyr Ala Leu Leu Cys
65                  70                  75                  80

Val Ser Tyr Pro Arg Ser Asp Val Ile Val Glu Thr Gln Asp Glu Asp
                85                  90                  95

Glu Val Tyr Met Leu Gln Phe Gly Arg Tyr Phe Gly Gln Gly Lys Val
            100                 105                 110

Ser Phe Gly Leu Pro Leu Asp Glu Glu
            115                 120

<210> SEQ ID NO 60
<211> LENGTH: 121
<212> TYPE: PRT
<213> ORGANISM: Synechocystis PCC6803

<400> SEQUENCE: 60

Ser Arg Ser His Arg Val Leu Ile His Asp Arg Gln Asn Glu Lys Asp
1               5                   10                  15

Tyr Ser Val Ile Val Ser Asp Asp Arg Tyr Ile Leu His Gln Ala Glu
            20                  25                  30

Asp Gln Gly Phe Glu Leu Pro Phe Ser Cys Arg Asn Gly Ala Cys Thr
        35                  40                  45

Ala Cys Ala Val Arg Val Ile Ser Gly Gln Ile His Gln Pro Glu Ala
    50                  55                  60

Met Gly Leu Ser Pro Asp Leu Gln Arg Gln Gly Tyr Ala Leu Leu Cys
65                  70                  75                  80

Val Ser Tyr Ala Gln Ser Asp Leu Glu Val Glu Thr Gln Asp Glu Asp
                85                  90                  95

Glu Val Tyr Glu Leu Gln Phe Gly Arg Tyr Phe Gly Ala Gly Arg Val
            100                 105                 110

Arg Leu Gly Leu Pro Leu Asp Glu Asp
            115                 120
```